(12) United States Patent
Habgood et al.

(10) Patent No.: US 8,008,499 B2
(45) Date of Patent: Aug. 30, 2011

(54) ANABASEINE DERIVATIVES, PHARMACEUTICAL COMPOSITIONS AND METHODS OF USE THEREOF

(75) Inventors: Gregory J. Habgood, Merrimac, MA (US); Daniel Elbaum, Newton, MA (US)

(73) Assignee: Cornerstone Therapeutics, Inc., Cary, NC (US)

( * ) Notice: Subject to any disclaimer, the term of this patent is extended or adjusted under 35 U.S.C. 154(b) by 0 days.

(21) Appl. No.: 12/649,463

(22) Filed: Dec. 30, 2009

(65) Prior Publication Data
US 2010/0311773 A1 Dec. 9, 2010

Related U.S. Application Data

(63) Continuation of application No. 11/698,267, filed on Jan. 25, 2007, now Pat. No. 7,662,965.

(60) Provisional application No. 60/762,544, filed on Jan. 26, 2006.

(51) Int. Cl.
- C07D 217/02 (2006.01)
- C07D 215/02 (2006.01)
- C07D 421/00 (2006.01)
- C07D 213/22 (2006.01)

(52) U.S. Cl. ......... 546/144; 546/167; 546/256; 546/257

(58) Field of Classification Search .................. 546/144, 546/167, 256, 257
See application file for complete search history.

(56) References Cited

U.S. PATENT DOCUMENTS

| 5,741,802 A | 4/1998 | Kem et al. |
| 2004/0229868 A1 | 11/2004 | Herbert et al. |
| 2007/0232651 A1 | 10/2007 | Habgood et al. |

FOREIGN PATENT DOCUMENTS

| WO | WO 94/05288 | 3/1994 |
| WO | WO 99/10338 | 3/1999 |
| WO | WO 2004/019943 A1 | 3/2004 |
| WO | WO 2005/123075 A2 | 2/2005 |
| WO | WO 2006/133303 A1 | 12/2006 |

OTHER PUBLICATIONS

Kern, W.R., "The brain α7 nicotinic receptor may be an important therapeutic target for the treatment of Alzheimer's disease: studies with DMXBA (GTS-21)," *Behavioural Brain Research*, 113:169-181 (2000).

Stokes, C. et al., "The Structural Basis for GTS-21 Selectivity between Human and Rat Nicotinic α7 Receptors," *Molecular Pharmacology*, 66(1):14-24 (2004).

*Primary Examiner* — Nizal Chandrakumar
(74) *Attorney, Agent, or Firm* — Riverside Law LLP

(57) ABSTRACT

Disclosed are novel anabaseine derivatives that act as agonists of the α7 nAChR. Also disclosed are pharmaceutical compositions, methods of treating inflammatory conditions, methods of treating CNS disorders, methods for inhibiting cytokine release from mammalian cells and methods for the preparation of the novel compounds.

1 Claim, No Drawings

ANABASEINE DERIVATIVES, PHARMACEUTICAL COMPOSITIONS AND METHODS OF USE THEREOF

RELATED APPLICATION

This application is a continuation of U.S. application Ser. No. 11/698,267, filed Jan. 25, 2007, now U.S. Pat. No. 7,662,965 which claims the benefit of U.S. Provisional Application No. 60/762,544, filed on Jan. 26, 2006. The entire teachings of the above applications are incorporated herein by reference.

BACKGROUND OF THE INVENTION

Nicotinic acetylcholine receptors (nAChRs) are a family of ligand-gated ion channels found at the neuromuscular junction as well as throughout the central and peripheral nervous systems. In humans, 16 different nAChR subunits have been identified and include $\alpha 1$-$\alpha 7$, $\alpha 9$-$\alpha 10$, $\beta 1$-$4$, $\delta$, $\epsilon$ and $\gamma$ (Lindstrom, 1995. Nicotinic acetylcholine receptors in "Handbook of Receptors and Channels: Ligand- and Voltage-Gated Ion Channels." Edited by R. Alan North. CRC Press, Inc.). These subunits can co-assemble to form numerous homo- and heteropentameric subtypes which in turn are characterized by distinct ligand-binding and pharmacologic properties (Lindstrom, 1995).

The $\alpha 7$ nAChR subtype has been reported to play a role in several diseases of the central nervous system (CNS) including Alzheimer's disease (Wang et al, J. Biol. Chem. 275(8): 5626-32 (2000), Kem, Brain Biol. Res. 113(1-2): 169-81 (2000)), schizophrenia (Adler et al, Schizophr Bull 24(2): 189-202 (1998)), Parkinson's disease (Quik et al, Eur J Pharm 393(1-3) 223-30 (2000)) and attention deficit-hyperactivity disorder (Wilens et al, Am J Psychiatry 156(12): 1931-7 (1999), Levin et al, Eur J. Pharmacol. 393(1-3): 141-6 (2000)). Selective agonists of the $\alpha 7$ nAChR subtype have therefore been proposed as useful for the treatment of these and other central nervous system conditions (U.S. Pat. Nos. 6,110,914, 5,902,814, 6,599,916, 6,432,975; Kem et al, Behav. Brain Res. 113(1-2): 169-81 (2000), Martin et al, Psychopharmacology, Feb. 19 (2004)).

The $\alpha 7$ nAChR subtype has also recently been shown to have involvement in the inflammatory response (Wang et al, Nature, 421(6921):384-8 (2003)). Wang et al demonstrated that activation of the $\alpha 7$ nAChR inhibits the release of proinflammatory cytokines, such as tumor necrosis factor alpha (TNF-$\alpha$) and high mobility group box 1 protein (HMGB1), from macrophage cells and confers protection against lethality in a murine model of sepsis. Selective agonists of $\alpha 7$ nAChRs have been demonstrated to have utility as anti-inflammatory agents by inhibiting the release of TNF-$\alpha$ and other proinflammatory cytokines (WO 2004/052365 A2).

Given the therapeutic potential of $\alpha 7$ nAChR agonists in the treatment of inflammatory conditions, CNS conditions as well as other deleterious conditions, there remains a need in the art for additional $\alpha 7$ nAChR agonists.

SUMMARY OF THE INVENTION

It has now been discovered that certain novel anabaseine derivatives act as agonists of the $\alpha 7$ nAChR. Based on this discovery, novel compounds, pharmaceutical compositions, methods of treating inflammatory conditions, methods of treating CNS disorders, methods for inhibiting cytokine release from mammalian cells and methods for the preparation of the novel compounds are disclosed.

In one embodiment, the invention pertains to a compound of the Formula (I):

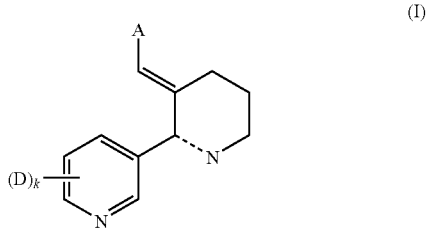

or a pharmaceutically acceptable salt thereof, wherein:

A is selected from the group consisting of $R_1$ and $R_2$;

Each D is independently selected from the group consisting of C1-C10 alkyl, C1-C10 alkyl substituted with one or more $R_8$, C2-C10 alkenyl, C2-C10 alkenyl substituted with one or more $R_8$, C2-C10 alkynyl, C2-C10 alkynyl substituted with one or more $R_8$, C3-C10 cycloalkyl, C3-C10 cycloalkyl substituted with one or more $R_9$, C4-C10 cycloalkenyl, C4-C10 cycloalkenyl substituted with one or more $R_9$, 3-8 membered heterocycloalkyl, 3-8 membered heterocycloalkyl substituted with one or more $R_9$, 4-10 membered heterocycloalkenyl, 4-10 membered heterocycloalkenyl substituted with one or more $R_9$, C5-C11 bicycloalkyl, C5-C11 bicycloalkyl substituted with one or more $R_9$, C5-C11 bicycloalkenyl, C5-C11 bicycloalkenyl substituted with one or more $R_9$, 5-11 membered heterobicycloalkyl, 5-11 membered heterobicycloalkyl substituted with one or more $R_9$, 5-11 membered heterobicycloalkenyl, 5-11 membered heterobicycloalkenyl substituted with one or more $R_9$, halo, haloalkyl, $OR_7$, $SR_7$, $NR_7R_7$, $C(O)OR_7$, $NO_2$, $CN$, $C(O)R_7$, $C(O)C(O)R_7$, $C(O)NR_7R_7$, $C(O)C(O)NR_7R_7$, $N(R_7)C(O)R_7$, $NR_7S(O)_qR_7$, $N(R_7)C(O)OR_7$, $NR_7C(O)C(O)R_7$, $NR_7C(O)NR_7R_7$, $NR_7S(O)_qNR_7R_7$, $NR_7S(O)_qR_7$, $S(O)_qR_7$, $S(O)_qNR_7R_7$, $OC(O)R_7$, aryl and heteroaryl, wherein said aryl and heteroaryl are each optionally substituted with one or more $R_{11}$;

$R_1$ is selected from the group consisting of:

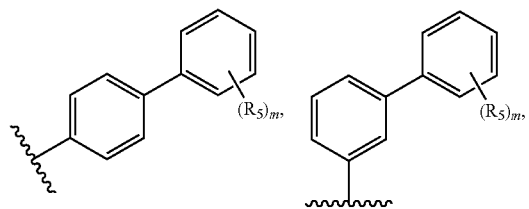

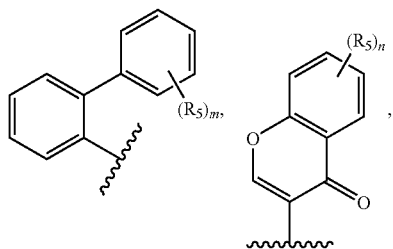

-continued

[chemical structures shown: chromone with $(R_5)_n$; pyridines with $(R_6)_n$; fluorenyl groups with $(R_5)_p$; furan with $R_{10}$]

$R_2$ is $R_3$—X—$R^4$;

$R_3$ is selected from the group consisting of a 6 membered monocyclic aryl and 5 or 6 membered monocyclic heteroaryl comprising 1-3 heteroatoms, wherein each of said heteroatoms is independently selected from the group consisting of O, N and S, and wherein said aryl and heteroaryl are each optionally substituted with one or more $R_{11}$;

X is selected from the group consisting of O, $NR_7$ and $NR_7CONR_7$;

$R_4$ is selected from the group consisting of C3-C8 cycloalkyl, C3-C8 cycloalkyl substituted with one or more $R_9$, C4-C10 cycloalkenyl, C4-C10 cycloalkenyl substituted with one or more $R_9$, 3-8 membered heterocycloalkyl, 3-8 membered heterocycloalkyl substituted with one or more $R_9$, 4-10 membered heterocycloalkenyl, 4-10 membered heterocycloalkenyl substituted with one or more $R_9$, C5-C11 bicycloalkyl, C5-C11 bicycloalkyl substituted with one or more $R_9$, C5-C11 bicycloalkenyl, C5-C11 bicycloalkenyl substituted with one or more $R_9$, 5-11 membered heterobicycloalkyl, 5-11 membered heterobicycloalkyl substituted with one or more $R_9$, 5-11 membered heterobicycloalkenyl, 5-11 membered heterobicycloalkenyl substituted with one or more $R_9$, aryl and heteroaryl, wherein said aryl and heteroaryl are each optionally substituted with one or more $R_{11}$;

Each $R_5$ is independently selected from the group consisting of C1-C10 alkyl, C1-C10 alkyl substituted with one or more $R_8$, C2-C10 alkenyl, C2-C10 alkenyl substituted with one or more $R_8$, C2-C10 alkynyl, C2-C10 alkynyl substituted with one or more $R_8$, C3-C10 cycloalkyl, C3-C10 cycloalkyl substituted with one or more $R_9$, C4-C10 cycloalkenyl, C4-C10 cycloalkenyl substituted with one or more $R_9$, 3-8 membered heterocycloalkyl, 3-8 membered heterocycloalkyl substituted with one or more $R_9$, 4-10 membered heterocycloalkenyl, 4-10 membered heterocycloalkenyl substituted with one or more $R_9$, C5-C11 bicycloalkyl, C5-C11 bicycloalkyl substituted with one or more $R_9$, C5-C11 bicycloalkenyl, C5-C11 bicycloalkenyl substituted with one or more $R_9$, 5-11 membered heterobicycloalkyl, 5-11 membered heterobicycloalkyl substituted with one or more $R_9$, 5-11 membered heterobicycloalkenyl, 5-11 membered heterobicycloalkenyl substituted with one or more $R_9$, halo, haloalkyl, $OR_7$, $SR_7$, $NR_7R_7$, $C(O)OR_7$, $NO_2$, CN, $C(O)R_7$, $C(O)C(O)R_7$, $C(O)NR_7R_7$, $C(O)C(O)NR_7R_7$, $N(R_7)C(O)R_7$, $NR_7S(O)_qR_7$, $N(R_7)C(O)OR_7$, $NR_7C(O)C(O)R_7$, $NR_7C(O)NR_7R_7$, $NR_7S(O)_qNR_7R_7$, $NR_7S(O)_qR_7$, $S(O)_qR_7$, $S(O)_qNR_7R_7$, $OC(O)R_7$, aryl and heteroaryl, wherein said aryl and heteroaryl are each optionally substituted with one or more $R_{11}$;

Each $R_6$ is independently selected from the group consisting of C1-C10 alkyl, C1-C10 alkyl substituted with one or more $R_8$, C2-C10 alkenyl, C2-C10 alkenyl substituted with one or more $R_8$, C2-C10 alkynyl, C2-C10 alkynyl substituted with one or more $R_8$, C3-C10 cycloalkyl, C3-C10 cycloalkyl substituted with one or more $R_9$, C4-C10 cycloalkenyl, C4-C10 cycloalkenyl substituted with one or more $R_9$, C5-C11 bicycloalkyl, C5-C11 bicycloalkyl substituted with one or more $R_9$, C5-C11 bicycloalkenyl, C5-C11 bicycloalkenyl substituted with one or more $R_9$, halo, haloalkyl, $OR_7$, $SR_7$, $NR_7R_7$, $C(O)OR_7$, $NO_2$, CN, $C(O)R_7$, $C(O)C(O)R_7$, $C(O)NR_7R_7$, $C(O)C(O)NR_7R_7$, $N(R_7)C(O)R_7$, $NR_7S(O)_qR_7$, $N(R_7)C(O)OR_7$, $NR_7C(O)C(O)R_7$, $NR_7C(O)NR_7R_7$, $NR_7S(O)_qNR_7R_7$, $NR_7S(O)_qR_7$, $S(O)_qR_7$, $S(O)_qNR_7R_7$ and $OC(O)R_7$;

Each $R_7$ is independently selected from the group consisting of H, C1-C10 alkyl, C2-C10 alkenyl, C2-C10 alkynyl, C3-C10 cycloalkyl, C4-C10 cycloalkenyl, 3-10 membered heterocycloalkyl, 4-10 membered heterocycloalkenyl, haloalkyl, aryl and heteroaryl, wherein said aryl and heteroaryl are each optionally substituted with one or more $R_{11}$;

Each $R_8$ is independently selected from the group consisting of halo, haloalkyl, $OR_7$, $SR_7$, $C(O)R_7$, $OC(O)R_7$, $C(O)OR_7$, $NR_7R_7$, $NO_2$, CN, $OC(O)NR_7R_7$, $C(O)NR_7R_7$, $N(R_7)C(O)R_7$, $N(R_7)(COOR_7)$, $S(O)_qNR_7R_7$, C3-C8 cycloalkyl, C4-C10 cycloalkenyl, 3-8 membered heterocycloalkyl, 4-10 membered heterocycloalkenyl, C5-C11 bicycloalkyl, C5-C11 bicycloalkenyl, 5-11 membered heterobicycloalkyl, 5-11 membered heterobicycloalkenyl, aryl and heteroaryl, wherein said aryl and heteroaryl are each optionally substituted with one or more $R_{11}$;

Each $R_9$ is independently selected from the group consisting of $R_8$, C1-C10 alkyl, C1-C10 alkyl substituted with one or more $R_8$, C2-C10 alkenyl, C2-C10 alkenyl substituted with one or more $R_8$, C2-C10 alkynyl and C2-C10 alkynyl substituted with one or more $R_8$;

$R_{10}$ is aryl or heteroaryl, wherein said aryl and heteroaryl are each optionally substituted with one or more $R_{11}$;

Each $R_{11}$ is independently selected from the group consisting of C1-C10 alkyl, C1-C10 alkyl substituted with one or more $R_8$, C2-C10 alkenyl, C2-C10 alkenyl substituted with one or more $R_8$, C2-C10 alkynyl, C2-C10 alkynyl substituted with one or more $R_8$, C3-C10 cycloalkyl, C3-C10 cycloalkyl substituted with one or more $R_9$, C4-C10 cycloalkenyl, C4-C10 cycloalkenyl substituted with one or more $R_9$, 3-8 membered heterocycloalkyl, 3-8 membered heterocycloalkyl substituted with one or more $R_9$, 4-10 membered heterocycloalkenyl, 4-10 membered heterocycloalkenyl substituted with one or more $R_9$, C5-C11 bicycloalkyl, C5-C11 bicycloalkyl substituted with one or more $R_9$, C5-C11 bicycloalkenyl, C5-C11 bicycloalkenyl substituted with one or more $R_9$, 5-11 membered heterobicycloalkyl, 5-11 membered heterobicycloalkyl substituted with one or more $R_9$, 5-11 membered heterobicycloalkenyl, 5-11 membered heterobicycloalkenyl substituted with one or more $R_9$, halo, haloalkyl, $OR_7$, $SR_7$, $NR_7R_7$, $C(O)OR_7$, $NO_2$, CN, $C(O)R_7$, $C(O)C(O)R_7$, $C(O)NR_7R_7$, $N(R_7)C(O)R_7$, $NR_7S(O)_2R_7$, $N(R_7)C(O)OR_7$, $NR_7C(O)C(O)R_7$, $NR_7C(O)NR_7R_7$, $NR_7S(O)_qNR_7R_7$, $NR_7S(O)_qR_7$, $S(O)_qR_7$, $S(O)_qNR_7R_7$, $OC(O)R_7$, optionally substituted aryl and optionally substituted heteroaryl;

k is an integer from 0 to 4;
m is an integer from 0 to 9;
Each n is independently an integer from 0 to 4;
Each p is independently an integer from 0 to 5; and
Each q is independently 1 or 2.

In another embodiment, the invention pertains to a compound of the Formula (II):

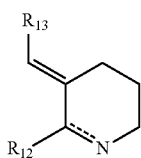

(II)

or a pharmaceutically acceptable salt thereof, wherein:
$R_{12}$ is selected from the group consisting of:

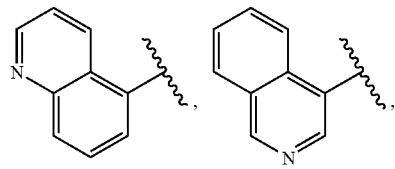

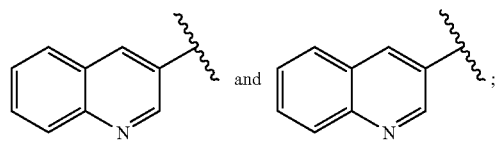
and $R_{13}$ is selected from the group consisting of 6 membered monocyclic aryl, 5 or 6 membered monocyclic heteroaryl comprising 1-3 heteroatoms, 8-12 membered bicyclic aryl, 8-12 membered bicyclic heteroaryl comprising 1-6 heteroatoms, 11-14 membered tricyclic aryl and 11-14 membered heteroaryl comprising 1-9 heteroatoms, wherein each of said heteroatoms is independently selected from the group consisting of O, N and S and wherein said aryl and heteroaryl are each optionally substituted with one or more $R_{17}$;

Each $R_{14}$ is independently selected from the group consisting of H, C1-C10 alkyl, C2-C10 alkenyl, C2-C10 alkynyl, C3-C10 cycloalkyl, C4-C10 cycloalkenyl, 3-10 membered heterocycloalkyl, 4-10 membered heterocycloalkenyl, haloalkyl aryl and heteroaryl, wherein said aryl and heteroaryl are each optionally substituted with one or more $R_{17}$;

Each $R_{15}$ is independently selected from the group consisting of halo, haloalkyl, $OR_{14}$, $SR_{14}$, $C(O)R_{14}$, $OC(O)R_{14}$, $C(O)OR_{14}$, $NR_{14}R_{14}$, $NO_2$, CN, $OC(O)NR_{14}R_{14}$, $C(O)NR_{14}R_{14}$, $N(R_{14})C(O)R_{14}$, $N(R_{14})(COOR_{14})$, $S(O)_tNR_{14}R_{14}$, C3-C8 cycloalkyl, C4-C10 cycloalkenyl, 3-8 membered heterocycloalkyl, 4-10 membered heterocycloalkenyl, C5-C11 bicycloalkyl, C5-C11 bicycloalkenyl, 5-11 membered heterobicycloalkyl, 5-11 membered heterobicycloalkenyl, aryl and heteroaryl, wherein said aryl and heteroaryl are each optionally substituted with one or more $R_{17}$;

Each $R_{16}$ is independently selected from the group consisting of $R_{15}$, C1-C10 alkyl, C1-C10 alkyl substituted with one or more $R_{15}$, C2-C10 alkenyl, C2-C10 alkenyl substituted with one or more $R_{15}$, C2-C10 alkynyl and C2-C10 alkynyl substituted with one or more $R_{15}$;

Each $R_{17}$ is independently selected from the group consisting of C1-C10 alkyl, C1-C10 alkyl substituted with one or more $R_{15}$, C2-C10 alkenyl, C2-C10 alkenyl substituted with one or more $R_{15}$, C2-C10 alkynyl, C2-C10 alkynyl substituted with one or more $R_{16}$, C3-C10 cycloalkyl, C3-C10 cycloalkyl substituted with one or more $R_{16}$, C4-C10 cycloalkenyl, C4-C10 cycloalkenyl substituted with one or more $R_{16}$, 3-8 membered heterocycloalkyl, 3-8 membered heterocycloalkyl substituted with one or more $R_{16}$, 4-10 membered heterocycloalkenyl, 4-10 membered heterocycloalkenyl substituted with one or more $R_{16}$, C5-C11 bicycloalkyl, C5-C11 bicycloalkyl substituted with one or more $R_{16}$, C5-C11 bicycloalkenyl, C5-C11 bicycloalkenyl substituted with one or more $R_{16}$, 5-11 membered heterobicycloalkyl, 5-11 membered heterobicycloalkyl substituted with one or more $R_{16}$, 5-11 membered heterobicycloalkenyl, 5-11 membered heterobicycloalkenyl substituted with one or more $R_{16}$, halo, $OR_{14}$, $SR_{14}$, $NR_{14}R_{14}$, $C(O)OR_{14}$, $NO_2$, CN, $C(O)R_{14}$, $C(O)C(O)R_{14}$, $C(O)NR_{14}R_{14}$, $C(O)C(O)NR_{14}R_{14}$, $N(R_{14})C(O)R_{14}$, $NR_{14}S(O)_tR_{14}$, $N(R_{14})C(O)OR_{14}$, $NR_{14}C(O)C(O)R_{14}$, $NR_{14}C(O)NR_{14}R_{14}$, $NR_{14}S(O)_tNR_{14}R_{14}$, $NR_{14}S(O)_tR_{14}$, $S(O)_tR_{14}$, $S(O)_tNR_{14}R_{14}$, $OC(O)R_{14}$, optionally substituted aryl and optionally substituted heteroaryl; and t is 1 or 2.

All stereoisomers and double bond geometries are encompassed.

In another embodiment, the invention is a compound having the Formula (III):

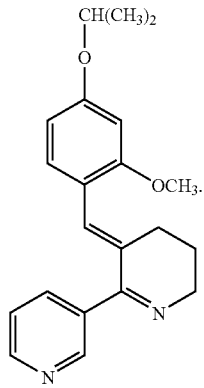

(III)

In yet another embodiment, the invention is a compound having the Formula (IV):

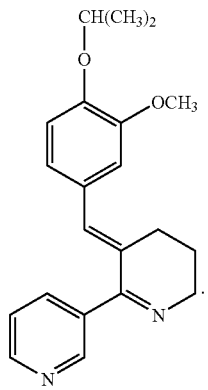

(IV)

In a further embodiment, the invention is a pharmaceutical composition comprising a pharmaceutically acceptable carrier and a compound represented by Formula (I) or a pharmaceutically acceptable salt thereof.

In another embodiment, the invention is a pharmaceutical composition comprising a pharmaceutically acceptable carrier and a compound represented by Formula (II) or a pharmaceutically acceptable salt thereof.

In yet another embodiment, the invention is a pharmaceutical composition comprising a pharmaceutically acceptable carrier and a compound represented by Formula (III) or a pharmaceutically acceptable salt thereof.

In another embodiment, the invention is a pharmaceutical composition comprising a pharmaceutically acceptable carrier and a compound represented by Formula (IV) or a pharmaceutically acceptable salt thereof.

In a further embodiment, the invention is directed to a method of treating a patient suffering from an inflammatory condition comprising administering to the patient a therapeutically effective amount of a compound represented by Formula (I) or a pharmaceutically acceptable salt thereof.

In a further embodiment, the invention is directed to a method of treating a patient suffering from an inflammatory condition comprising administering to the patient a therapeutically effective amount of a compound represented by Formula (II) or a pharmaceutically acceptable salt thereof.

In another embodiment, the invention is directed to a method of treating a patient suffering from an inflammatory condition comprising administering to the patient a therapeutically effective amount of a compound represented by Formula (III) or a pharmaceutically acceptable salt thereof.

In yet another embodiment, the invention is directed to a method of treating a patient suffering from an inflammatory condition comprising administering to the patient a therapeutically effective amount of a compound represented by Formula (IV) or a pharmaceutically acceptable salt thereof.

In an additional embodiment, the invention is directed to a method of treating a patient suffering from a CNS disorder comprising administering to the patient a therapeutically effective amount of a compound represented by Formula (I).

In another embodiment, the invention is directed to a method of treating a patient suffering from a CNS disorder comprising administering to the patient a therapeutically effective amount of a compound represented by Formula (II).

In an additional embodiment, the invention is directed to a method of treating a patient suffering from a CNS disorder comprising administering to the patient a therapeutically effective amount of a compound represented by Formula (III).

In yet another embodiment, the invention is directed to a method of treating a patient suffering from a CNS disorder comprising administering to the patient a therapeutically effective amount of a compound represented by Formula (IV).

DETAILED DESCRIPTION OF THE INVENTION

The present invention encompasses novel compounds, methods for the preparation thereof, pharmaceutical compositions and methods for the treatment of inflammatory disorders and CNS disorders. The compounds and methods of the invention are particularly useful for treatment of inflammatory conditions.

In one embodiment, the invention is a compound represented by Formula (I) or a pharmaceutically acceptable salt thereof. The variables of Formula (I) are as described above.

In another embodiment, the invention is a compound represented by the Formula (Ia):

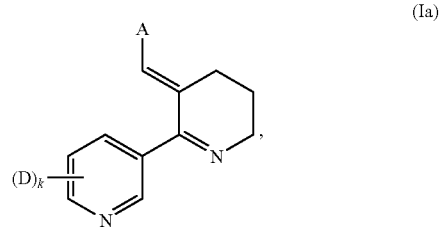

(Ia)

or a pharmaceutically acceptable salt thereof, wherein A is as defined above for Formula (I).

In one embodiment, when the compound has the Formula (I) or (Ia), A is $R_1$.

In another embodiment, when the compound has the Formula (I) or (Ia), D is independently selected from the group consisting of C1-C10 alkyl, C1-C10 alkyl substituted with one or more $R_8$, halo, haloalkyl, $OR_7$, $SR_7$, $NR_7R_7$, $C(O)OR_7$, $NO_2$ and CN.

In yet another embodiment, when the compound has the Formula (I) or (Ia), k is 0 or 1. In one embodiment, k is 0. In another embodiment, k is 1.

In another embodiment, when the compound has the Formula (I) or (Ia), $R_1$ is selected from the group consisting of:

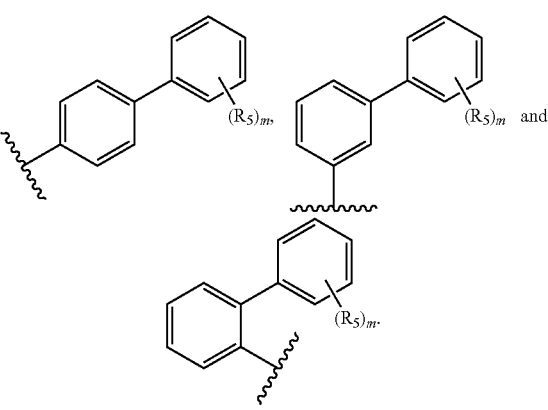

In one embodiment m is 0. In another embodiment, m is an integer from 1 to 6. In a further embodiment, m is an integer from 1 to 3.

In another embodiment, when the compound has the Formula (I) or (Ia), $R_1$ is selected from the group consisting of:

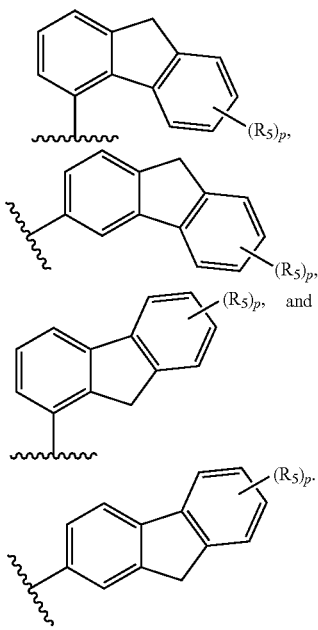

In one embodiment, p is 0. In another embodiment, p is an integer from 1 to 3. In an additional embodiment, $R_1$ is:

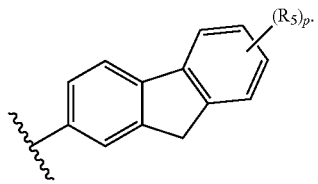

In another embodiment, when the compound has the Formula (I) or (Ia), $R_1$ is selected from the group consisting of:

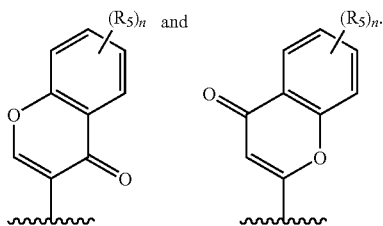

In one embodiment, n is 0. In another embodiment, n is an integer from 1-2.

In one embodiment, $R_5$ is selected from the group consisting of C1-C10 alkyl, C1-C10 alkyl substituted with one or more $R_8$, C2-C10 alkenyl, C2-C10 alkenyl substituted with one or more $R_8$, C2-C10 alkynyl, C2-C10 alkynyl substituted with one or more $R_8$, C3-C10 cycloalkyl, C3-C10 cycloalkyl substituted with one or more $R_9$, C4-C10 cycloalkenyl, C4-C10 cycloalkenyl substituted with one or more $R_9$, C5-C11 bicycloalkyl, C5-C11 bicycloalkyl substituted with one or more $R_9$, C5-C11 bicycloalkenyl, C5-C11 bicycloalkenyl substituted with one or more $R_9$, halo, $OR_7$, $SR_7$, $NR_7R_7$, $C(O)OR_7$, $NO_2$, CN, $C(O)R_7$, $C(O)C(O)R_7$, $C(O)NR_7R_7$, $N(R_7)C(O)R_7$, $NR_7S(O)_qR_7$, $N(R_7)C(O)OR_7$, $NR_7C(O)C(O)R_7$, $NR_7C(O)NR_7R_7$, $NR_7S(O)_qNR_7R_7$, $NR_7S(O)_qR_7$, $S(O)_qR_7$, $S(O)_qNR_7R_7$, $OC(O)R_7$ and aryl.

In another embodiment, $R_5$ is selected from the group consisting of C1-C10 alkyl, C1-C10 alkyl substituted with one or more $R_8$, halo, $OR_7$, $NR_7NR_7$, $C(O)OR_7$, $NO_2$ and CN. In another embodiment, $R_7$ is H, C1-C10 alkyl and C2-C10 alkenyl. In yet another embodiment, $R_8$ is halo, haloalkyl, $OR_7$, $NR_7R_7$, $NO_2$ and CN.

In an additional embodiment, $R_5$ is selected from the group consisting of halo, $CF_3$ and $OCF_3$.

In another embodiment, when the compound has the Formula (I) or (Ia), $R_1$ is selected from the group consisting of:

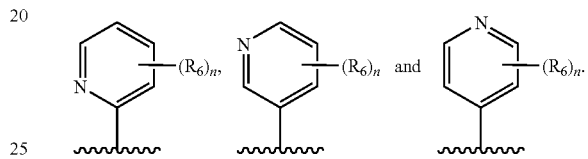

In one embodiment, $R_6$ is selected from the group consisting of C1-C10 alkyl, C1-C10 alkyl substituted with one or more $R_8$, halo, $OR_7$, $NR_7NR_7$, $C(O)OR_7$, $NO_2$ and CN. In another embodiment, $R_7$ is H, C1-C10 alkyl and C2-C10 alkenyl. In another embodiment $R_8$ is halo, haloalkyl, $CF_3$, $OCF_3$, $OR_7$, $NR_7R_7$, $NO_2$ and CN.

In a further embodiment, when the compound has the Formula (I) or (Ia), $R_1$ is:

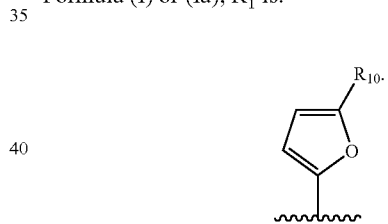

In one embodiment, $R_{10}$ is selected from the group consisting of 6 membered monocyclic aryl, 5 or 6 membered monocyclic heteroaryl comprising 1-3 heteroatoms, 8-12 membered bicyclic aryl, 8-12 membered bicyclic heteroaryl comprising 1-6 heteroatoms, 11-14 membered tricyclic aryl and 11-14 membered heteroaryl comprising 1-9 heteroatoms, wherein each of said heteroatoms is independently selected from the group consisting of O, N and S and wherein each of the aryl and heteroaryl are optionally substituted with one or more $R_{11}$.

In an additional embodiment, $R_{10}$ is a 6 membered monocyclic aryl wherein the aryl is optionally substituted with one or more $R_{11}$.

In yet another embodiment, $R_{10}$ is:

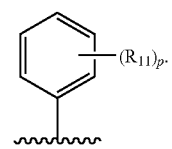

In yet another embodiment, there is an $R_{11}$ substitution at the 2-position of the phenyl ring. It is to be understood that when there is an $R_{11}$ substitution at the 2-position of the phenyl ring, there can be additional $R_{11}$ substitutions at any available carbon in the phenyl ring.

In one embodiment, $R_{10}$ is a 5 or 6 membered heteroaryl comprising one or more heteroatoms, wherein each of said heteroatoms is independently selected from O, S and N and wherein the heteroaryl is optionally substituted with one or more $R_{11}$. In a further embodiment, $R_9$ is thienyl, furyl or pyrrolyl, wherein each of said thienyl, furyl or pyrrolyl is optionally substituted with one or more $R_{11}$.

In a further embodiment, when the compound has the Formula (I) or (Ia), A is $R_2$, wherein $R_2$ is $R_3$—X—$R_4$. In one embodiment, $R_3$ is phenyl or pyridinyl, wherein the phenyl and pyridyl are optionally substituted with one or more $R_{11}$. In yet another embodiment, $R_4$ is aryl or heteroaryl, wherein each of the aryl or heteroaryl is optionally substituted with one or more $R_{11}$. In a further embodiment, X is O.

In an additional embodiment, $R_2$ is selected from the group consisting of:

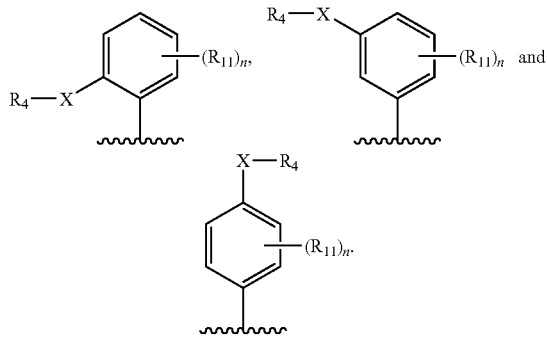

In yet another embodiment, $R_4$ is:

In yet another embodiment, $R_4$ is:

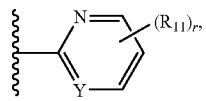

wherein Y is selected from the group consisting of CH, $CR_{11}$ and N; and r is an integer from 0 to 3.

In another embodiment, when the compound has the Formula (I) or (Ia), $R_5$ is selected from the group consisting of C1-C10 alkyl, C1-C10 alkyl substituted with one or more $R_8$, C2-C10 alkenyl, C2-C10 alkenyl substituted with one or more $R_8$, C2-C10 alkynyl, C2-C10 alkynyl substituted with one or more $R_8$, C3-C10 cycloalkyl, C3-C10 cycloalkyl substituted with one or more $R_9$, C4-C10 cycloalkenyl, C4-C10 cycloalkenyl substituted with one or more $R_9$, C5-C11 bicycloalkyl, C5-C11 bicycloalkyl substituted with one or more $R_9$, C5-C11 bicycloalkenyl, C5-C11 bicycloalkenyl substituted with one or more $R_9$, halo, $OR_7$, $SR_7$, $NR_7R_7$, $C(O)OR_7$, $NO_2$, CN, $C(O)R_7$, $C(O)C(O)R_7$, $C(O)NR_7R_7$, $N(R_7)C(O)R_7$, $NR_7S(O)_qR_7$, $N(R_7)C(O)OR_7$, $NR_7C(O)C(O)R_7$, $NR_7C(O)NR_7R_7$, $NR_7S(O)_qNR_7R_7$, $NR_7S(O)_qR_7$, $S(O)_qR_7$, $S(O)_qNR_7R_7$, $OC(O)R_7$, aryl and heteroaryl, wherein the aryl and heteroaryl are each optionally substituted with one or more $R_{11}$.

In an additional embodiment, $R_5$ is selected from the group consisting of C1-C10 alkyl, C1-C10 alkyl substituted with one or more $R_8$, C2-C10 alkenyl, C2-C10 alkenyl substituted with one or more $R_8$, C3-C10 cycloalkyl, C3-C10 cycloalkyl substituted with one or more $R_9$, halo, $OR_7$, $SR_7$, $NR_7R_7$, $C(O)OR_7$, $NO_2$, CN, $C(O)R_7$, $C(O)C(O)R_7$, $C(O)NR_7R_7$, $N(R_7)C(O)R_7$, $NR_7S(O)_qR_7$, $N(R_7)C(O)OR_7$, $NR_7C(O)C(O)R_7$, $NR_7C(O)NR_7R_7$, $NR_7S(O)_qNR_7R_7$, $NR_7S(O)_qR_7$, $S(O)_qR_7$, $S(O)_qNR_7R_7$ and $OC(O)R_7$.

In another embodiment, $R_5$ is selected from the group consisting of C1-C10 alkyl, C1-C10 alkyl substituted with one or more $R_8$, halo, $OR_7$, $NR_7R_7$, $SR_7$, $C(O)OR_7$, $NO_2$ and CN.

In one embodiment, $R_7$ is H, C1-C10 alkyl, C2-C10 alkenyl, C3-C10 cycloalkyl, haloalkyl, aryl and heteroaryl, where said aryl and heteroaryl are each optionally substituted with one or more $R_{11}$. In another embodiment, $R_8$ is halo, haloalkyl, $OR_7$, $NR_7R_7$, $C(O)R_7$, $OC(O)R_7$, $C(O)OR_7$, $NO_2$ and CN.

In another embodiment, $R_7$ is H, C1-C10 alkyl, C2-C10 alkenyl and haloalkyl. In yet another embodiment $R_8$ is halo, haloalkyl, $OR_7$, $NR_7R_7$, $SR_7$, $NO_2$ and CN.

In an additional embodiment, $R_{11}$ is selected from the group consisting of C1-C10 alkyl, C1-C10 alkyl substituted with one or more $R_8$, C2-C10 alkenyl, C2-C10 alkenyl substituted with one or more $R_8$, C3-C10 cycloalkyl, C3-C10 cycloalkyl substituted with one or more $R_9$, halo, $OR_7$, $SR_7$, $NR_7R_7$, $C(O)OR_7$, $NO_2$, CN, $C(O)R_7$, $C(O)C(O)R_7$, $C(O)NR_7R_7$, $N(R_7)C(O)R_7$, $NR_7S(O)_qR_7$, $N(R_7)C(O)OR_7$, $NR_7C(O)C(O)R_7$, $NR_7C(O)NR_7R_7$, $NR_7S(O)_qNR_7R_7$, $NR_7S(O)_qR_7$, $S(O)_qR_7$, $S(O)_qNR_7R_7$ and $OC(O)R_7$.

In an additional embodiment, $R_{11}$ is selected from the group consisting of C1-C10 alkyl, C1-C10 alkyl substituted with one or more $R_8$, halo, $OR_7$, $NR_7R_7$, $SR_7$, $C(O)OR_7$, $NO_2$ and CN.

In a further embodiment, the invention is a compound of Formula (II) or a pharmaceutically acceptable salt thereof. The variables of Formula (II) are as described above.

In one embodiment, the invention is a compound of the Formula (IIa):

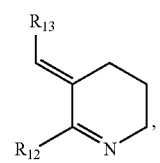

(IIa)

or a pharmaceutically acceptable salt thereof, wherein $R_{12}$ and $R_{13}$ are each as defined above for Formula (II).

In one embodiment, the compound has the Formula (II) or (IIa), $R_{12}$ is:

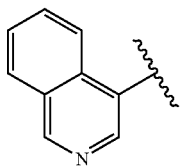

In another embodiment, the compound has the Formula (II) or (IIa), wherein $R_{12}$ is:

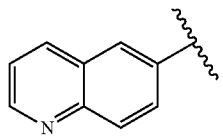

In one embodiment, the compound has the Formula (II) or (IIa), wherein $R_{13}$ is selected from the group consisting of 6 membered monocyclic aryl, 5 or 6 membered monocyclic heteroaryl, 8-12 membered bicyclic aryl and 8-12 membered bicyclic heteroaryl comprising 1-6 heteroatoms, wherein the aryl and heteroaryl are each optionally substituted with one or more $R_{17}$.

In another embodiment, the compound has the Formula (II) or (IIa), wherein $R_{13}$ is selected from the group consisting of 6 membered monocyclic aryl and 5 or 6 membered monocyclic heteroaryl, wherein the aryl and heteroaryl are each optionally substituted with one or more $R_{17}$.

In yet another embodiment, the compound has the Formula (II) or (IIa), wherein $R_{13}$ is:

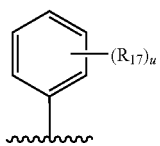

wherein u is an integer from 0 to 5.

In a further embodiment, the compound has the Formula (II) or (IIa) wherein $R_{13}$ is pyridinyl.

In one embodiment, $R_{17}$ is selected from the group consisting of C1-C10 alkyl, C1-C10 alkyl substituted with one or more $R_8$, C2-C10 alkenyl, C2-C10 alkenyl substituted with one or more $R_8$, C3-C10 cycloalkyl, C3-C10 cycloalkyl substituted with one or more $R_9$, halo, $OR_7$, $SR_7$, $NR_7R_7$, $C(O)OR_7$, $NO_2$, CN, $C(O)R_7$, $C(O)C(O)R_7$, $C(O)NR_7R_7$, $N(R_7)C(O)R_7$, $NR_7S(O)_qR_7$, $N(R_7)C(O)OR_7$, $NR_7C(O)C(O)R_7$, $NR_7C(O)NR_7R_7$, $NR_7S(O)_qNR_7R_7$, $NR_7S(O)_qR_7$, $S(O)_qR_7$, $S(O)_qNR_7R_7$ and $OC(O)R_7$.

In yet another embodiment, $R_{17}$ is selected from the group consisting of C1-C10 alkyl, C1-C10 alkyl substituted with one or more $R_8$, halo, $OR_7$, $NR_7R_7$, $SR_7$, $C(O)OR_7$, $NO_2$ and CN.

In another embodiment, the compound has the Formula (V):

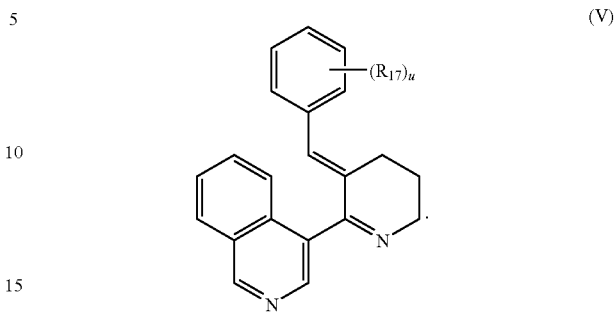

In yet another embodiment, the compound has the Formula (VI):

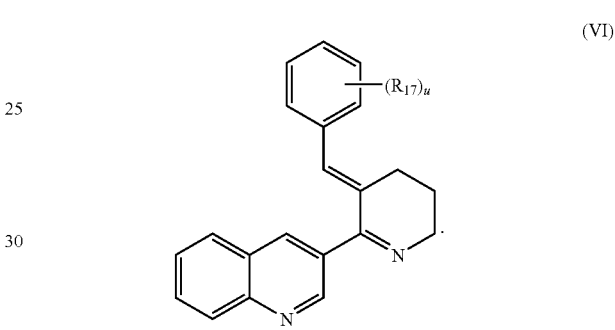

In another embodiment, the compound has the Formula (V) or (VI), wherein each $R_{17}$ is independently selected from the group consisting of C1-C10 alkyl, C1-C10 alkyl substituted with one or more $R_{15}$, halo, $CF_3$, $OCF_3$, $OR_{14}$, $NR_{14}NR_{14}$, $C(O)OR_{14}$, $NO_2$ and CN. In yet another embodiment, each $R_{14}$ is independently selected from the group consisting of H, C1-C10 alkyl and C2-C10 alkenyl. In additional embodiment, each $R_{15}$ is independently selected from the group consisting of halo, haloalkyl, $CF_3$, $OCF_3$, $OR_{14}$, $NR_{14}R_{14}$, $NO_2$ and CN; and u is an integer from 0 to 5.

Representative compounds of the invention include, but are not limited to, the following:

3-(3-(3-(4-chlorophenoxy)benzylidene)-3,4,5,6-tetrahydropyridin-2-yl)pyridine;
3-(3-(4-phenoxybenzylidene)-3,4,5,6-tetrahydropyridin-2-yl)pyridine;
3-(3-(3-phenoxybenzylidene)-3,4,5,6-tetrahydropyridin-2-yl)pyridine;
2-(4-((5,6-dihydro-2-(pyridin-3-yl)pyridin-3(4H)-ylidene)methyl)phenoxy)pyrimidine;
2-(3-((5,6-dihydro-2-(pyridin-3-yl)pyridin-3(4H)-ylidene)methyl)phenoxy)pyrimidine;
3-(3-(3-(4-methoxyphenoxy)benzylidene)-3,4,5,6-tetrahydropyridin-2-yl)pyridine;
3-(3-(3-(4-tert-butoxyphenoxy)benzylidene)-3,4,5,6-tetrahydropyridin-2-yl)pyridine;
3-(3-(3,5-dichlorophenoxy)benzylidene)-3,4,5,6-tetrahydropyridin-2-yl)pyridine;
3-(2-(pyridin-3-yl)-5,6-dihydropyridin-3(4H)-ylidene)methyl)-4H-chromen-4-one;
3-((5,6-dihydro-2-(pyridin-3-yl)pyridin-3(4H)-ylidene)methyl)-6-nitro-4H-chromen-4-one;

7-fluoro-3-((5,6-dihydro-2-(pyridin-3-yl)pyridin-3(4H)-ylidene)methyl)-6-nitro-4H-chromen-4-one;
3-((5,6-dihyrdo-2-(pyridin-3-yl)pyridin-3(4H)-ylidene)methyl)-7-methyl-4H-chrome-4-one;
7-chloro-3-((5,6-dihyrdo-2-(pyridin-3-yl)pyridin-3(4H)-ylidene)methyl)-6-methyl-4H-chromen-4-one;
3-(3-(biphenyl-4-ylmethylene)-3,4,5,6-tetrahydropyridin-2-yl)pyridine;
3-(3-((9H-fluoren-2-yl)methylene)-3,4,5,6-tetrahydropyridin-2-yl)pyridine;
3-(3-((2-fluorobiphenyl-4-yl)methylene)-3,4,5,6-tetrahydropyridin-2-yl)pyridine;
3-(3-((3-fluoro-4'-methoxybiphenyl-4-yl)methylene)-3,4,5,6-tetrahydropyridin-2-yl)pyridine;
3-(3-((3-fluoro-3'-methoxybiphenyl-4-yl)methylene)-3,4,5,6-tetrahydropyridin-2-yl)pyridine;
3-(3-((3-fluoro-3'-(trifluoromethoxy)biphenyl-4-yl)methylene)-3,4,5,6-tetrahydropyridin-2-yl)pyridine;
3-(3-(3-methoxy-4-(m-tolyloxy)benzylidene)-3,4,5,6-tetrahydropyridin-2-yl)pyridine;
3-(3-(3-methoxy-4-(4-methoxyphenoxy)benzylidene)-3,4,5,6-tetrahydropyridin-2-yl)pyridine;
3-(3-(2-methoxy-4-(m-tolyloxy)benzylidene)-3,4,5,6-tetrahydropyridin-2-yl)pyridine;
2-phenoxy-5-((2-(pyridin-3-yl)-5,6-dihydropyridin-3(4H)-ylidene)methyl)pyridine;
3-(3-((5-phenylfuran-2-yl)methylene)-3,4,5,6-tetrahydropyridin-2-yl)pyridine;
3-(3-((5-(4-chlorophenyl)furan-2-yl)methylene)-3,4,5,6-tetrahydropyridin-2-yl)pyridine;
3-(3-((5-(3-chlorophenyl)furan-2-yl)methylene)-3,4,5,6-tetrahydropyridin-2-yl)pyridine;
3-(3-((5-(2-chlorophenyl)furan-2-yl)methylene)-3,4,5,6-tetrahydropyridin-2-yl)pyridine;
3-(3-((5-(3,4-dichlorophenyl)furan-2-yl)methylene-3,4,5,6-tetrahydropyridin-2-yl)pyridine;
3-(3-(5-(2,5-dichlorophenyl)furan-2-yl)methylene)-3,4,5,6-tetrahydropyridin-2-yl)pyridine;
3-(3-(5-(3-chloro-4-methoxyphenyl)furan-2-yl)methylene)-3,4,5,6-tetrahydropyridin-2-yl)pyridine;
3-(3,4,5,6-tetrahydro-3-((5-(2-(trifluormethoxy)phenyl)furan-2-yl)methylene)pyridin-2-yl)pyridine;
3-(3,4,5,6-tetrahydro-3-((5-(4-(trifluormethoxy)phenyl)furan-2-yl)methylene)pyridin-2-yl)pyridine;
3-(3-((5-(2-(trifluoromethyl)phenyl)furan-2-yl)methylene)-3,4,5,6-tetrahydropyridin-2-yl)pyridine;
3-(3-((5-(3-(trifluoromethyl)phenyl)furan-2-yl)methylene)-3,4,5,6-tetrahydropyridin-2-yl)pyridine;
3-(3-((5-(2-chloro-5-(trifluoromethyl)phenyl)furan-2-yl)methylene)-3,4,5,6-tetrahydropyridin-2-yl)pyridine;
3-(3-((5-(2-chloro-4-(trifluoromethyl)phenyl)furan-2-yl)methylene)-3,4,5,6-tetrahydropyridin-2-yl)pyridine;
3-(3-((5-(3,5-bis(trifluoromethyl)phenyl)furan-2-yl)methylene-3,4,5,6-tetrahydropyridin-2-yl)pyridine;
3-(3-((5-(4-fluoro-3-(trifluoromethyl)phenyl)furan-2-yl)methylene-3,4,5,6-tetrahydropyridin-2-yl)pyridine;
4-(5-((2-(pyridin-3-yl)-5,6-dihydropyridin-3(4H)-ylidene)methyl)furan-2-yl)benzenesulfonamide dihydrochloride;
3-(3-((5-(3-fluoro-2-(trifluoromethyl)phenyl)furan-2-yl)methylene)-3,4,5,6-tetrahydropyridin-2-yl)pyridine dihydrochloride
3-(3,4,5,6-tetrahydro-3-((5-(2-nitrophenyl)furan-2-yl)methylene)pyridin-2-yl)pyridine;
3-(3,4,5,6-tetrahydro-3-((5-(3-nitrophenyl)furan-2-yl)methylene)pyridin-2-yl)pyridine;
3-(3-((5-(2,4-dichlorophenyl)furan-2-yl)methylene)-3,4,5,6-tetrahydropyridin-2-yl)pyridine;
3-(3-((5-(4-nitrophenyl)furan-2-yl)methylene)-3,4,5,6-tetrahydropyridin-2-yl)pyridine;
3-(3-((5-(4-chloro-2-nitrophenyl)furan-2-yl)methylene)-3,4,5,6-tetrahydropyridin-2-yl)pyridine;
3-(3-((5-(2,4-dimethoxyphenyl)furan-2-yl)methylene)-3,4,5,6-tetrahydropyridin-2-yl)pyridine;
3-(3-((5-(2-fluoro-3-(trifluoromethyl)phenyl)furan-2-yl)methylene)-3,4,5,6-tetrahydropyridin-2-yl)pyridine;
3-(3-((5-(2-fluorophenyl)furan-2-yl)methylene)-3,4,5,6-tetrahydropyridin-2-yl)pyridine;
3-(3-((5-(4-fluorophenyl)furan-2-yl)methylene)-3,4,5,6-tetrahydropyridin-2-yl)pyridine;
3-(3-((5-o-tolylfuran-2-yl)methylene)-3,4,5,6-tetrahydropyridin-2-yl)pyridine dihydrochloride;
1-phenyl-3-(4((2-(pyridin-3-yl)-5,6-dihydropyridin-3(4H)-ylidene)methyl)phenyl)urea;
1-(3,4-dichlorophenyl)-3-(4-((2-(pyridin-3-yl)-5,6-dihydropyridin-3(4H)-ylidene)methyl)phenyl)urea;
1-(3-methoxyphenyl)-3-(4-((2-(pyridin-3-yl)-5,6-dihydropyridin-3(4H)-ylidene)methyl)phenyl)urea;
4-(3-(2-fluoro-4-methoxybenzylidene)-3,4,5,6-tetrahydropyridin-2-yl)isoquinoline;
4-(3-(2,4-dimethoxybenzylidene)-3,4,5,6-tetrahydropyridin-2-yl)isoquinoline;
6-(3-(2,4-dimethoxybenzylidene)-3,4,5,6-tetrahydropyridin-2-yl)quinoline;
6-(3-((5-(2-chlorophenyl)furan-2-yl)methylene)-3,4,5,6-tetrahydropyridin-2-yl)quinoline;
6-(3-(2-fluoro-4-methoxybenzylidene)-3,4,5,6-tetrahydropyridin-2-yl)quinoline;
6-3,4,5,6-tetrahydro-3-((napthalen-1-yl)methylene)pyridin-2-quinoline;
3-(3-((2'-fluorobiphenyl-3-yl)methylene)-3,4,5,6-tetrahydropyridin-2-yl)pyridine;
3-(3-((2'-fluorobiphenyl-4-yl)methylene)-3,4,5,6-tetrahydropyridin-2-yl)pyridine;
3-(3-((2'-methoxybiphenyl-3-yl)methylene)-3,4,5,6-tetrahydropyridin-2-yl)pyridine;
3-(3-(biphenyl-2-ylmethylene)-3,4,5,6-tetrahydropyridin-2-yl)pyridine;
3-(3-((3'-(trifluoromethyl)biphenyl-3-yl)methylene)-3,4,5,6-tetrahydropyridin-2-yl)pyridine;
3-(3-((4'-(trifluoromethyl)biphenyl-3-yl)methylene)-3,4,5,6-tetrahydropyridin-2-yl)pyridine;
3-(3-((2'-fluorobiphenyl-2-yl)methylene)-3,4,5,6-tetrahydropyridin-2-yl)pyridine;
3-(3-((3'-methoxybiphenyl-4-yl)methylene)-3,4,5,6-tetrahydropyridin-2-yl)pyridine;
3-(3-((3'-fluorobiphenyl-2-yl)methylene)-3,4,5,6-tetrahydropyridin-2-yl)pyridine;
3-(3-((4'-fluorobiphenyl-3-yl)methylene)-3,4,5,6-tetrahydropyridin-2-yl)pyridine;
3-(3-((2',4'-difluorobiphenyl-3-yl)methylene)-3,4,5,6-tetrahydropyridin-2-yl)pyridine;
3-(3-((2'-chlorobiphenyl-3-yl)methylene)-3,4,5,6-tetrahydropyridin-2-yl)pyridine;
3-(3-((3'-chlorobiphenyl-3-yl)methylene)-3,4,5,6-tetrahydropyridin-2-yl)pyridine;
3-(3-((2'-isopropoxybiphenyl-3-yl)methylene)-3,4,5,6-tetrahydropyridin-2-yl)pyridine;
3-(3-((2'-(trifluoromethyl)biphenyl-3-yl)methylene)-3,4,5,6-tetrahydropyridin-2-yl)pyridine;
3-(3-((3'-(trifluoromethyl)biphenyl-3-yl)methylene)-3,4,5,6-tetrahydropyridin-2-yl)pyridine;
3-(3-((6-fluoro-2'-methoxybiphenyl-3-yl)methylene)-3,4,5,6-tetrahydropyridin-2-yl)pyridine;

3-(3-((6-fluoro-2'-methylbiphenyl-3-yl)methylene)-3,4,5,6-tetrahydropyridin-2-yl)pyridine;
3-(3-((2'-chloro-6-fluorobiphenyl-3-yl)methylene)-3,4,5,6-tetrahydropyridin-2-yl)pyridine;
3-(3-((3'-(trifluoromethoxy)biphenyl-3-yl)methylene)-3,4,5,6-tetrahydropyridin-2-yl)pyridine;
3-(3-((2',4'-dimethoxybiphenyl-3-yl)methylene)-3,4,5,6-tetrahydropyridin-2-yl)pyridine;
3-(3-((6-fluorobiphenyl-3-yl)methylene)-3,4,5,6-tetrahydropyridin-2-yl)pyridine;
3-(3-((6-fluoro-3'-methoxybiphenyl-3-yl)methylene)-3,4,5,6-tetrahydropyridin-2-yl)pyridine;
3-(3-((6-fluoro-3'-(trifluoromethoxy)biphenyl-3-yl)methylene)-3,4,5,6-tetrahydropyridin-2-yl)pyridine;
3-(3-((3',6-difluorobiphenyl-3-yl)methylene)-3,4,5,6-tetrahydropyridin-2-yl)pyridine;
3-(3-((2'-methylbiphenyl-3-yl)methylene)-3,4,5,6-tetrahydropyridin-2-yl)pyridine;
3-(3-((6-fluoro-2'-(trifluoromethyl)biphenyl-3-yl)methylene)-3,4,5,6-tetrahydropyridin-2-yl)pyridine;
3-(3-((2',6-difluorobiphenyl-3-yl)methylene)-3,4,5,6-tetrahydropyridin-2-yl)pyridine;
3-(3-((2'-(trifluoromethoxy)biphenyl-3-yl)methylene)-3,4,5,6-tetrahydropyridin-2-yl)pyridine;
N-(2'-fluoro-5'-((2-(pyridin-3-yl)-5,6-dihydropyridin-3(4H)-ylidene)methyl)biphenyl-3-yl)acetamide;
3-(3-((2',6-difluoro-3'-(trifluoromethyl)biphenyl-3-yl)methylene)-3,4,5,6-tetrahydropyridin-2-yl)pyridine;
3-(3-((6-fluoro-2'-phenoxybiphenyl-3-yl)methylene)-3,4,5,6-tetrahydropyridin-2-yl)pyridine;
3-(3-((6-methoxy-2'-phenoxybiphenyl-3-yl)methylene)-3,4,5,6-tetrahydropyridin-2-yl)pyridine;
3-(3-((2'-chloro-6-methoxybiphenyl-3-yl)methylene)-3,4,5,6-tetrahydropyridin-2-yl)pyridine;
3-(3-((2'-ethoxy-6-methoxybiphenyl-3-yl)methylene)-3,4,5,6-tetrahydropyridin-2-yl)pyridine;
3-(3-((2'-ethoxy-4-methoxybiphenyl-3-yl)methylene)-3,4,5,6-tetrahydropyridin-2-yl)pyridine;
3-(3-((2'-ethoxy-6'-fluoro-6-methoxybiphenyl-3-yl)methylene)-3,4,5,6-tetrahydropyridin-2-yl)pyridine;
3-(3-((2'-ethoxy-6'-fluoro-4-methoxybiphenyl-3-yl)methylene)-3,4,5,6-tetrahydropyridin-2-yl)pyridine;
3-(3-(biphenyl-3-ylmethylene)-3,4,5,6-tetrahydropyridin-2-yl)pyridine;
3-(3-((2'-ethoxy-6'-fluorobiphenyl-3-yl)methylene)-3,4,5,6-tetrahydropyridin-2-yl)pyridine;
3-(3-((6-methoxybiphenyl-3-yl)methylene)-3,4,5,6-tetrahydropyridin-2-yl)pyridine;
3-(3-((4'-chlorobiphenyl-3-yl)methylene)-3,4,5,6-tetrahydropyridin-2-yl)pyridine;
3-(3-((2'-fluoro-6-methoxybiphenyl-3-yl)methylene)-3,4,5,6-tetrahydropyridin-2-yl)pyridine;
3-(3-((3'-methoxybiphenyl-2-yl)methylene)-3,4,5,6-tetrahydropyridin-2-yl)pyridine;
3-(3-((5-methoxybiphenyl-2-yl)methylene)-3,4,5,6-tetrahydropyridin-2-yl)pyridine;
3-(3-((2',6-dimethoxybiphenyl-3-yl)methylene)-3,4,5,6-tetrahydropyridin-2-yl)pyridine;
3-(3-((6-methoxy-2'-(trifluoromethyl)biphenyl-3-yl)methylene)-3,4,5,6-tetrahydropyridin-2-yl)pyridine;
3-(3-((6-methoxy-2'-methylbiphenyl-3-yl)methylene)-3,4,5,6-tetrahydropyridin-2-yl)pyridine;
3-(3-((2'-ethoxybiphenyl-3-yl)methylene)-3,4,5,6-tetrahydropyridin-2-yl)pyridine;
3-(3-((6-fluorobiphenyl-3-yl)methylene)-3,4,5,6-tetrahydropyridin-2-yl)pyridine; and
3-(3-((2'-ethoxy-6-fluorobiphenyl-3-yl)methylene)-3,4,5,6-tetrahydropyridin-2-yl)pyridine.

Compounds were named using ChemDraw Ultra 9.0.1 (CambridgeSoft, Cambridge, Mass.).

The term "alkyl", as used herein, unless otherwise indicated, refers to both branched and straight-chain saturated aliphatic hydrocarbon groups having the specified number of carbon atoms; for example, "C1-C10 alkyl" denotes alkyl having 1 to 10 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term, "alkenyl", as used herein, refers to both straight and branched-chain moieties having the specified number of carbon atoms and having at least one carbon-carbon double bond.

The term, "alkynyl", as used herein, refers to both straight and branched-chain moieties having the specified number or carbon atoms and having at least one carbon-carbon triple bond.

The term "cycloalkyl," as used herein, refers to cyclic alkyl moieties having 3 or more carbon atoms. Examples of cycloalkyl include, but are not limited to cyclopropyl, cyclobutyl, cyclopentyl, cyclohexyl, and cycloheptyl.

The term "cycloalkenyl," as used herein, refers to cyclic alkenyl moieties having 3 or more carbon atoms.

The term "cycloalkynyl," as used herein, refers to cyclic alkynyl moieties having 5 or more carbon atoms.

The term "heterocycloalkyl" as used herein refers to cycloalkyl groups containing one or more heteroatoms (O, S, or N) within the ring.

The term "heterocycloalkenyl" as used herein refers to cycloalkenyl groups containing one or more heteroatoms (O, S or N) within the ring.

The term "bicycloalkyl" as used herein refers to a non-aromatic saturated carbocyclic group consisting of two rings. Examples of bicycloalkyl groups include, but are not limited to, bicyclo-[2.2.2]-octyl and norbornyl.

The term "bicycloalkenyl" as used herein refers to bicycloalkyl groups as defined above, except comprising one or more double bonds connecting carbon ring members (an "endocyclic double bond") and/or one or more double bonds connecting a carbon ring member and an adjacent non-ring carbon (an "exocyclic double bond").

The term "heterobicycloalkyl" as used herein refers to bicycloalkyl groups containing one or more heteroatoms (O, S or N) within a ring.

The term "heterobicycloalkenyl" as used herein refers to bicycloalkenyl groups containing one or more heteroatoms (O, S or N) within a ring.

Cycloalkyl, cycloalkenyl, bicycloalkyl, bicycloalkenyl, heterocycloalkyl, heterocycloalkyl, heterobicycloalkyl and heterobicycloalkenyl groups also include groups similar to those described above for each of these respective categories, but which are substituted with one or more oxo moieties.

The term "aryl", as used herein, refers to an aromatic carbocyclic group. An aryl group may be substituted or unsubstituted. Examples of aryl groups include, but are not limited to, phenyl and naphthyl. Each aryl group is optionally substituted with one or more substituents enumerated herein, which can be identical or different. A suitable substituent on an aryl is any substituent that does not substantially interfere with the pharmaceutical activity of the disclosed compound. Examples of suitable substituents for a substitutable carbon atom in an aryl group include, but are not limited to, C1-C10 alkyl, C1-C10 alkyl substituted with one or more $R_8$, C2-C10 alkenyl, C2-C10 alkenyl substituted with one or more $R_8$, C2-C10 alkynyl, C2-C10 alkynyl substituted with one or more $R_8$, C3-C10 cycloalkyl, C3-C10 cycloalkyl substituted with one or more $R_9$, C4-C10 cycloalkenyl, C4-C10 cycloalkenyl substituted with one or more $R_9$, 3-8 membered heterocycloalkyl, 3-8 membered heterocycloalkyl substituted with one or more $R_9$, 4-10 membered heterocycloalkenyl, 4-10 membered heterocycloalkenyl substituted with one or more $R_9$, C5-C11 bicycloalkyl, C5-C11 bicycloalkyl substituted with one or more $R_9$, C5-C11 bicycloalkenyl, C5-C11 bicycloalkenyl substituted with one or more $R_9$, 5-11 membered heterobicycloalkyl, 5-11 membered heterobicycloalkyl substituted with one or more $R_9$, 5-11 membered heterobicycloalkenyl, 5-11 membered heterobicycloalkenyl substituted with one or more $R_9$, halo, $OR_7$, $SR_7$, $NR_7R_7$, $C(O)OR_7$, $NO_2$, CN, $C(O)R_7$, $C(O)C(O)R_7$, $C(O)NR_7R_7$, $N(R_7)C(O)R_7$, $NR_7S(O)_qR_7$, $N(R_7)(C(O)OR_7)$, $NR_7C(O)C(O)R_7$, $NR_7C(O)NR_7R_7$, $NR_7S(O)_qNR_7R_7$, $NR_7S(O)_qR_7$, $S(O)_qR_7$, $S(O)_qNR_7R_7$, $OC(O)R_7$, optionally substituted aryl and optionally substituted heteroaryl.

The term "heteroaryl", as used herein, refers to aromatic carbocyclic groups containing one or more heteroatoms (O, S, or N) within a ring. A heteroaryl group can be monocyclic or polycyclic. A heteroaryl group may additionally be substituted or unsubstituted. The heteroaryl groups of this invention can also include ring systems substituted with one or more oxo moieties. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

The foregoing heteroaryl groups may also be C-attached or heteroatom-attached (where such is possible). For instance, a group derived from pyrrole may be pyrrol-1-yl (N-attached) or pyrrol-3-yl (C-attached).

Each heteroaryl group is optionally substituted with one or more substituents enumerated herein. A suitable substituent on a heteroaryl group is one that does not substantially interfere with the pharmaceutical activity of the disclosed compound. A heteroaryl may have one or more substituents, which can be identical or different. Examples of suitable substituents for a substitutable carbon atom in a heteroaryl group include, but are not limited to, C1-C10 alkyl, C1-C10 alkyl substituted with one or more $R_8$, C2-C10 alkenyl, C2-C10 alkenyl substituted with one or more $R_8$, C2-C10 alkynyl, C2-C10 alkynyl substituted with one or more $R_8$, C3-C10 cycloalkyl, C3-C10 cycloalkyl substituted with one or more $R_9$, C4-C10 cycloalkenyl, C4-C10 cycloalkenyl substituted with one or more $R_9$, 3-8 membered heterocycloalkyl, 3-8 membered heterocycloalkyl substituted with one or more $R_9$, 4-10 membered heterocycloalkenyl, 4-10 membered heterocycloalkenyl substituted with one or more $R_9$, C5-C11 bicycloalkyl, C5-C11 bicycloalkyl substituted with one or more $R_9$, C5-C11 bicycloalkenyl, C5-C11 bicycloalkenyl substituted with one or more $R_9$, 5-11 membered heterobicycloalkyl, 5-11 membered heterobicycloalkyl substituted with one or more $R_9$, 5-11 membered heterobicycloalkenyl, 5-11 membered heterobicycloalkenyl substituted with one or more $R_9$, halo, $OR_7$, $SR_7$, $NR_7R_7$, $C(O)OR_7$, $NO_2$, CN, $C(O)R_7$, $C(O)C(O)R_7$, $C(O)NR_7R_7$, $N(R_7)C(O)R_7$, $NR_7S(O)_qR_7$, $N(R_7)(C(O)OR_7)$, $NR_7C(O)C(O)R_7$, $NR_7C(O)NR_7R_7$, $NR_7S(O)_qNR_7R_7$, $NR_7S(O)_qR_7$, $S(O)_qR_7$, $S(O)_qNR_7R_7$, $OC(O)R_7$, optionally substituted aryl and optionally substituted heteroaryl.

The term "haloalkyl" as used herein refers to an alkyl group having 1 to (2n+1) subsituent(s) independently selected from F, Cl, Br or I, where n is the maximum number of carbon atoms in the alkyl group. Haloalkyl includes, for example, $CH_2F$, $CHF_2$ and $CF_3$.

The term "pyridinyl," as used herein is meant to encompass 2-pyridinyl, 3-pyridinyl and 4-pyridinyl groups. A pyridinyl may be substituted or unsubstituted.

As used herein, a "pharmaceutically acceptable salt" is an ionic bond-containing product of the reaction between the disclosed compound with either an acid or a base, suitable for administering to a subject. Pharmaceutically acceptable salts are well known in the art and are described, for example, in Berge et al (1977), Pharmaceutical Salts. Journal of Pharmaceutical Sciences, 69(1): 1-19, the contents of which are herein incorporated by reference. A non-limiting example of a pharmaceutically acceptable salt is an acid salt of a compound containing an amine or other basic group which can be obtained by reacting the compound with a suitable organic or inorganic acid, such as hydrogen chloride, hydrogen bromide, acetic acid, perchloric acid and the like. Examples of pharmaceutically acceptable salts also can be metallic salts including, but not limited to, sodium, magnesium, calcium, lithium and aluminum salts. Further examples of pharmaceutically acceptable salts include sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid. Salts can also be formed with suitable organic bases when the compound comprises an acid functional group such as —COOH or —$SO_3H$. Such bases suitable for the formation of a pharmaceutically acceptable base addition salts with compounds of the present invention include organic bases that are nontoxic and strong enough to react with the acid functional group. Such organic bases are well known in the art and include amino acids such as arginine and lysine, mono-, di-, and triethanolamine, choline, mono-, di-, and trialkylamine, such as methylamine, dimethylamine, and trimethylamine, guanidine, N-benzylphenethylamine, N-methylglucosamine, N-methylpiperazine, morpholine, ethylendiamine, tris(hydroxymethyl)aminomethane and the like.

In one embodiment, the invention pertains to a pharmaceutical composition comprising a pharmaceutically acceptable excipient and a compound disclosed herein. As used herein, a "pharmaceutical composition" is a formulation comprising a compound of the invention in a therapeutically effective amount and a pharmaceutically acceptable diluent or carrier, in a form suitable for administration to a subject. The pharmaceutical composition can be in bulk or in unit dosage form. The unit dosage form can be in any of a variety of forms, including, for example, a capsule, an IV bag, a tablet, a single pump on an aerosol inhaler, or a vial. The quantity of active ingredient (i.e., a formulation of the disclosed compound or salts thereof) in a unit dose of composition is an effective amount and may be varied according to the particular treatment involved. It may be appreciated that it may be necessary to make routine variations to the dosage depending on the age and condition of the patient. The dosage will also depend on the route of administration. A variety of routes are contemplated, including, but not limited to, parenteral, oral, pulmonary, ophthalmic, nasal, rectal, vaginal, aural, topical, buccal, transdermal, mucosal, intravenous, intramuscular, subcutaneous, intradermal, intraocular, intracerebral, intracerbroventricular, intralymphatic, intraarticular, intrathecal and intraperitoneal.

The compounds described herein can be used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein. Techniques for formulation and administration of the compounds of the instant invention can be found in *Remington: the Science and Practice of Pharmacy*, 19$^{th}$ edition, Mack Publishing Co., Easton, Pa. (1995).

In a further embodiment, the invention pertains to the treatment or alleviation of a condition mediated by the α7 nAChR. Conditions that are mediated by the α7 nAChR include, but are not limited to, an inflammatory condition, a CNS disorder, symptoms of nicotine withdrawal, cessation of smoking, treatment of chronic pain and treating a learning or memory impairment. As used herein, the "α7 nAChR," is a receptor comprising a α7 subunit. The receptor can comprise only the α7 subunit; alternatively the receptor comprises α7 subunit(s) and other nicotinic receptor subunit(s). In one embodiment, the receptor is a homopentamer of α7 subunits. In another embodiment, the receptor of is a heteropentamer of the α7 subunit and other nicotinic receptor subunits. An "α7 subunit" is intended to include all α7 subunit isoforms and/or variants including, but not limited to, the α7 duplicate nicotinic acetylcholine receptor ("dupα7") described in Villiger et al., Journal of Immunology 126: 86-98 (2002) and Gault et al., Genomics 52:173-85 (1998), the splice variant α7-2 described in US 20040152160 and the promoter variant(s) of the α7 nicotinic receptor described in U.S. Pat. No. 6,875,606.

In another embodiment, the invention pertains to the treatment of an inflammatory condition in a mammal suffering therefrom comprising administering a compound of formula (I). In yet another embodiment, the invention pertains to the treatment of an inflammatory condition in a mammal suffering therefrom comprising administering a compound of formula (II). In a further embodiment, the invention pertains to the treatment of an inflammatory condition in a mammal suffering therefrom comprising administering a compound of formula (III). In an additional embodiment, the invention pertains to the treatment of an inflammatory condition in a mammal suffering therefrom comprising administering a compound of formula (IV). In one embodiment, the inflammatory condition is selected from the group consisting of appendicitis, peptic, gastric or duodenal ulcers, peritonitis, pancreatitis, pseudomembranous colitis, acute colitis, ulcerative colitis, ischemic colitis, diverticulitis, epiglottitis, achalasia, cholangitis, cholecystitis, hepatitis, Crohn's disease, enteritis, ileus, Whipple's disease, asthma, chronic obstructive pulmonary disease, acute lung injury, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopic silicovolcanoconiosis, alvealitis, bronchiolitis, pharyngitis, pleurisy, sinusitis, influenza, respiratory syncytial virus, herpes, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, celiac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcet's syndrome, allograft rejection, graft-versus-host disease, Type I diabetes, ankylosing spondylitis, Berger's disease, Type II diabetes, Retier's syndrome and Hodgkins disease.

In another embodiment, the inflammatory condition is selected from the group consisting of rhinitis, cystic fibrosis, atherosclerosis, congestive heart failure, gout, peritonitis, pancreatitis, ulcerative colitis, Crohn's disease, asthma, acute lung injury, organ ischemia, reperfusion injury, sepsis, cachexia, burns, myocardial ischemia, adult respiratory distress syndrome, multiple sclerosis, rheumatoid arthritis, systemic lupus erythematous, chronic obstructive pulmonary disease, psoriasis, Behcet's syndrome, allograft rejection, graft-versus-host disease and ileus.

In yet another embodiment, the inflammatory condition is selected from the group consisting of peritonitis, pancreatitis, ulcerative colitis, Crohn's disease, asthma, acute lung injury, organ ischemia, reperfusion injury, sepsis, cachexia, burns, myocardial ischemia, adult respiratory distress syndrome, multiple sclerosis, rheumatoid arthritis, systemic lupus erythematous, chronic obstructive pulmonary disease, psoriasis, Behcet's syndrome, allograft rejection, graft-versus-host disease and ileus.

In a further embodiment, the inflammatory condition is selected from the group consisting of peritonitis, pancreatitis, ulcerative colitis, Crohn's disease, asthma, sepsis, adult respiratory distress syndrome, rheumatoid arthritis, systemic lupus erythematosus, chronic obstructive pulmonary disease, psoriasis and ileus.

In a further embodiment, the invention is directed to a method for inhibiting the release of a cytokine from a mammalian cell. As used herein, a cytokine is a soluble protein or peptide which is naturally produced by mammalian cells and which act in vivo as humoral regulators at micro- to picomolar concentrations. Cytokines can, either under normal or pathological conditions, modulate the functional activities of individual cells and tissues. A proinflammatory cytokine is a cytokine that is capable of causing any of the following physiological reactions associated with inflammation: vasodialation, hyperemia, increased permeability of vessels with associated edema, accumulation of granulocytes and mononuclear phagocytes, or deposition of fibrin. In some cases, the proinflammatory cytokine can also cause apoptosis, such as chronic heart failure, where tumor necrosis factor alpha (TNF-α) has been shown to stimulate cardiomyocyte apoptosis (Pulkki, 1997; Tsutsui et al. 2000). Nonlimiting examples of proinflammatory cytokines are TNF-α, interleukin (IL)-1α, IL-1B, 1L-6, IL-8, IL-18, interferon-γ (IFN-γ), high mobility group box 1 protein (HMGB1), platelet-activating factor (PAF), and macrophage migration inhibitory factor (MIF). In one embodiment, the invention is directed to a method for inhibiting the release of a cytokine from a mammalian cell, wherein the cytokine is selected from the group consisting of TNF-α, IL-1α, IL-1β, IL-6, IL-8, IL-18, IFN-γ, HMGB1, PAF and MIF. In yet another embodiment, the cytokine is selected from the group consisting of TNF-α, HMGB1, IL-1α, IL-1β, IL-6 and IL-18. In an additional embodiment, the cytokine is selected from the group consisting of TNF-α and HMGB1. Any mammalian cell that produces proinflammatory cytokines may be inhibited by the practice of the disclosed method. Nonlimiting examples are monocytes, macrophages, mast cells, neutrophils, epithelial cells, osteoblasts, fibroblasts, smooth muscle cells, and neurons. In one embodiment of the invention, the mammalian cell is selected from the group consisting of a monocyte, a macrophage and a neutrophil. In another embodiment, the mammalian cell is a macrophage.

In yet another embodiment, the invention is directed to a method for the treatment of a central nervous system (CNS) disorder in a mammal suffering therefrom comprising administering a compound of Formula (I) to the mammal. As used herein, the term "CNS disorder," includes neurological disorders, neuropsychiatric disorders, neurologic diseases, mental illnesses, neurodegenerative diseases, behavioral disorders, cognitive disorders and cognitive affective disorders. A CNS disorder can be drug induced, attributed to genetic predisposition, infection or trauma or can be of unknown etiology. In one embodiment, the CNS disorder is selected from the group consisting of dementia, Parkinson's disease, Huntington's chorea, tardive dyskinesia, hyperkinesia, mania, attention deficit disorder, anxiety, schizophrenia, Tourette's syndrome, manic depression, anxiety, Alzheimer's disease, learning deficit, cognitive deficit, memory loss, autism, amyotrophic lateral sclerosis and neuroendocrine disorders (e.g., obesity, bulemia and diabetes insipidus). In a further embodiment, the CNS disorder is Alzheimer's disease. In a preferred embodiment of the disclosed methods, the mammal is a human.

In a further embodiment, the CNS disorder is pain. The method of the invention can be used to treat acute, chronic or recurrent pain including, but not limited to, pain from migraine, postoperative pain, pain from chronic headache, and neuropathic pain.

As used herein, "treatment" and/or "treating" refer to the therapeutic treatment as well as prophylactic treatment or preventative measures. As used herein, an "effective amount" of a compound of the disclosed invention is the quantity which, when administered to a subject in need of treatment, improves the prognosis of the subject, e.g., delays or prevents the onset of and/or reduces the severity of one or more of the subject's symptoms associated with an inflammatory condition and/or a CNS disorder and/or a condition mediated by an α7 receptor. The amount of the disclosed compound to be administered to a subject will depend on the particular disease or condition, the mode of administration, and the characteristics of the subject, such as general health, other diseases, age, sex, genotype, body weight and tolerance to drugs. The skilled artisan will be able to determine appropriate dosages depending on these and other factors.

The disclosed compounds can be co-administered with one or more additional agents such as antibiotics, anti-inflammatory agents (e.g., ibuprofen, prednisone, corticosteroid, pentofylline), anti-fungals (e.g., Amphotericin B, Fluconazole, Ketoconazol and Itraconazol), steroids, decongestants, bronchodialators, and the like. The disclosed compounds can also be co-administered with anti-TNF agents, such as infliximab, etanercept, adalimumab, CDP870, CDP571, Lenercept or Thalidomide. The formulation may also contain preserving agents, solubilizing agents, chemical buffers, surfactants, emulsifiers, colorants, odorants and sweetenters. The disclosed compounds may be co-administered with one or more additional agents separately or in the same formulation.

The excipient included with the compounds of the pharmaceutical compositions of the invention is chosen based on the expected route of administration of the composition in therapeutic applications. The route of administration of the composition depends on the condition to be treated. For example, intravenous injection may be preferred for treatment of a systemic disorder such as endotoxic shock, and oral administration may be preferred to treat a gastrointestinal disorder such as a gastric ulcer. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. Thus, depending on the condition, the composition can be administered orally, parenterally, intranasally, vaginally, rectally, lingually, sublingually, bucally, intrabuccally and transdermally to the patient.

Accordingly, compositions designed for oral, lingual, sublingual, buccal and intrabuccal administration can be made without undue experimentation by means well known in the art, for example, with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, excipients, disintegrating agent, lubricants, glidants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like. For vaginal administration, a pharmaceutical composition may be presented as pessaries, tampons, creams, gels, pastes, foams, sprays or sponges.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the compound prepared by well-known methods to be administered, for example, as a nasal spray, nasal drop, suspension, gel, ointment, cream or powder. Administration of the composition may also take place using a nasal tampon or nasal sponge.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, or a cream formulation can be administer to a wound site.

The composition of the present invention can be administered parenterally such as, for example, by intravenous, intramuscular, intrathecal or subcutaneous injection. Parenteral administration can be accomplished by incorporating a composition of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, for purposes of the present invention, "pulmonary" will also mean to include a tissue or cavity that is contingent to the respiratory tract, in particular, the sinuses. For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the compound intended for pulmonary administration is dissolved, suspended or emulsified in a mixture of a solvent, surfactant and propellant. The mixture is maintained under pressure in a canister that has been sealed with a metering valve.

The practice of the present invention will employ, unless otherwise indicated, conventional techniques of cell culture, molecular biology, microbiology, cell biology, and immunology, which are well within the skill of the art. Such techniques are fully explained in the literature. See, e.g., Sambrook et al., 1989, "Molecular Cloning: A Laboratory Manual", Cold Spring Harbor Laboratory Press; Ausubel et al. (1995), "Short Protocols in Molecular Biology", John Wiley and Sons; Methods in Enzymology (several volumes); Methods in Cell Biology (several volumes), and Methods in Molecular Biology (several volumes).

Embodiments of the invention are illustrated by the following examples which are not intended to be limiting in any way.

EXEMPLIFICATION

General Experimental Methods

Air and moisture sensitive liquids and reagents were transferred via syringe and were introduced into glassware under a positive pressure of dry nitrogen through rubber septa. All reactions were stirred magnetically. Commercial reagents and solvents were used without further purification. Unless otherwise stated, the term "concentrated under reduced pressure" refers to the use of a Büchi rotary evaporator at 10-500 mbar. All temperatures are reported uncorrected in degrees Celsius (° C.). Thin-layer chromatography (TLC) was performed on EM Science pre-coated glass-backed silica gel 60 Å F-254 µm plates. Visualization of the plates was effected by one or more of the following techniques: (a) ultraviolet illumination, (b) exposure to iodine vapor, (c) immersion of the plate in a 10% solution of phosphomolybdic acid in ethanol followed by heating, (d) immersion of the plate in a cerium sulfate solution followed by heating, (e) immersion of the plate in an acidic ethanol solution of 2,4-dinitrophenylhydrazine followed by heating and/or (f) immersion of the plate in an acidic ethanol solution of anisaldehyde followed by heating. Column chromatography was performed on an Argonaut FlashMaster Personal or FlashMaster Personal$^+$ System using ISOLUTE Flash Si II silica gel pre-packed cartridges.

High performance liquid chromatography-electrospray mass spectra (LC-MS) were obtained using an Agilent 1100 Series HPLC equipped with a binary pump, a diode array detector monitored at 254 nm and 214 nm, an Agilent Zorbax Eclipse XDB-C8 (4.6 mm I.D.×150 mm, 5 micron) column, and an Agilent 1100 Series LC/MSD mass spectrometer with electrospray ionization. Spectra were scanned from 100-1000 amu. The eluant was a mixture of $H_2O$ (A) and MeCN (B) containing 0.1% AcOH. A typical gradient was:

| Time (min.) | % A | % B | Flow (mL/min.) |
| --- | --- | --- | --- |
| 0.00 | 90 | 10 | 1 |
| 9.00 | 10 | 90 | 1 |
| 9.50 | 90 | 10 | 1 |
| 12.00 | 90 | 10 | 1 |

Routine one-dimensional NMR spectroscopy was performed on a Varian 400 MHz spectrometer at 293 K. The samples were dissolved in deuterated solvents obtained from Cambridge Isotope Labs (Andover, Mass.). The chemical shifts were recorded on the ppm scale and were referenced to the appropriate residual solvent signal, such as 2.50 ppm for DMSO-$d_6$, 1.93 ppm for $CD_3CN$, 3.30 for $CD_3OD$, 5.32 ppm for $CD_2Cl_2$, and 7.26 ppm for $CDCl_3$ for $^1H$ NMR spectra, and 39.5 ppm for DMSO-$d_6$, 1.3 ppm for $CD_3CN$, 49.0 for $CD_3OD$, 53.8 ppm for $CD_2Cl_2$, and 77.0 ppm for $CDCl_3$ for $^{13}C$ NMR spectra.

Abbreviations and Acronyms

When the following abbreviations are used throughout the disclosure, they have the following meanings.

Ac acetyl
AcOH or HOAc acetic acid
aq aqueous
Boc t-butoxycarbonyl

Bu butyl
$^{13}$C Carbon-13
Cbz benzyloxycarbonyl
CDCl$_3$ deuterochloroform
CD$_2$Cl$_2$ deuteromethylene chloride
CD$_3$CN deuteroacetonitrile
CD$_3$OD dueteromethanol
Celite® registered trademark of Celite Corp. brand of diatomaceous earth
Cs$_2$CO$_3$ cesium carbonate
Cu(I)CN copper(I) cyanide
Cu(I)I copper(I) iodide
d doublet
dd doublet of doublet
DIAD diisopropyl azodicarboxylate
DIEA diisopropylethylamine
DMAP 4-(N,N-dimethyl)amino pyridine
DME dimethoxyethane
DMF N,N-dimethylformamide
DMSO dimethylsulfoxide
DMSO-d$_6$ dimethylsulfoxide-d$_6$
dppf 1,1'-bis(diphenylphosphino)ferrocene
dt doublet of triplet
EI electron impact ionization
ELMS electron impact—mass spectrometry
eq equivalent
Et ethyl
EtOH ethanol
Et$_2$O diethyl ether
EtOAc ethyl acetate
g gram(s)
h hour(s)
$^1$H proton
$^1$H NMR proton nuclear magnetic resonance
HCl hydrochloric acid
[HCl] concentrated hydrochloric acid
Hex hexanes
HNEt$_2$ diethylamine
HPLC high performance liquid chromatography
[H$_2$SO$_4$] concentrated sulfuric acid
Hz hertz
iPrOH isopropanol
K degrees Kelvin
LC-MS liquid chromatography—mass spectrometry
LDA lithium diisopropylamide
m multiplet
M molar
m/z mass over charge
[M+H]$^+$ mass of the molecular ion+hydrogen
Me methyl
MeOH methanol
MeCN acetonitrile
mg milligram(s)
MHz megahertz
min minute(s)
mL milliliter(s)
mol mole(s)
mmol millimole(s)
MS mass spectrometry
MtBE methyl tent-butyl ether
N normal
N$_2$ nitrogen gas
NMR nuclear magnetic resonance
Na$_2$CO$_3$ sodium carbonate
NaH sodium hydride
NaHCO$_3$ sodium hydrogen carbonate or sodium bicarbonate
NaOAc sodium acetate
NaOH sodium hydroxide
Na$_2$SO$_4$ sodium sulfate
NH$_4$Cl ammonium chloride
NH$_4$OH ammonium hydroxide
NMP N-methyl-2-pyrrolidone
Pd/C palladium on carbon
PdCl$_2$(dppf)-CH$_2$Cl$_2$ [1,1'-bis(diphenylphosphino)ferrocene]dichloropalladium (II) complex with dichloromethane (1:1)
Pd(PPh$_3$)$_4$ Tetrakis(triphenylphosphine)palladium(0)
Ph phenyl
PPh$_3$ triphenylphosphine
ppm parts per million
psi pounds per square inch
Pr propyl
q quartet
qt quintet
quant. quantitative
R$_f$ TLC retention factor
rt room temperature
RT HPLC retention time
s singlet
TBS tert-butyldimethylsilyl
TBSCl tert-butyldimethylsilyl chloride
TFA trifluoroacetic acid
THF tetrahydrofuran
THMD 2,2,6,6-tetramethyl-3,5-heptadione
° C. degrees Celsius
Δ reflux Example 1

Synthesis of 3-(3-(3-(4-chlorophenoxy)benzylidene)-3,4,5,6-tetrahydropyridin-2-yl)pyridine dihydrochloride

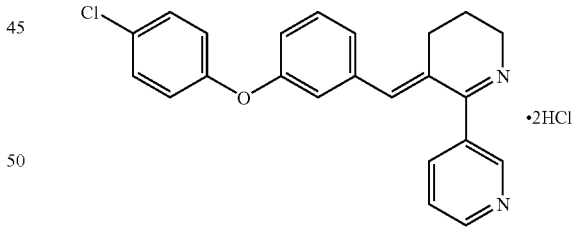

3-(5-Ammoniopentanoyl)pyridinium chloride (162 mg, 0.64 mmol) was suspended in a reaction vessel with i-propanol (12 mL). 3-(4-chlorophenoxy)benzaldehyde (225 mg, 0.97 mmol) was then added and the reaction vessel sealed. The reaction was heated to 80° C. overnight and then cooled to room temperature. The precipitate was recovered by vacuum filtration, washed with a 20% i-propanol in hexane solution then dried under vacuum giving 161 mg (56%) of a tan-colored solid. LC-MS: RT=6.22 min, [M+H]$^+$=375.1.

The compounds shown in Table 1 were prepared by similar methods as described for Example 1, substituting the appropriate aldehyde. The compounds below were isolated as dihydrochloride salts unless otherwise noted.

TABLE 1

[Structure: benzylidene-tetrahydropyridine with 3-pyridyl substituent; aromatic ring bears Ra, Rb, Rc substituents]

| Example | Ra | Rb | Rc | Yield | LC RT | MS [M + H]+ |
|---|---|---|---|---|---|---|
| 2 | H | —O-phenyl | H | 41% | 5.78 min | 341.0 |
| 3 | —O-phenyl | H | H | 77% | 5.85 min | 341.1 |
| 4 | H | —O-(pyrimidin-2-yl) | H | 65% | 3.89 min | 343.1 |
| 5 | —O-(pyrimidin-2-yl) | H | H | 78% | 4.02 min | 343.1 |
| 6 | —O-(4-methoxyphenyl) | H | H | 71% | 5.72 min | 371.1 |
| 7 | —O-(4-tert-butoxyphenyl) | H | H | 51% | 7.18 min | 397.2 |
| 8 | —O-(3,5-dichlorophenyl) | H | H | 44% | 6.84 min | 409.1 |
| 9 | 2-fluorophenyl | H | H | 49% | 5.85 min | 343.0 |
| 10 | H | 2-fluorophenyl | H | 52% | 5.89 min | 343.0 |

TABLE 1-continued

| Example | R$_a$ | R$_b$ | Rc | Yield | LC RT | MS [M + H]$^+$ |
|---|---|---|---|---|---|---|
| 11 | 2-methoxyphenyl | H | H | 42% | 5.54 min | 355.6 |
| 12 | H | H | Ph | 81% | 5.28 min | 325.5 |
| 13 | 3-(trifluoromethyl)phenyl | H | H | 53% | 6.19 min | 393.6 |
| 14 | 4-(trifluoromethyl)phenyl | H | H | 60% | 6.17 min | 393.6 |
| 15 | H | H | 2-fluorophenyl | 53% | 5.37 min | 343.5 |
| 16 | H | 3-methoxyphenyl | H | 57% | 5.51 min | 355.6 |
| 17 | H | H | 3-fluorophenyl | 44% | 5.39 min | 343.5 |
| 18 | 4-fluorophenyl | H | H | 54% | 5.62 min | 343.5 |
| 19 | 2,4-difluorophenyl | H | H | 70% | 5.81 min | 361.6 |

Example 20

Synthesis of 3-((2-(pyridin-3-yl)-5,6-dihydropyridin-3(4H)-ylidene)methyl)-4H-chromen-4-one dihydrochloride

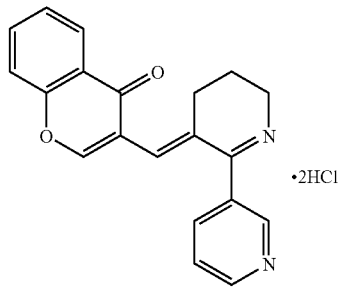

3-(5-Ammoniopentanoyl)pyridinium chloride (219 mg, 0.87 mmol) and 3-formylchromone (228 mg, 1.31 mmol) were combined and suspended in a reaction vessel with i-propanol (30 mL). The reaction vessel was sealed and the reaction heated to 85° C. overnight then cooled to room temperature. The precipitate was recovered by vacuum filtration, washed with a 20% i-propanol in hexane solution, then dried under vacuum giving 245 mg (72%) of a powdery brown solid. LC-MS: RT=4.20 min, [M+H]$^+$=317.1.

The compounds shown in Table 2 were prepared as described in Example 9, substituting the appropriate reactant. The compounds below were isolated as dihydrochloride salts unless otherwise noted.

TABLE 2

| Example | $R_c$ | $R_d$ | Yield | LC RT | MS [M + H]$^+$ |
|---|---|---|---|---|---|
| 21 | —NO$_2$ | —H | 90% | 4.41 min | 362.1 |
| 22 | —F | —H | 90% | 4.32 min | 335.1 |
| 23 | —CH$_3$ | —H | 68% | 4.53 min | 331.1 |
| 24 | —Cl | —CH$_3$ | 60% | 5.19 min | 365.0 |

Example 25

Synthesis of 3-(3-(biphenyl-4-ylmethylene)-3,4,5,6-tetrahydropyridin-2-yl)pyridine dihydrochloride

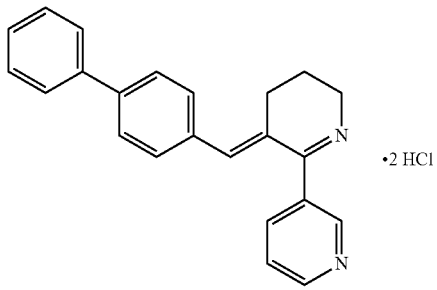

3-(5-Ammoniopentanoyl)pyridinium chloride (128 mg, 0.51 mmol) was suspended in methanol (2 mL) and treated with N,N-diisopropylethylamine (165 mg, 1.27 mmol) in a reaction vessel. This gave a clear solution. A dual solution of 0.6 M acetic acid and 0.3 M sodium acetate in methanol (10 mL) was then added, followed by addition of 4-phenylbenzaldehyde (140 mg, 0.76 mmol). The reaction vessel was then sealed and the reaction heated to 80° C. overnight then cooled to room temperature. The reaction mixture was then concentrated under reduced pressure, treated with a saturated solution of NaHCO$_{3(aq)}$, and extracted three times with EtOAc. The EtOAc extracts were washed with brine, then combined, dried over Na$_2$SO$_4$, filtered and concentrated under reduced pressure. The recovered material was eluted through a 20 gram column of silica gel with 7:7:7:1:0.1 hexane:MtBE:CH$_2$Cl$_2$:MeOH:NH$_4$OH eluant. One sample was recovered and dried under vacuum. This sample was then dissolved into MeOH and treated with two equivalents of 6 N HCl$_{(aq)}$, concentrated under reduced pressure and re-crystallized from isopropanol giving 80 mg (39%) of yellow needles. LC-MS: RT=5.72 min, [M+H]$^+$=325.1.

Example 26

Synthesis of 3-(3-((9H-fluoren-2-yl)methylene)-3,4,5,6-tetrahydropyridin-2-yl)pyridine dihydrochloride

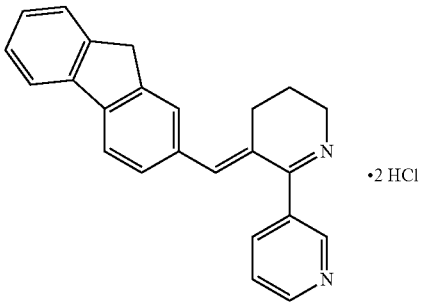

3-(5-Ammoniopentanoyl)pyridinium chloride (122 mg, 0.48 mmol) was suspended in methanol (2 mL) and treated with N,N-diisopropylethylamine (157 mg, 1.21 mmol) in a reaction vessel. This gave a clear solution. A dual solution of 0.6 M acetic acid and 0.3 M sodium acetate in methanol (10 mL) was then added, followed by addition of fluorine-2-carboxaldehyde (140 mg, 0.72 mmol). The reaction vessel was then sealed and the reaction heated to 80° C. overnight, then cooled to room temperature. The reaction mixture was partially concentrated under reduced pressure, treated with a saturated solution of NaHCO$_3$ (aq), and extracted three times with EtOAc. The EtOAc extracts were washed with brine, then combined, dried over Na$_2$SO$_4$, filtered and concentrated under reduced pressure. The recovered material was eluted through a 20 gram column of silica gel with 7:7:7:1:0.1 hexane:MtBE:CH$_2$Cl$_2$:MeOH:NH$_4$OH (430 mL), then with 96:4:0.4 CH$_2$Cl$_2$: MeOH:NH$_4$OH (250 mL). One sample was recovered and dried under vacuum. This sample was then dissolved into MeOH and treated with two equivalents of 6 NHCl$_{(aq)}$, concentrated under reduced pressure and re-crystallized from isopropanol giving 42 mg (21%) of orange crystals. LC-MS: RT=5.70 min, [M+H]$^+$=337.0.

Example 27

Synthesis of 3-(3-((2-fluorobiphenyl-4-yl)methylene)-3,4,5,6-tetrahydropyridin-2-yl)pyridine dihydrochloride

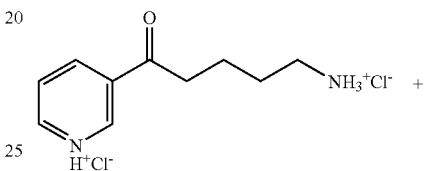

3-(5-Ammoniopentanoyl)pyridinium chloride (150 mg, 0.60 mmol) and 2-fluorobiphenyl-4-carboxaldehyde (155 mg, 0.78 mmol) were combined in a reaction vessel and treated with ethanol (10 mL) and concentrated HCl$_{(aq)}$ (5 drops). The vessel was then sealed and the reaction was heated to 85° C. overnight then cooled to room temperature. The reaction mixture was then concentrated under reduced pressure then partially dissolved into hot isopropanol. This mixture was left to cool and crystals formed. The crystals were recovered by vacuum filtration, washed with fresh isopropanol, and dried under vacuum giving 92 mg (36%) of a yellow solid. LC-MS: RT=5.88 min, [M+H]$^+$=343.1.

Example 28

Synthesis of 3-(3-((3-fluoro-4'-methoxybiphenyl-4-yl)methylene)-3,4,5,6-tetrahydropyridin-2-yl)pyridine dihydrochloride The synthesis of 3-(3-((3-fluoro-4'-methoxybiphenyl-4-yl)methylene)-3,4,5,6-tetrahydropyridin-2-yl)pyridine dihydrochloride is depicted below.

A. Step 1: Preparation of Intermediate 1

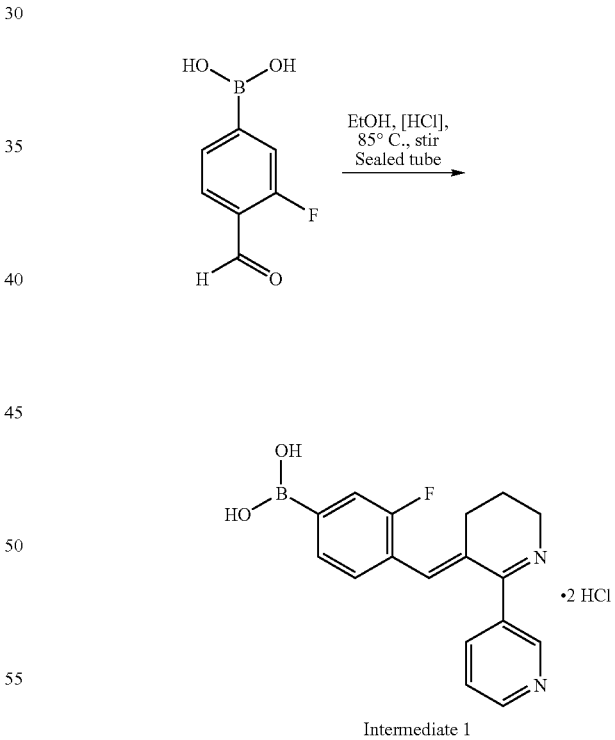

Intermediate 1

3-(5-Ammoniopentanoyl)pyridinium chloride (104 mg, 0.41 mmol) was suspended in ethanol (10 mL) in a reaction vessel. Five drops of concentrated hydrochloric acid was added, followed by the addition of 3-fluoro-4-formylphenylboronic acid (76 mg, 0.46 mmol). The reaction vessel was sealed, and the reaction was heated to 85° C. with stirring overnight. The reaction was then cooled to room temperature and concentrated under reduced pressure. The recovered material was then immediately taken on to the next second step without further purification.

B. Step 2: Preparation of 3-(3-((3-fluoro-4'-methoxy-biphenyl-4-yl)methylene)-3,4,5,6-tetrahydropyridin-2-yl)pyridine dihydrochloride

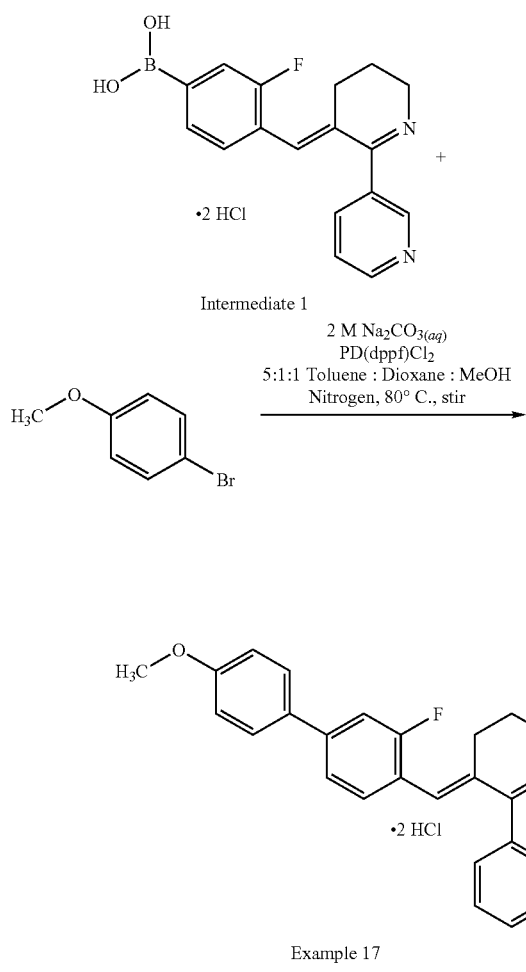

Intermediate 1

Example 17

Intermediate 1 was dissolved into a mixture of toluene (10 mL), methanol (2 mL), and dioxane (2 mL). The 2 M Na$_2$CO$_{3(aq)}$ solution (2.0 mL, 4 mmol) was then added, followed by the addition of the 4-bromoanisole (230 mg, 1.23 mmol) and the dichloro[1,1'-bis(diphenylphosphino)ferrocene]palladium (II) dichloromethane adduct catalyst (29 mg, 0.04 mmol). The reaction vessel was then flushed with nitrogen and sealed. The reaction was then heated to 80° C. with stirring overnight. The reaction was then cooled to room temperature and quenched with saturated NH$_4$Cl$_{(aq)}$ and extracted three times with EtOAc. The EtOAc extracts were then washed with brine, combined, dried over Na$_2$SO$_4$, filtered and concentrated under reduced pressure. This gave a black oil that was eluted through a 20 gram column of silica gel with 7:7:7:1:0.1 hexane: MtBE:CH$_2$Cl$_2$:MeOH:NH$_4$OH (660 mL). One sample was recovered that was dissolved into isopropanol and treated with 2 equivalents of 6 NHCl$_{(aq)}$. This solution was then diluted with ether which caused a precipitate to form. This precipitate was recovered by vacuum filtration, washed with ether and dried under vacuum giving 81 mg (44%) of a brown solid. LC-MS: RT=5.90 min, [M+H]$^+$=373.1.

Example 29

Synthesis of 3-(3-((3-fluoro-3'-methoxybiphenyl-4-yl)methylene)-3,4,5,6-tetrahydropyridin-2-yl)pyridine dihydrochloride The preparation of 3-(3-((3-fluoro-3'-methoxybiphenyl-4-yl)methylene)-3,4,5,6-tetrahydropyridin-2-yl)pyridine dihydrochloride is shown below.

A. Step 1: Preparation of Intermediate 2

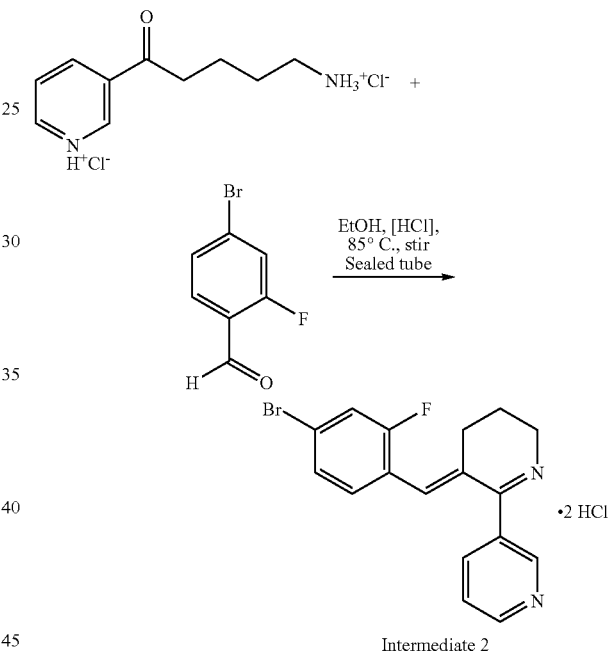

Intermediate 2

3-(5-Ammoniopentanoyl)pyridinium chloride (307 mg, 1.22 mmol) and 4-bromo-2-fluorobenzaldehyde (619 mg, 3.05 mmol) were combined in a reaction vessel and treated with ethanol (24 mL) and concentrated hydrochloric acid (5 drops). The reaction vessel was sealed and the reaction was heated to 85° C. with stirring. When no further reaction was observed by HPLC/MS, the reaction was cooled to room temperature and concentrated under reduced pressure. The recovered material was treated with a saturated solution of NaHCO$_{3(aq)}$, and extracted three times with EtOAc. The EtOAc extracts were washed with brine, then combined, dried over Na$_2$SO$_4$, filtered and concentrated under reduced pressure. The recovered material was eluted through a 20 gram column of silica gel with 98:2:0.2 CH$_2$Cl$_2$:MeOH: NH$_4$OH (1 liter). One sample was recovered and dried under vacuum. This sample was then re-crystallized from isopropanol giving 81 mg (19%) of white needles. LC-MS: RT=5.33 min, [M+H]$^+$=347.0. The mother liquor from the crystallization contained 144 mg (34%) of the mass balance as a clear brown film. The material from the mother liquor was taken on to the second step.

B. Step 2: Preparation of 3-(3-((3-fluoro-3'-methoxy-biphenyl-4-yl)methylene)-3,4,5,6-tetrahydropyridin-2-yl)pyridine dihydrochloride

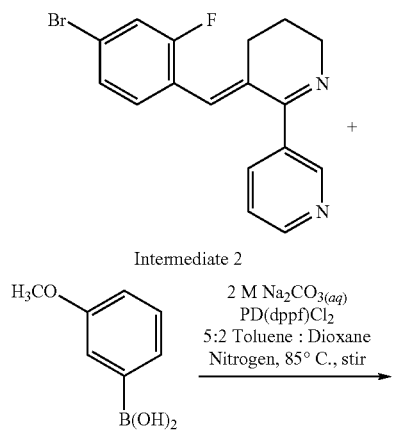

Intermediate 2 (144 mg, 0.42 mmol) was dissolved into toluene (12 mL) and dioxane (2.5 mL) in a reaction vessel. 3-Methoxybenzeneboronic acid (127 mg, 0.84 mmol) and the 2 M $Na_2CO_{3(aq)}$ solution (2.1 mL, 4.2 mmol) were added, followed by addition of dichloro[1,1'-bis(diphenylphosphino)ferrocene]palladium (II) dichloromethane adduct catalyst (31 mg, 0.04 mmol). The reaction vessel was then flushed with nitrogen and sealed. The reaction was then heated to 85° C. with stirring overnight. The reaction was then cooled to room temperature and quenched with water and extracted three times with EtOAc. The EtOAc extracts were then washed with brine, combined, dried over $Na_2SO_4$, filtered and concentrated under reduced pressure, and eluted through a 20 gram column of silica gel with 99:1:0.1 $CH_2Cl_2$: MeOH: NHOH (1 liter). One sample was recovered that was dissolved into methanol and treated with 2 equivalents of 6 N $HCl_{aq}$). This solution was then concentrated under reduced pressure and the recovered material dissolved into hot isopropanol to recrystallize. The crystals formed were recovered by vacuum filtration, washed with a 10% isopropanol in hexane solution, then dried under vacuum giving 91 mg (48%) of a brown solid. LC-MS: RT=6.03 min, $[M+H]^+$=373.1.

Example 30

Synthesis of 3-(3-((3-fluoro-3'-(trifluoromethoxy)biphenyl-4-yl)methylene)-3,4,5,6-tetrahydropyridin-2-yl)pyridine dihydrochloride

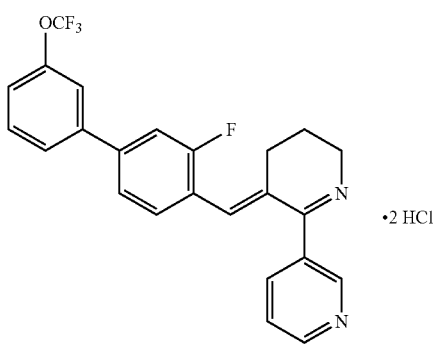

3-(3-((3-fluoro-3'-(trifluoromethoxy)biphenyl-4-yl)methylene)-3,4,5,6-tetrahydropyridin-2-yl)pyridine dihydrochloride was prepared from Intermediate 2 using the appropriate boronic acid as described for Example 18 giving 50 mg (23%) of a yellow solid. LC-MS: RT=6.99 min, $[M+H]^+$=427.1.

Example 31

Synthesis of 3-(3-(3-methoxy-4-(m-tolyloxy)benzylidene)-3,4,5,6-tetrahydropyridin-2-yl)pyridine dihydrochloride The preparation of 3-(3-(3-methoxy-4-(m-tolyloxy)benzylidene)-3,4,5,6-tetrahydropyridin-2-yl)pyridine dihydrochloride is described below.

A. Step 1: Preparation of Intermediate 3

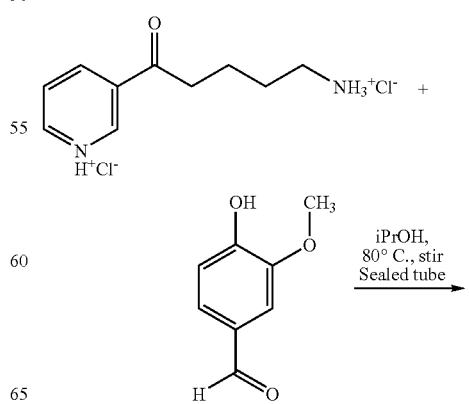

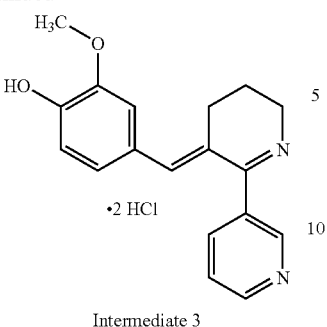

Intermediate 3

3-(5-Ammoniopentanoyl)pyridinium chloride (518 mg, 2.1 mmol) and vanillin (471 mg, 3.1 mmol) were combined in a reaction vessel and treated with isopropanol (50 mL). The reaction vessel was sealed and the reaction was heated to 80° C. with stirring overnight. The reaction was then cooled to room temperature and the precipitate recovered by vacuum filtration and washed with a 20% solution of isopropanol in hexane. The recovered solid was then dried under vacuum giving 740 mg (95%) of a yellow solid. LC-MS: RT=3.70 min, [M+H]$^+$=295.1.

B. Step 2: Preparation of 3-(3-(3-methoxy-4-(m-tolyloxy)benzylidene)-3,4,5,6-tetrahydropyridin-2-yl)pyridine dihydrochloride

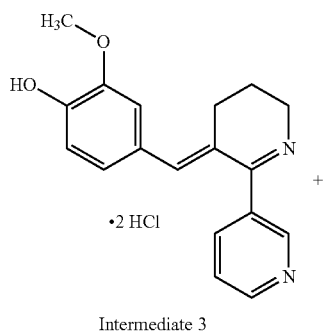

Intermediate 3

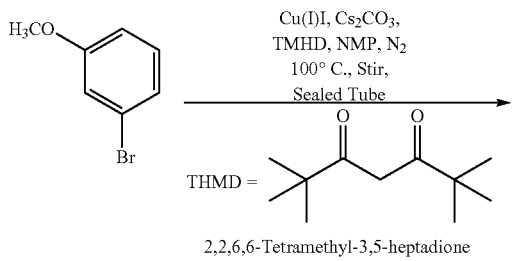

2,2,6,6-Tetramethyl-3,5-heptadione

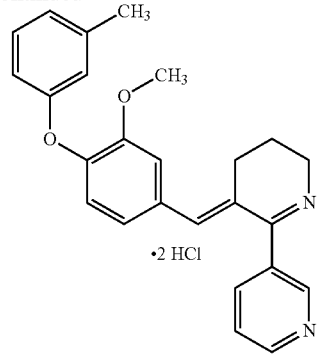

Example 20

3-(3-(3-methoxy-4-(m-tolyloxy)benzylidene)-3,4,5,6-tetrahydropyridin-2-yl)pyridine dihydrochloride was prepared as described in Buck et al. *Org. Lett.*, 2002, (4), 9, 1623-1626.

Briefly, Intermediate 3 (60 mg, 0.16 mmol), copper (I) iodide (15 mg, 0.08 mmol), cesium carbonate (169 mg, 0.48 mmol) and 3-bromotoluene (112 mg, 0.64 mmol) were combined in a reaction vessel and treated with NMP (2 mL). 2,2,6,6-Tetramethyl-3,5-heptadione (29 mg, 0.16 mmol) was then added. The reaction vessel was then flushed with nitrogen gas and sealed, and the reaction was heated to 100° C. with stirring for two days. The reaction was then cooled to room temperature and quenched with concentrated ammonium hydroxide. This mixture was then extracted three times with EtOAc. The EtOAc extracts were washed with brine, combined, dried over Na$_2$SO$_4$, filtered and concentrated under reduced pressure. This gave a black oil that was eluted through a 20 gram column of silica gel with CH$_2$Cl$_2$ (100 mL) and then with 10.5:7:7:1:0.1 hexane:MtBE:CH$_2$Cl$_2$:MeOH: NH$_4$OH (800 mL). One sample was recovered that was dissolved into methanol and treated with 2 equivalents of 6 N HCl$_{(aq)}$. This solution was concentrated under reduced pressure, and the recovered material re-crystallized from a mix of isopropanol and ether. The crystals were recovered by vacuum filtration, washed with 20% isopropanol in hexane, then dried under vacuum giving 32 mg (38%) of a yellow solid. LC-MS: RT=5.88 min, [M+H]$^+$=385.1.

Example 32

Synthesis of 3-(3-(3-methoxy-4-(4-methoxyphenoxy)benzylidene)-3,4,5,6-tetrahydropyridin-2-yl)pyridine dihydrochloride

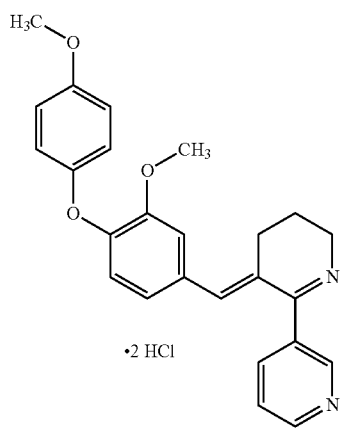

Intermediate 3 (80 mg, 0.22 mmol), copper (I) iodide (excess), cesium carbonate (233 mg, 0.66 mmol), 2,2,6,6-tetramethyl-3,5-heptadione (88 mg, 0.48 mmol) and p-bromoanisole (82 mg, 0.44 mmol) were combined in NMP (5 mL) under nitrogen in a reaction vessel. The reaction vessel was sealed and the reaction was heated to 110° C. with stirring for three days. The reaction was then cooled to room temperature and quenched with saturated $NH_4Cl_{(aq)}$ and saturated $NaHCO_{3(aq)}$. This mixture was then extracted three times with EtOAc. The EtOAc extracts were washed with brine, combined, dried over $Na_2SO_4$, filtered and concentrated under reduced pressure. This gave a black oil that was eluted through a 20 gram column of silica gel with $CH_2Cl_2$ (100 mL) and then with 10.5:7:7:1:0.1 (510 mL) and then with 7:7:7:1:0.1 (440 mL) hexane:MtBE:$CH_2Cl_2$:MeOH:$NH_4OH$ (step gradient). Two impure samples were recovered. The purer sample as determined by HPLC/MS was dissolved into MeOH and treated with two equivalents of 6 N $HCl_{(aq)}$, then concentrated under reduced pressure. The recovered material was dissolved into hot isopropanol, cooled to room temperature then treated with ether until a precipitate formed. This precipitate was recovered by vacuum filtration, washed with fresh ether, then dried under vacuum giving 6 mg (5.7%) of a yellow solid. LC-MS: RT=5.59 min, $[M+H]^+=401.0$.

Example 33

Synthesis of 3-(3-(2-methoxy-4-(m-tolyloxy)benzylidene)-3,4,5,6-tetrahydropyridin-2-yl)pyridine dihydrochloride The preparation of 3-(3-(2-methoxy-4-(m-tolyloxy)benzylidene)-3,4,5,6-tetrahydropyridin-2-yl)pyridine dihydrochloride is described below.

A. Step 1: Preparation of Intermediate 4

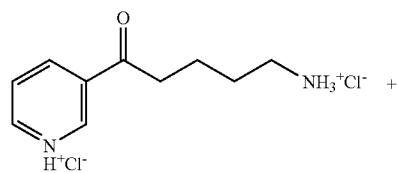

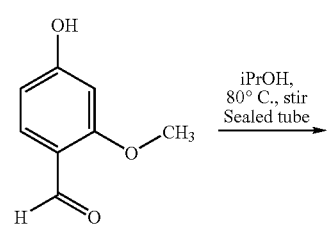

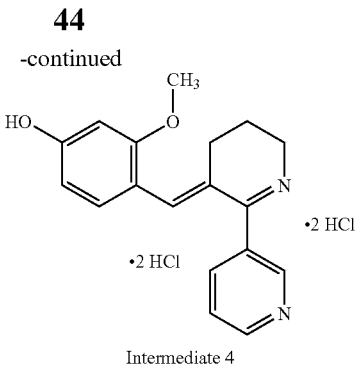

Intermediate 4

3-(5-Ammoniopentanoyl)pyridinium chloride (2.53 g, 10.1 mmol) and 4-hydroxy-2-methoxybenzaldehyde (2.14 g, 14.1 mmol) were combined in a reaction vessel and treated with isopropanol (50 mL). The reaction vessel was sealed and the reaction was heated to 80° C. with stirring overnight. The reaction was then cooled to room temperature and treated with ether (75 mL). The precipitate that formed was recovered by vacuum filtration and washed with a 20% solution of isopropanol in hexane and then with ether. The recovered solid was then dried under vacuum giving 3.58 g (96%) of a yellow solid. LC-MS: RT=3.87 min, $[M+H]^+=295.1$.

B. Step 2: Preparation of 3-(3-(2-methoxy-4-(m-tolyloxy)benzylidene)-3,4,5,6-tetrahydropyridin-2-yl)pyridine dihydrochloride

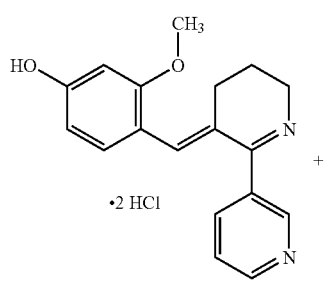

Intermediate 4

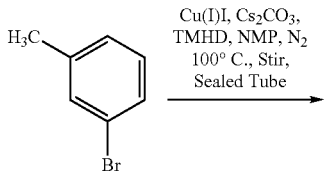

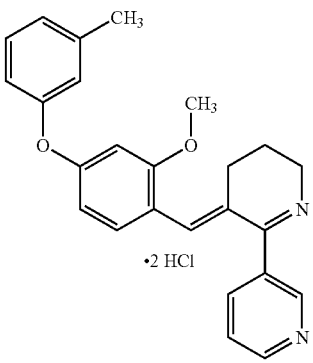

Example 22

3-(3-(2-methoxy-4-(m-tolyloxy)benzylidene)-3,4,5,6-tetrahydropyridin-2-yl)pyridine dihydrochloride was prepared as described in Buck et al. (2002). Briefly, Intermediate 4 (103 mg, 0.28 mmol), copper (I) iodide (27 mg, 0.14 mmol), and cesium carbonate (296 mg, 0.84 mmol) were combined in a reaction vessel and treated with NMP (2 mL) under nitrogen. 3-Bromotoluene (96 mg, 0.56 mmol) and 2,2,6,6-tetramethyl-3,5-heptadione (52 mg, 0.28 mmol) were added. The reaction vessel was sealed, and the reaction was heated to 100° C. with stirring for two days. The reaction was then cooled to room temperature and quenched with concentrated ammonium hydroxide (5 mL) and vigorous stirring for 30 minutes. This mixture was then extracted three times with EtOAc. The EtOAc extracts were washed with brine, combined, dried over $Na_2SO_4$, filtered and concentrated under reduced pressure. The recovered material was eluted through a 20 gram column of silica gel with 10.5:7:7:1:0.1 (660 mL) and with 7:7:7:1:0.1 (330 mL) hexane:MtBE:$CH_2Cl_2$:MeOH:$NH_4OH$ (step gradient). One sample was recovered that was dissolved into methanol and treated with 2 equivalents of 6 N $HCl_{(aq)}$. This solution was concentrated under reduced pressure, and the recovered material re-crystallized from hot isopropanol. The crystals were recovered by vacuum filtration, washed with 20% isopropanol in hexane and then with ether, then dried under vacuum giving 78 mg (60%) of a yellow solid. LC-MS: RT=6.07 min, $[M+H]^+$=385.2.

Example 34

Synthesis of 2-phenoxy-5-((2-(pyridin-3-yl)-5,6-dihydropyridin-3(4H)-ylidene)methyl)pyridine dihydrochloride

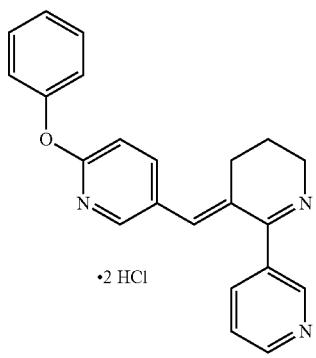

3-(5-Ammoniopentanoyl)pyridinium chloride (101 mg, 0.40 mmol) and 6-phenoxynicotinaldehyde (120 mg, 0.60 mmol) were combined in a reaction vessel and treated with isopropanol (15 mL). The reaction vessel was sealed and the reaction was heated to 80° C. with stirring overnight. The reaction was then cooled to room temperature. The precipitate that formed was recovered by vacuum filtration and washed with a 20% solution of isopropanol in hexane and then with ether. The recovered solid was then dried under vacuum giving 122 mg (73%) of a pale yellow solid. LC-MS: RT=5.08 min, $[M+H]^+$=342.1.

Example 35

Synthesis of 3-(3-((5-phenylfuran-2-yl)methylene)-3,4,5,6-tetrahydropyridin-2-yl)pyridine dihydrochloride

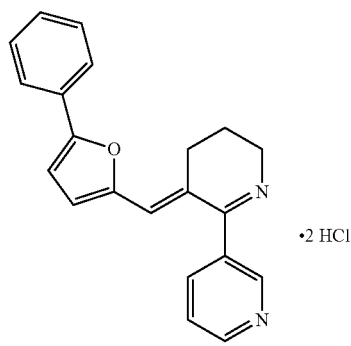

3-(5-Ammoniopentanoyl)pyridinium chloride (188 mg, 0.75 mmol) was transferred to a reaction vessel and treated with isopropanol (12 mL). 5-Phenyl-2-furaldehyde (193 mg, 1.12 mmol) was added, the reaction vessel was sealed, and the reaction was heated to 85° C. with stirring for 6 hours. The reaction was then cooled to room temperature, and the precipitate was recovered by vacuum filtration, washed with isopropanol and ether then dried under vacuum giving 264 mg (91%) of an orange solid. LC-MS: RT=5.15 min, $[M+H]^+$=315.1.

The compounds shown in Table 3 were prepared as described in Example 24 using an appropriate aldehyde. The compounds below were isolated as dihydrochloride salts unless otherwise noted.

TABLE 3

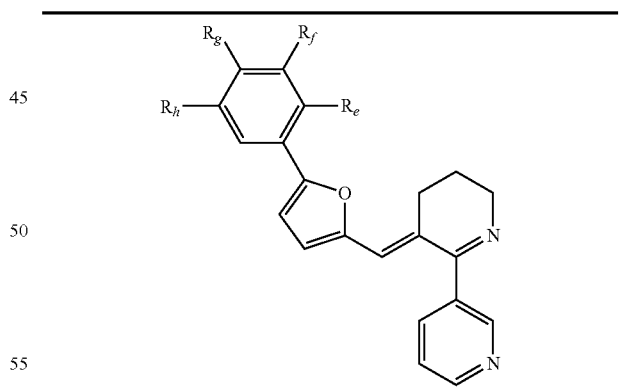

| Example | $R_e$ | $R_f$ | $R_g$ | $R_h$ | Yield | LC RT | MS $[M + H]^+$ |
|---|---|---|---|---|---|---|---|
| 36 | —H | —H | —Cl | —H | 86% | 5.60 min | 349.1 |
| 37 | —H | —Cl | —H | —H | 94% | 5.62 min | 349.1 |
| 38 | —Cl | —H | —H | —H | 93% | 5.60 min | 349.1 |
| 39 | —H | —Cl | —Cl | —H | 85% | 6.07 min | 383.0 |
| 40 | —Cl | —H | —H | —Cl | 83% | 6.05 | 383.0 |

TABLE 3-continued

| Example | $R_e$ | $R_f$ | $R_g$ | $R_h$ | Yield | LC RT | MS [M + H]+ |
|---|---|---|---|---|---|---|---|
| 41 | —H | —Cl | —OCH$_3$ | —H | 94% | 5.59 min | 379.1 |
| 42 | —OCF$_3$ | —H | —H | —H | 81% | 5.99 min | 399.1 |
| 43 | —H | —H | —OCF$_3$ | —H | 85% | 6.04 min | 399.1 |
| 44 | —CF$_3$ | —H | —H | —H | 76% | 5.81 min | 383.1 |
| 45 | —H | —CF$_3$ | —H | —H | 86% | 6.04 min | 383.1 |
| 46 | —Cl | —H | —H | —CF$_3$ | 47% | 6.29 min | 417.0 |
| 47 | —Cl | —H | —CF$_3$ | —H | 73% | 6.60 min | 417.0 |
| 48 | —H | —CF$_3$ | —H | —CF$_3$ | 72% | 6.67 min | 451.0 |
| 49 | —H | —CF$_3$ | —F | —H | 79% | 6.05 min | 401.0 |
| 50 | —H | —H | —SO$_2$NH$_2$ | —H | 90% | 4.18 min | 394.0 |
| 51 | —NO$_2$ | —H | —H | —H | 62% | 5.00 min | 360.0 |
| 52 | —H | —NO$_2$ | —H | —H | 89% | 5.29 | 360.0 |

Example 53

Synthesis of 3-(3-((5-(2,4-dichlorophenyl)furan-2-yl)methylene)-3,4,5,6-tetrahydropyridin-2-yl)pyridine

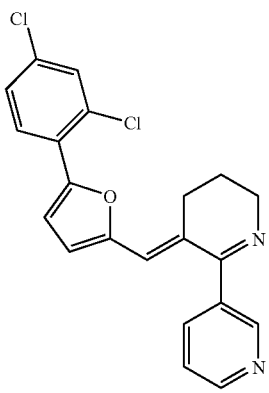

3-(5-Ammoniopentanoyl)pyridinium chloride (103 mg, 0.41 mmol) and 5-(2,4-dichlorophenyl)furfural (128 mg, 0.53 mmol) were combined in a reaction vessel and treated with isopropanol (6 mL). The reaction vessel was sealed and the reaction was heated to 80° C. with stirring overnight. The reaction was then cooled to room temperature, concentrated under reduced pressure and treated with saturated NaHCO$_3$ $_{(aq)}$. This mixture was then extracted three times with EtOAc. The EtOAc extracts were washed with brine, combined, dried over Na$_2$SO$_4$, filtered and concentrated under reduced pressure. The recovered material was eluted through a 20 gram column of silica gel with 10.5:7:7:0.5:0.05 (700 mL) and with 7:7:7:1:0.1 (440 mL) hexane:MtBE:CH$_2$Cl$_2$:MeOH:NH$_4$OH (step gradient). One sample was recovered that slowly solidified. This solid material was re-crystallized from a mixture of hot isopropanol and hexane. The crystals were recovered by vacuum filtration, washed with 20% isopropanol in hexane and then with ether, then dried under vacuum giving 71 mg (45%) of a yellow crystalline solid. LC-MS: RT=6.17 min, [M+H]+=383.0.

Example 54

Synthesis of 3-(3-((5-(4-nitrophenyl)furan-2-yl)methylene)-3,4,5,6-tetrahydropyridin-2-yl)pyridine

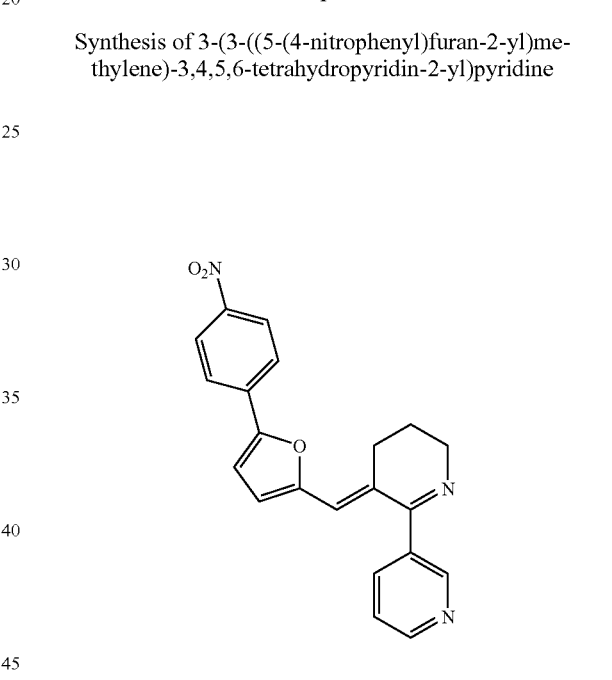

3-(5-Ammoniopentanoyl)pyridinium chloride (95 mg, 0.38 mmol) and 5-(4-nitrophenyl)furfural (99 mg, 0.46 mmol) were combined in a reaction vessel and treated with isopropanol (6 mL). The reaction vessel was sealed and the reaction was heated to 80° C. with stirring overnight. The reaction was then cooled to room temperature, concentrated under reduced pressure and treated with saturated NaHCO$_3$$_{(aq)}$. This mixture was then extracted three times with EtOAc. The EtOAc extracts were washed with brine, combined, dried over Na$_2$SO$_4$, filtered and concentrated under reduced pressure. The recovered material was eluted through a 20 gram column of silica gel with 10.5:7:7:1:0.1 hexane:MtBE:CH$_2$Cl$_2$:MeOH:NH$_4$OH (1 liter). One sample was recovered that appeared to be highly crystalline. This material was re-crystallized from hot methanol. The crystals were recovered by vacuum filtration, washed with isopropanol then dried under vacuum giving 50 mg (36%) of an orange crystalline solid. LC-MS: RT=5.16 min, [M+H]$^+$=360.0.

Example 55

Synthesis of 3-(3-((5-(4-chloro-2-nitrophenyl)furan-2-yl)methylene)-3,4,5,6-tetrahydropyridin-2-yl)pyridine dihydrochloride

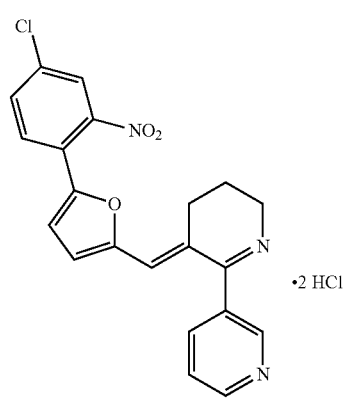

·2 HCl 3-(5-Ammoniopentanoyl)pyridinium chloride (109 mg, 0.43 mmol) and 5-(4-chloro-2-nitrophenyl)furfural (131 mg, 0.52 mmol) were combined in a reaction vessel and treated with isopropanol (6 mL). The reaction vessel was sealed and the reaction was heated to 80° C. with stirring overnight. The reaction was then cooled to room temperature, concentrated under reduced pressure and treated with saturated NaHCO$_3$ $_{(aq)}$. This mixture was then extracted three times with EtOAc. The EtOAc extracts were washed with brine, combined, dried over Na$_2$SO$_4$, filtered and concentrated under reduced pressure. The recovered material was eluted through a 20 gram column of silica gel with 10.5:7:7:1:0.1 hexane:MtBE:CH$_2$Cl$_2$:MeOH:NH$_4$OH (800 mL). One sample was recovered. This material was dissolved into methanol and treated with 2 equivalents of 6 N HCl$_{(aq)}$. This solution was concentrated under reduced pressure and the recovered material re-crystallized from a mix of isopropanol and ether. The crystals were recovered by vacuum filtration, washed with a 20% solution of isopropanol in hexane, and then with ether, then dried under vacuum giving 95 mg (47%) of a yellow solid. LC-MS: RT=5.65 min, [M+H]$^+$=394.0.

Example 56

Synthesis of 3-(3-((5-(2,4-dimethoxyphenyl)furan-2-yl)methylene)-3,4,5,6-tetrahydropyridin-2-yl)pyridine dihydrochloride The preparation of 3-(3-((5-(2,4-dimethoxyphenyl)furan-2-yl)methylene)-3,4,5,6-tetrahydropyridin-2-yl)pyridine dihydrochloride is described below.

A. Step 1: Preparation of Intermediate 5

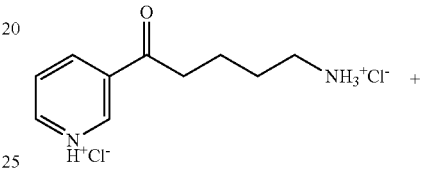

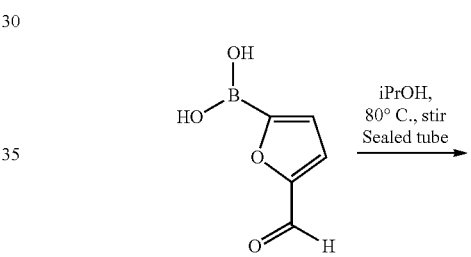

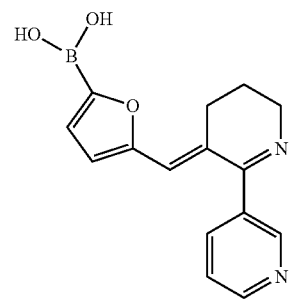

Intermediate 5

3-(5-Ammoniopentanoyl)pyridinium chloride (937 mg, 3.73 mmol) and 5-formyl-2-furanboronic acid (522 mg, 3.73 mmol) were combined in a reaction vessel and treated with isopropanol (30 mL). The reaction vessel was sealed and the reaction was heated to 80° C. with stirring overnight. The reaction was then cooled to room temperature, treated with saturated NaHCO$_3$$_{(aq)}$ and extracted three times with EtOAc. The EtOAc extracts were washed with brine, then combined, dried over NaSO$_4$, filtered and concentrated under reduced pressure and dried under vacuum giving 860 mg of a yellow solid. LC-MS: RT=2.68 min, [M+H]=283.0.

B. Step 2: Preparation of 3-(3-((5-(2,4-dimethoxyphenyl)furan-2-yl)methylene)-3,4,5,6-tetrahydropyridin-2-yl)pyridine

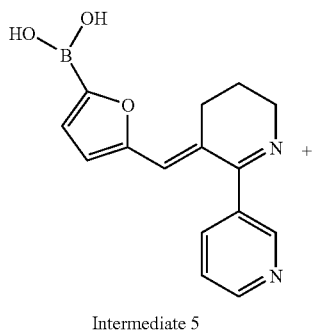

Intermediate 5

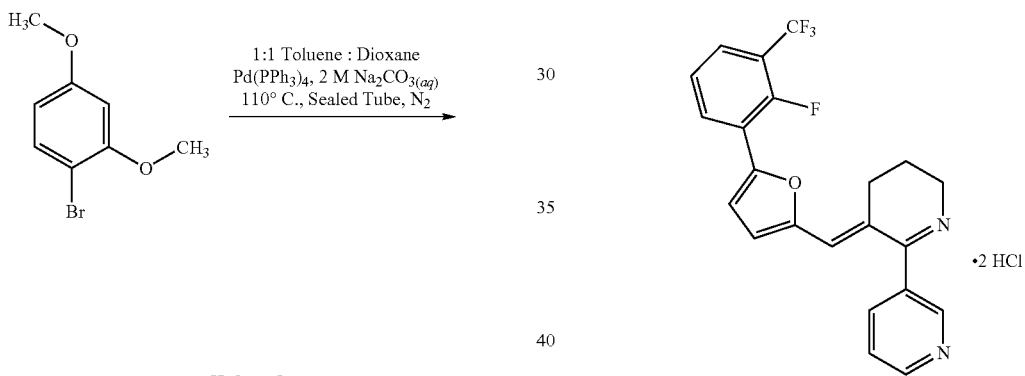

Example 45

Intermediate 5 (95 mg, 0.33 mmol), 2,4-dimethoxybromobenzene (143 mg, 0.66 mmol), and Pd(PPh$_3$)$_4$ (38 mg, 0.03 mmol) were combined in a reaction vessel and treated with a 1:1 mixture of toluene (5 mL) and 1,4-dioxane (5 mL). 2 M Na$_2$CO$_{3(aq)}$ (330 µL, 0.66 mmol) was then added and the reaction vessel flushed with N$_2$ and sealed. The reaction mixture was then heated to 110° C. with stirring overnight. The reaction was then cooled to room temperature and treated with EtOAc. This solution was then washed with water and brine. The aqueous extracts were then back extracted two times with fresh EtOAc. All EtOAc extracts were then combined, dried over Na$_2$SO$_4$, filtered and concentrated under reduced pressure. The recovered material was then eluted through a 20 gram column of silica gel with 99:1:0.1 CH$_2$Cl$_2$:MeOH:NH$_4$OH (1.5 liters). The recovered material was then dissolved into MeOH and treated with 2 eq. of 6 N HCl$_{(aq)}$. This solution was then concentrated under reduced pressure and the recovered material re-crystallized from a mixture of hot ethanol and isopropanol. The crystals were recovered by vacuum filtration and washed with a 20% solution of isopropanol in hexane, and then with ether, then dried under vacuum giving 22 mg (14%) of red crystals. LC-MS: RT=5.59 min, [M+H]$^+$=375.0.

Example 57

Synthesis of 3-(3-((5-(2-fluoro-3-(trifluoromethyl)phenyl)furan-2-yl)methylene)-3,4,5,6-tetrahydropyridin-2-yl)pyridine dihydrochloride

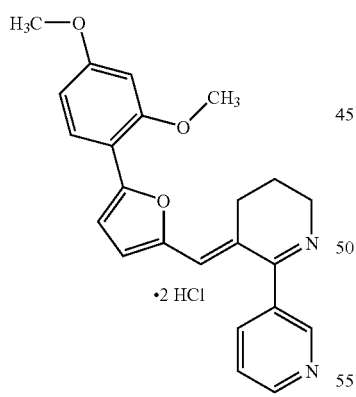

Intermediate 5 (190 mg, 0.67 mmol) was dissolved into a 1:1 mixture of toluene (10 mL) and 1,4-dioxane (10 mL) in a reaction vessel. 2-Fluoro-3-(trifluoromethyl)bromobenzene (326 mg, 1.34 mmol), Pd(PPh$_3$)$_4$ (81 mg, 0.07 mmol), and 2 M Na$_2$CO$_{3(aq)}$ (670 µL, 1.34 mmol) were then added and the reaction vessel flushed with N$_2$ and sealed. The reaction mixture was then heated to 110° C. with stirring for two days. The reaction was then cooled to room temperature, filtered through celite, and the filtrate concentrated under reduced pressure. The recovered material was then treated with water and extracted three times with EtOAc. The EtOAc extracts were then washed with brine, combined, dried over Na$_2$SO$_4$, filtered and concentrated under reduced pressure. The recovered material was then eluted through a 20 gram column of silica gel with 98:2:0.2 CH$_2$Cl$_2$MeOH:NH$_4$OH (1 liter). The recovered material was then dissolved into MeOH and treated with 2 eq. of 6 N HCl$_{(aq)}$. This solution was then concentrated under reduced pressure and the recovered material re-crystallized from a mixture of hot ethanol and isopropanol. The crystals were recovered by vacuum filtration and washed with a 20% solution of isopropanol in hexane, and then with ether, then dried under vacuum giving 30 mg (9.5%) of orange crystals. LC-MS: RT=6.17 min, [M+H]$^+$=401.0.

Example 58

Synthesis of 3-(3-((5-(2-fluorophenyl)furan-2-yl)methylene)-3,4,5,6-tetrahydropyridin-2-yl)pyridine dihydrochloride

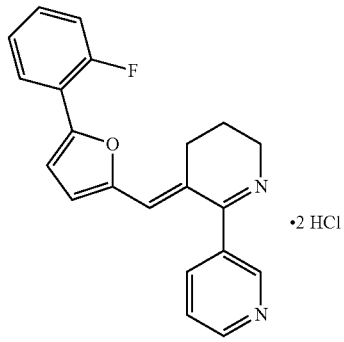

Intermediate 5 (95 mg, 0.33 mmol), 1-fluoro-2-bromobenzene (118 mg, 0.66 mmol), and Pd(PPh$_3$)$_4$ (38 mg, 0.03 mmol) were combined in a reaction vessel and treated with a 1:1 mixture of toluene (5 mL) and 1,4-dioxane (5 mL). 2 M Na$_2$CO$_{3(aq)}$ (330 µL, 0.66 mmol) was added, along with MeOH 91 mL. The reaction vessel was then flushed with N$_2$ and sealed and the reaction mixture heated to 110° C. with stirring overnight. The reaction was then cooled to room temperature, filtered through celite. The filtrate was then treated with water and extracted three times with EtOAc. The EtOAc extracts were then washed with brine, combined, dried over Na$_2$SO$_4$, filtered and concentrated under reduced pressure. The recovered material was then eluted through a 20 gram column of silica gel with 99:1:0.1 CH$_2$Cl$_2$:MeOH:NH$_4$OH (1 liter). The material recovered from this column was then eluted through an Agilent 1100 Series Preparative HPLC system with an Agilent Prep-C18 (21.2 mm I.D.×150 mm) column equipped with an Agilent Prep-C18 (21.2 mm I.D.) guard column, and the following continuous gradient mobile phase using was a mixture of H$_2$O (A) and MeCN (B) containing 0.1% TFA:

| Time (min.) | % A | % B | Flow (mL/min.) |
|---|---|---|---|
| 0.00 | 90 | 10 | 30 |
| 1.00 | 90 | 10 | 30 |
| 11.00 | 10 | 90 | 30 |
| 14.00 | 10 | 90 | 30 |
| 15.00 | 90 | 10 | 30 |
| 16.00 | 90 | 10 | 30 |

The recovered material was then dissolved into MeOH and treated with 2 eq. of 6 N HCl$_{(aq)}$. This solution was then concentrated under reduced pressure and the recovered material dissolved into isopropanol. An orange precipitate was crashed out of this solution with ether, then recovered by vacuum filtration and washed with fresh ether, then dried under vacuum giving 22 mg (16%) of an orange solid. LC-MS: RT=5.42 min, [M+H]$^+$=333.0.

Example 59

Synthesis of 3-(3-((5-(4-fluorophenyl)furan-2-yl)methylene)-3,4,5,6-tetrahydropyridin-2-yl)pyridine dihydrochloride The preparation of 3-(3-((5-(4-fluorophenyl)furan-2-yl)methylene)-3,4,5,6-tetrahydropyridin-2-yl)pyridine dihydrochloride is described below.

A. Step 1: Preparation of Intermediate 6

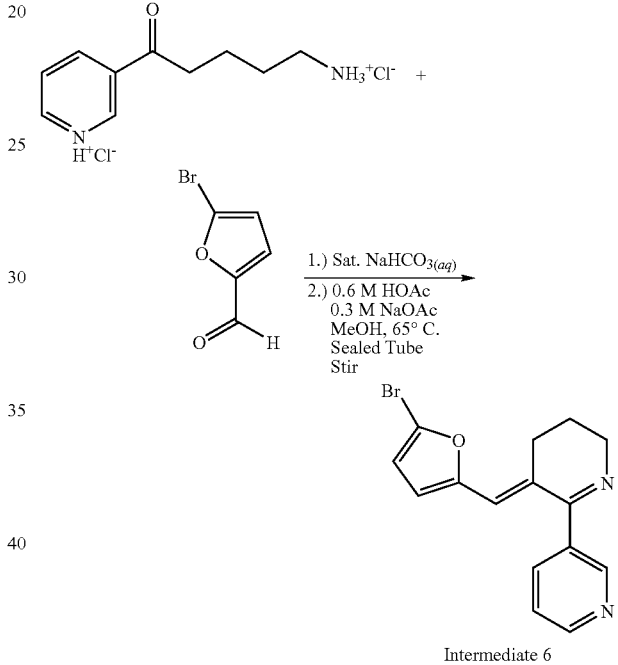

Intermediate 6

3-(5-Ammoniopentanoyl)pyridinium chloride (5.86 g, 23.3 mmol) was treated with saturated NaHCO$_{3(aq)}$ and extracted three times with EtOAc. The EtOAc extracts were washed with brine, combined, dried over Na$_2$SO$_4$, filtered and concentrated under reduced pressure. The recovered material was eluted through a 50 gram column of silica gel with 10.5:7:7:1:0.1 hexane:MtBE:CH$_2$Cl$_2$:MeOH:NH$_4$OH (1 liter). One sample was recovered giving 485 mg (13%, 3.03 mmol) of a light brown oil. This oil was dissolved into a dual solution of 0.6 M acetic acid and 0.3 M sodium acetate in methanol (30 mL) in a reaction vessel. 5-Bromo-2-furaldehyde (795 mg, 4.54 mmol) was added, the reaction vessel was sealed, and the reaction was heated to 65° C. with stirring for 24 hours. The reaction was then cooled, concentrated under reduced pressure, and treated with a saturated solution of NaHCO$_{3(aq)}$ and extracted three times with EtOAc. The EtOAc extracts were then washed with brine, combined, dried over Na$_2$SO$_4$, filtered and concentrated under reduced pressure. The recovered material was then eluted through a 20 gram column of silica gel with 98:2:0.2 CH$_2$Cl$_2$:MeOH:NH$_4$OH (1 liter). The recovered material was then dried under vacuum giving 220 mg (22%) of a brown oil. LC-MS: RT=4.50 min, [M+H]⁺=318.9.

B. Step 2: Preparation of 3-(3-((5-(4-fluorophenyl) furan-2-yl)methylene)-3,4,5,6-tetrahydropyridin-2-yl)pyridine dihydrochloride

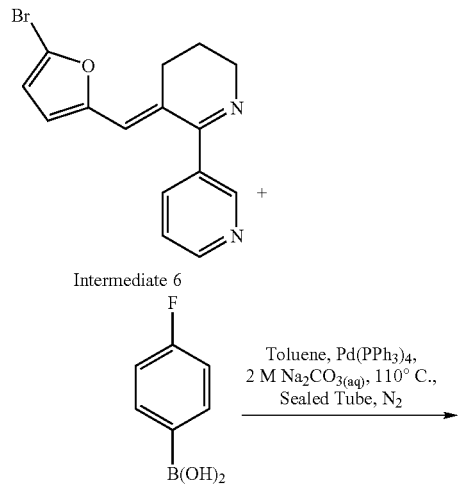

Example 48

Intermediate 6 (110 mg, 0.34 mmol) was dissolved into toluene (10 mL) in a reaction vessel. 4-Fluorobenzeneboronic acid (95 mg, 0.68 mmol), Pd(PPh₃)₄ (39 mg, 0.03 mmol), and 2 M Na₂CO₃₍aq₎ (340 μL, 0.68 mmol) were then added. The reaction vessel was flushed with N₂ and sealed. The reaction was then heated to 110° C. with stirring overnight. The reaction was then cooled to room temperature, diluted with EtOAc and washed with water and with brine. The aqueous extracts were back extracted two times with fresh EtOAc. All EtOAc extracts were combined, dried over Na₂SO₄, filtered, and concentrated under reduced pressure. The recovered material was then eluted through a 20 gram column of silica gel with 98:2:0.2 CH₂Cl₂:MeOH:NH₄OH (750 mL). The recovered material was then dissolved into MeOH and treated with 2 eq. of 6 N HCl₍aq₎, and concentrated under reduced pressure. The recovered material was then recrystallized from a mix of hot isopropanol and ethanol. The crystals were recovered by vacuum filtration, washed with a 20% isopropanol in hexane solution, then with ether, then dried under vacuum giving 73 mg (52%) of yellow needles. LC-MS: RT=5.44 min, [M+H]⁺=333.0.

Example 60

Synthesis of 3-(3-((5-o-tolylfuran-2-yl)methylene)-3,4,5,6-tetrahydropyridin-2-yl)pyridine dihydrochloride

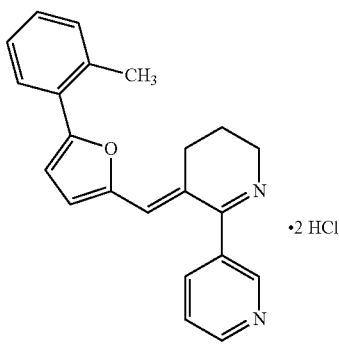

Intermediate 6 (110 mg, 0.34 mmol) was dissolved into toluene (10 mL) in a reaction vessel. 2-Methylbenzeneboronic acid (92 mg, 0.68 mmol), Pd(PPh₃)₄ (39 mg, 0.03 mmol), and 2 M Na₂CO₃₍aq₎ (340 μL, 0.68 mmol) were then added. The reaction vessel was flushed with N₂ and sealed. The reaction was then heated to 110° C. with stirring overnight. The reaction was then cooled to room temperature, diluted with EtOAc and washed with water and with brine. The aqueous extracts were back extracted two times with fresh EtOAc. All EtOAc extracts were combined, dried over Na₂SO₄, filtered, and concentrated under reduced pressure. The recovered material was then eluted through a 20 gram column of silica gel with 98:2:0.2 CH₂Cl₂:MeOH:NH₄ OH. The recovered material was then dissolved into MeOH and treated with 2 eq. of 6 N HCl₍aq₎, and concentrated under reduced pressure. The recovered material was then recrystallized from a mix of hot isopropanol and ethanol. The crystals were recovered by vacuum filtration, washed with a 20% isopropanol in hexane solution, then with ether, then dried under vacuum giving 73 mg (53%) of orange needles. LC-MS: RT=5.68 min, [M+H]⁺=329.0.

Example 61

Synthesis of 1-phenyl-3-(4-((2-(pyridin-3-yl)-5,6-dihydropyridin-3(4H)-ylidene)methyl)phenyl)urea dihydrochloride The preparation of 1-phenyl-3-(4-((2-(pyridin-3-yl)-5,6-dihydropyridin-3(4H)-ylidene)methyl)phenyl)urea dihydrochloride is described below.

A. Step 1: Preparation of Intermediate 7

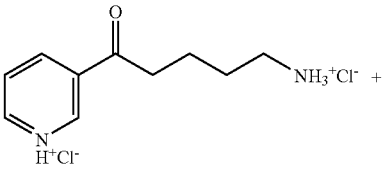

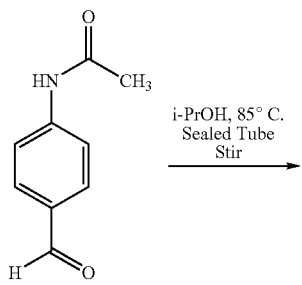

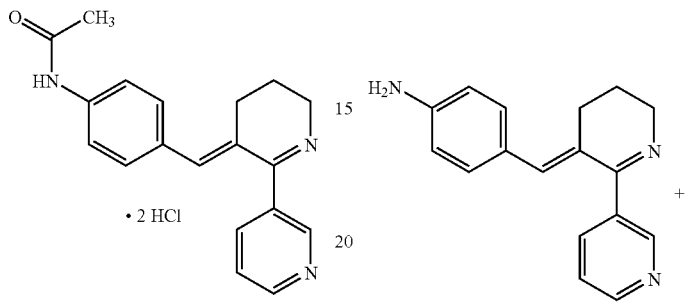

Intermediate 7

3-(5-Ammoniopentanoyl)pyridinium chloride (257 mg, 1.02 mmol) and 4-acetamidobenzaldehyde (250 mg, 1.53 mmol) were combined in a reaction vessel and treated with ispropanol (20 mL). The reaction vessel was sealed and the reaction was heated to 85° C. overnight. The reaction was cooled to room temperature and treated with ether (50 mL). This produced a yellow precipitate that was recovered by vacuum filtration. The precipitate was then washed with a 10% isopropanol in hexane solution and dried under vacuum giving 360 mg (93%) of a yellow solid. LC-MS: RT=3.55 min, [M+H]$^+$=306.1.

B. Step 2: Preparation of Intermediate 8

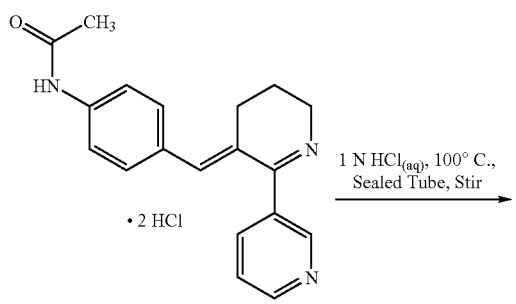

Intermediate 7

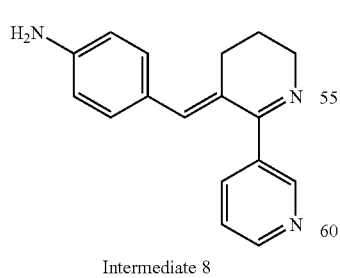

Intermediate 8

Intermediate 7 (78 mg, 0.21 mmol) was dissolved into 1 N HCl$_{(aq)}$ (2 mL, 2 mmol) in a reaction vessel. The reaction vessel was then sealed and the reaction heated to 100° C. overnight. The reaction mixture was then cooled to room temperature and treated with 1 N NaOH$_{(aq)}$ until pH=12. This produced a cloudy yellow precipitate. This mixture was then extracted 3 times with EtOAc. The EtOAc extracts were washed with brine, combined, dried over Na$_2$SO$_4$, filtered, concentrated under reduced pressure, then dried under vacuum giving 51 mg (92%) of a yellow film. LC-MS: RT=3.74 min, [M+H]$^+$=264.1.

C. Step 3: Preparation of 1-phenyl-3-(4-((2-(pyridin-3-yl)-5,6-dihydropyridin-3(4H)-ylidene)methyl)phenyl)urea dihydrochloride

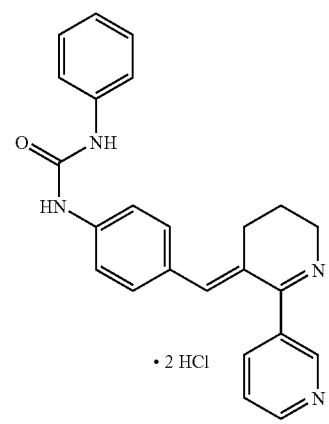

Example 50

Intermediate 8 (51 mg, 0.19 mmol) was dissolved into CH$_2$Cl$_2$ (10 mL) under N$_2$ at room temperature. Phenylisocyanate (35 mg, 0.29 mmol) was then added and the reaction was stirred at room temperature for 48 hours. The reaction was then concentrated under reduced pressure and eluted through a 20 gram column of silica gel with 8.5:7:7:1:0.1 hexane:MtBE:CH$_2$Cl$_2$:MeOH:NH$_4$OH (470 mL). One sample was recovered that was dissolved into MeOH and treated with 2 eq. of 6 N HCl$_{(aq)}$. This solution was concentrated under reduced pressure, then partially dissolved into hot isopropanol. A solid was recovered by vacuum filtration from this mixture after the solvent had cooled. The recovered solid was washed with ether, then dried under vacuum giving 22 mg (23%) of a red powdery solid. LC-MS: RT=5.02 min, [M+H]$^+$=383.1.

Example 62

Synthesis of 1-(3,4-dichlorophenyl)-3-(4-(2-(pyridin-3-yl)-5,6-dihydropyridin-3(4H)-ylidene)methyl)phenyl)urea hydrochloride

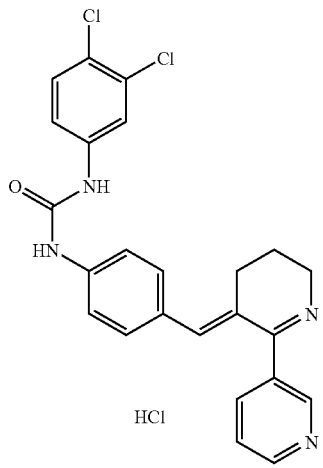

Intermediate 8 (118 mg, 0.45 mmol), $Cs_2CO_3$ (317 mg, 0.90 mmol), and 3,4-dichlorophenylisocyanate (126 mg, 0.67 mmol) were combined under $N_2$ and treated with $CH_2Cl_2$ (10 mL). This mixture was then vigorously stirred for 5 days. The reaction mixture was then directly applied to a 20 gram column of silica gel and eluted with a 99:1:0.1 (1 liter) and a 95:5:0.5 (250 mL) $CH_2Cl_2$:MeOH:$NH_4OH$ step gradient. One sample was recovered that was dissolved into MeOH and treated with 1 eq. of 6 N $HCl_{(aq)}$. This solution was then concentrated under reduced pressure and the recovered material was dissolved into hot isopropanol. When this solution had cooled, it was diluted with ether, which produced a precipitate that was recovered by vacuum filtration. This precipitate was then washed with a 20% isopropanol in hexane solution, then dried under vacuum giving 51 mg (23%) of a yellow solid. LC-MS: RT=5.97 min, [M+H]$^+$=453.1.

Example 63

Synthesis of 1-(3-methoxyphenyl)-3-(4-((2-(pyridin-3-yl)-5,6-dihydropyridin-3(4H)-ylidene)methyl)phenyl)urea hydrochloride

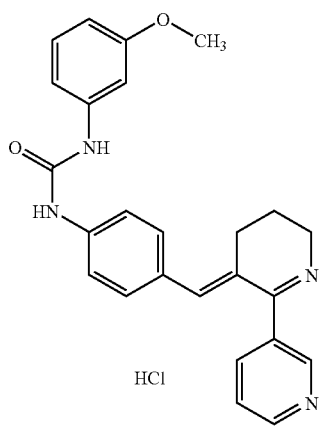

Intermediate 8 (75 mg, 0.28 mmol) and $K_2CO_3$ (77 mg, 0.56 mmol) were combined under $N_2$ and treated with $CH_2Cl_2$ (10 mL). 3-Methoxyphenylisocyanate (84 mg, 0.56 mmol) was then added, and this mixture was vigorously stirred overnight. The reaction mixture was then directly applied to a 20 gram column of silica gel and eluted with a 99:1:0.1 (1 liter) and a 97.5:2.5:0.25 (500 mL) $CH_2Cl_2$:MeOH:$NH_4OH$ step gradient. One sample was recovered that was dissolved into MeOH and treated with 1 eq. of 6 N $HCl_{(aq)}$. This solution was then concentrated under reduced pressure and the recovered material was re-crystallized from a mixture of isopropanol and ether. This solid was then recovered by vacuum filtration and washed with a 20% isopropanol in hexane solution and then with ether, then dried under vacuum giving 89 mg (70%) of a yellow solid. LC-MS: RT=4.97 min, [M+H]$^+$=413.2.

Example 64

Synthesis of 4-(3-(2-fluoro-4-methoxybenzylidene)-3,4,5,6-tetrahydropyridin-2-yl)isoquinoline dihydrochloride The preparation of 4-(3-(2-fluoro-4-methoxybenzylidene)-3,4,5,6-tetrahydropyridin-2-yl)isoquinoline dihydrochloride is described below.

A. Step 1: Preparation of Intermediate 9

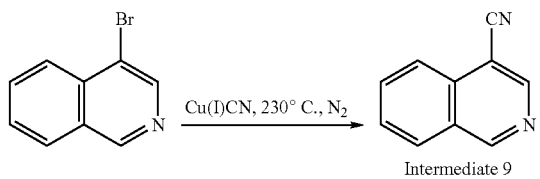

Intermediate 9 was prepared as described in Tyson, F. T. J. Am. Chem. Soc., 1939, 61 (1), 183-185. Briefly, 4-Bromoisoquinoline (3.36 g, 16.2 mmol) and Cu(I)CN (2.17 g, 24.2 mmol) were combined as the dry solids in a round bottom flask fitted with a magnetic stirrer and vigeraux column under $N_2$. Heat was applied. At approximately 150° C., the mixture began to stir freely. At approximately 230° C., the reaction mixture formed a black solid that began to splatter onto the sides of the flask. The reaction was cooled to room temperature and treated with concentrated $NH_4OH$ overnight. This mixture was then extracted 3 times with EtOAc. The EtOAc extracts were washed with dilute $NH_4OH_{(aq)}$ and brine, then combined, dried over $Na_2SO_4$, treated with decolorizing charcoal, filtered through celite, then concentrated under reduced pressure.

The recovered material was dissolved into a mixture of hot isopropanol and methanol to re-crystallize. The crystals were recovered by vacuum filtration, washed with fresh isopropanol and dried under vacuum giving 1.47 g (58%) of yellow crystals. LC-MS: RT=7.86 min, [M+H]$^+$=155.1.

B. Step 2: Preparation of Intermediate 10

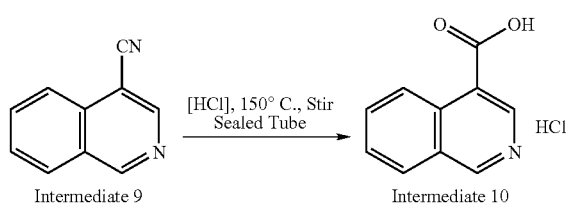

Intermediate 10 was prepared as described in Tyson et al. Briefly, Intermediate 9 (1.47 g, 9.5 mmol) was transferred to a reaction vessel and treated with concentrated hydrochloric acid (12 mL). The reaction vessel was sealed and the reaction mixture was heated to 150° C. with stirring for 8 hours, then cooled to room temperature. This gave a white solid that was recovered by vacuum filtration, washed with isopropanol, and dried under vacuum giving 1.74 g (87%) of a white crystalline solid. LC-MS: RT=3.64 min, [M+H]$^+$=174.1.

C. Step 3: Preparation of Intermediate 11

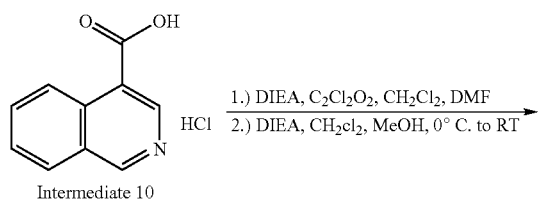

Intermediate 10 (1.47 g, 7.0 mmol) was suspended into CH$_2$Cl$_2$ (100 mL) under N$_2$ at room temperature and treated with N,N-diisopropylethylamine (1.0 g, 7.7 mmol). Dimethylformamide (catalytic, 4 drops) was added, followed by the addition of the oxalyl chloride (1.02 g, 8.0 mmol). There was a gas evolution and the reaction mixture developed an opaque yellow color. This mixture was stirred at room temperature for 45 minutes then cooled to 0° C. and treated with additional 1.1 eq. of N,N-diisopropylethylamine (1.0 g, 7.7 mmol). An excess of methanol (5 mL) was then added, and the reaction mixture was left to stir overnight with gradual warming to room temperature. The reaction was then treated with saturated NaHCO$_{3(aq)}$ and extracted three times with CH$_2$Cl$_2$. The CH$_2$Cl$_2$ extracts were washed with brine, combined, dried over Na$_2$SO$_4$, filtered, and concentrated under reduced pressure. The recovered material was then eluted through a 50 gram column of silica gel with a 10% (750 mL) and 20% (500 mL) EtOAc:hexane step gradient. One sample was recovered and dried under vacuum giving 1.17 g (89%) of an off white solid. LC-MS: RT=8.25 min, [M+H]$^+$=188.1.

D. Step 4: Preparation of Intermediate 12

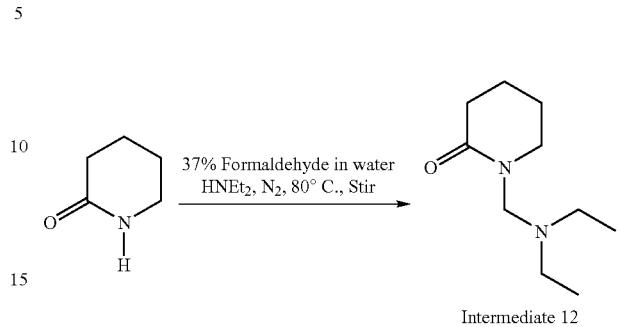

Intermediate 12 was prepared as described in U.S. Pat. No. 5,602,257 to Zoltewicz. δ-Valerolactam (4.67 g, 47.1 mmol), formaldehyde (37% by wt. in H$_2$O, 4.6 mL of solution, 1.70 g, 56.5 mmol), and diethylamine (4.13 g, 56.5 mmol) were combined in a reaction vessel. The reaction vessel was flushed with N$_2$, then sealed and the reaction mixture was heated to 80° C. overnight. The reaction was then cooled to room temperature, partially concentrated under reduced pressure, then extracted three times with EtOAc. The EtOAc extracts were then washed with brine, combined, dried over Na$_2$SO$_4$, filtered, concentrated under reduced pressure and dried under vacuum giving 6.49 g (74%) of a yellow mobile oil. $^1$H NMR (DMSO-d6) δ 4.05 (s, 2 H), 3.26 (broad m, 2 H), 2.48 (q, 4 H, J=7.2 Hz), 2.21 (broad m, 2 H), 1.68 (broad m, 4 H), 0.94 (t, 6 H, J=7.2 Hz).

E. Step 5: Preparation of Intermediate 13

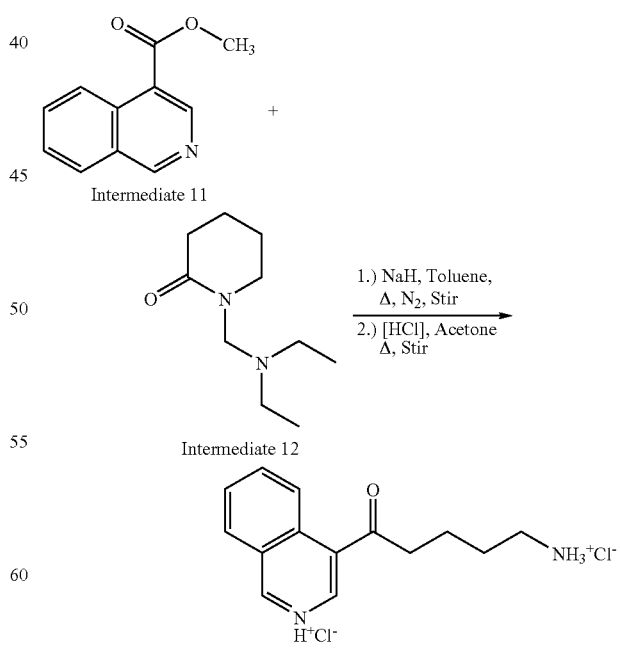

Intermediate 11 (1.35 g, 7.2 mmol) and Intermediate 12 (1.39 g, 7.6 mmol) were combined and dissolved into toluene (50 mL) under $N_2$ at room temperature. NaH (346 mg, 14.4 mmol) was added, and the reaction mixture was heated to reflux with stirring, under $N_2$, overnight. An additional 2 eq. of NaH (346 mg, 14.4 mmol) was then added, and reflux was continued for 3.5 hours. The reaction was then cooled to room temperature and filtered under vacuum. The filtrate was then concentrated under reduced pressure. The recovered material was then treated with concentrated hydrochloric acid (25 mL) and acetone (5 mL) and heated to reflux overnight. The reaction was then cooled to room temperature, diluted with isopropanol (150 mL) and cooled to −20° C. Crystals did form and were recovered by vacuum filtration, washed with fresh isopropanol, and dried under vacuum giving 371 mg (17%) of a white solid. LC-MS: RT=5.45 min, [M+H]$^+$=229.1.

F. Step 6: Preparation of 4-(3-(2-fluoro-4-methoxybenzylidene)-3,4,5,6-tetrahydropyridin-2-yl)isoquinoline dihydrochloride

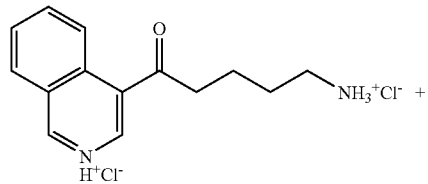

Intermediate 13

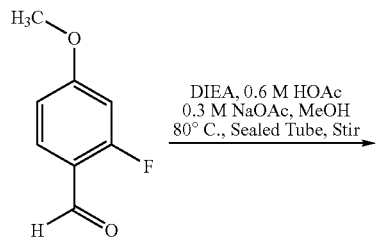

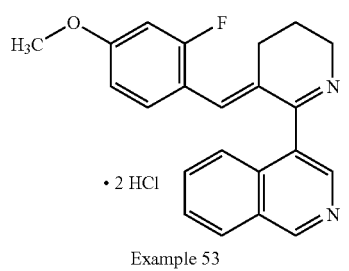

Example 53

Intermediate 13 (133 mg, 0.44 mmol) was suspended into methanol (2 mL) in a reaction vessel and treated with N,N-diisopropylethylamine (143 mg, 1.10 mmol). This gave a solution. 2-Fluoro-4-methoxybenzaldehyde was then added. This solution was then treated with a dual solution of 0.6 M HOAc and 0.3 M NaOAc in methanol (10 mL). The reaction vessel was sealed and the reaction heated to 80° C. for 24 hours, then cooled to room temperature. The reaction mixture was then partially concentrated under reduced pressure and the recovered material treated with saturated NaHCO$_{3(aq)}$. This mixture was then extracted three times with EtOAc. The EtOAc extracts were then washed with brine, combined, dried over Na$_2$SO$_4$, filtered, concentrated under reduced pressure. The recovered material was then eluted through a 20 gram column of silica gel with 7:7:7:1:0.1 hexane:MtBE:CH$_2$Cl$_2$:MeOH:NH$_4$OH (660 mL). One sample was recovered that was dissolved into MeOH and treated with 2 eq. of 6 N HCl$_{(aq)}$. This solution was then concentrated under reduced pressure and the recovered material was re-crystallized from hot isopropanol. This solid was then recovered by vacuum filtration and washed with fresh isopropanol, then dried under vacuum giving 85 mg (46%) of yellow needles. LC-MS: RT=5.20 min, [M+H]$^+$=346.9.

Example 65

Synthesis of 4-(3-(2,4-dimethoxybenzylidene)-3,4,5,6-tetrahydropyridin-2-yl)isoquinoline sulfate

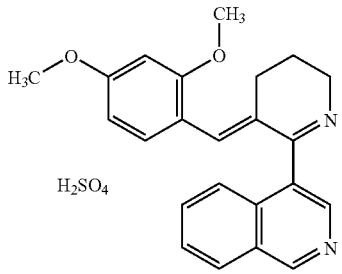

Intermediate 13 (134 mg, 0.44 mmol) was dissolved into a dual solution of 0.6 M HOAc and 0.3 M NaOAc in methanol (10 mL) in a reaction vessel. 2,4-Dimethoxybenzaldehyde (148 mg, 0.88 mmol) was then added and the reaction vessel sealed. The reaction was then heated to 80° C. with stirring overnight, then cooled to room temperature. The reaction mixture was then partially concentrated under reduced pressure and the recovered material treated with saturated NaHCO$_{3(aq)}$. This mixture was extracted three times with EtOAc. The EtOAc extracts were then washed with brine, combined, dried over Na$_2$SO$_4$, filtered, concentrated under reduced pressure. The recovered material was then eluted through a 20 gram column of silica gel with 99:1:0.1CH$_2$Cl$_2$:MeOH:NH$_4$OH (1 liter). One sample was recovered that was dissolved into MeOH and treated with 1 eq. of a 1 N H$_2$SO$_4$ $_{(aq)}$ solution, then concentrated under reduced pressure. The recovered material was then dissolved into hot isopropanol and precipitated from solution with ether. The precipitate was recovered by vacuum filtration, washed with ether, then dried under vacuum giving 3 mg (1.5%) of a yellow solid. LC-MS: RT=5.23 min, [M+H]+=359.0.

Example 66

Synthesis of 6-(3-(2,4-dimethoxybenzylidene)-3,4,5,6-tetrahydropyridin-2-yl)quinoline hydrochloride The preparation of 6-(3-(2,4-dimethoxybenzylidene)-3,4,5,6-tetrahydropyridin-2-yl)quinoline hydrochloride is described below.

A. Step 1: Preparation of Intermediate 14

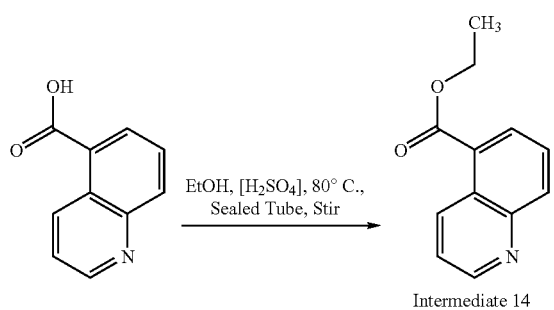

Intermediate 14

Intermediate 14 was prepared as described in EP 0381375 B1, page 21. 6-quinolinecarboxylic acid (12.2 g, 70.4 mmol) was suspended into ethanol (70 mL) in a reaction vessel. Concentrated sulfuric acid (12 mL) was added, the reaction vessel was sealed and the reaction was heated to 80° C. for 48 hours. The reaction was then cooled to room temperature, partially concentrated under reduced pressure and treated with concentrated ammonium hydroxide and 1 N NaOH$_{(aq)}$ until pH=9. This produced an oil that separated from solution. This mixture was extracted three times with EtOAc. The EtOAc extracts were then washed with brine, combined, dried over Na$_2$SO$_4$, filtered, concentrated under reduced pressure giving a green oil. This oil was filtered through a 9.5 cm×3.0 cm plug of silica gel with 50% EtOAc:hexane. The filtrate was concentrated under reduced pressure and dried under vacuum giving 10.66 g (75%) of a light green oil. $^1$H NMR (DMSO-d6) δ 9.03 (dd, 1H, J=4.27, 1.70 Hz), 8.70 (d, 1H, J=1.71 Hz), 8.60 (broad d, 1H, J=8.12 Hz), 8.22 (dd, 1H, J=8.54, 1.71 Hz), 8.11 (d, 1H, J=8.97 Hz), 7.64 (dd, 1H, J=8.12, 4.27 Hz), 4.40 (q, 2H, J=7.26 Hz), 1.38 (t, 3H, J=7.26 Hz).

B. Step 2: Preparation of Intermediate 15

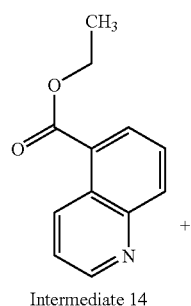

Intermediate 14

+

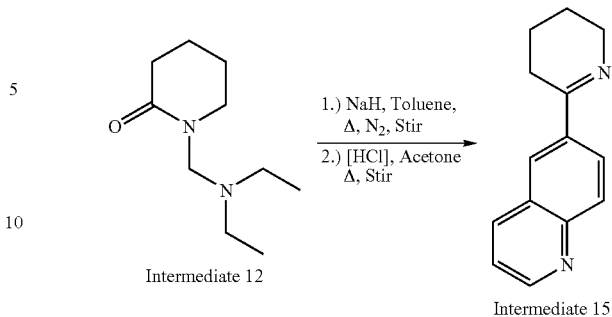

Intermediate 12

Intermediate 15

Intermediate 14 (2.93 g, 14.6 mmol) was dissolved into toluene (100 mL) under N$_2$ at room temperature. Intermediate 12 (2.68 g, 14.6 mmol) was added, followed by the addition of the NaH (701 mg, 29.2 mmol). There was a gas evolution. This mixture was heated to reflux for 4 hours under N$_2$, then partially cooled. A second 2 eq. of NaH (701 mg, 29.2 mmol) was then added and the reaction heated to reflux for 4 hours, then gradually cooled to room temperature, with stirring under N$_2$ overnight. The reaction mixture was then filtered through celite with toluene, and the filtrate concentrated under reduced pressure. The recovered material was then treated with concentrated hydrochloric acid (50 mL) and acetone (10 mL). This mixture was then heated to reflux with stirring overnight. The reaction mixture was then cooled to room temperature. An oil appeared to form in the reaction mixture. This mixture was treated with concentrated ammonium hydroxide until it was basic. The mixture was then extracted three times with EtOAc. The EtOAc extracts were then washed with brine, combined, dried over Na$_2$SO$_4$, filtered, concentrated under reduced pressure giving 880 mg (28%) of a brown oil. $^1$H NMR (DMSO-d6) δ 8.90 (dd, 1 H, J=3.84, 1.71 Hz), 8.43 (dd, 1 H, J=8.54, 1.10 Hz), 8.34 (d, 1 H, J=2.14 Hz), 8.30 (dd, 1 H, J=8.97, 2.14 Hz), 7.98 (d, 1 H, J=8.97 Hz), 7.55 (dd, 1 H, J=8.54, 4.27 Hz), 3.81 (m, 2 H), 2.76 (m, 2 H), 1.65 (broad m, 4 H).

C. Step 3: Preparation of 6-(3-(2,4-dimethoxybenzylidene)-3,4,5,6-tetrahydropyridin-2-yl)quinoline hydrochloride

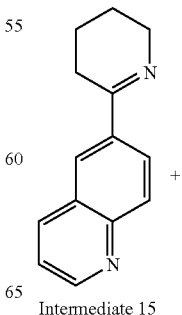

Intermediate 15

+

-continued

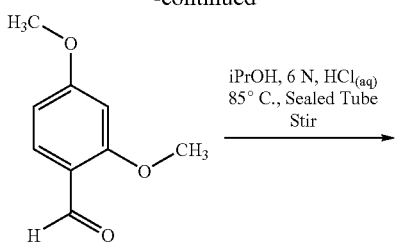

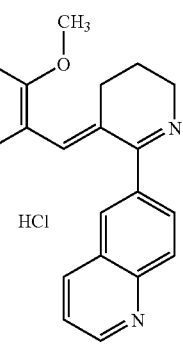

Example 55

Intermediate 15 (214 mg, 1.02 mmol) was dissolved into isopropanol (6 mL) in a reaction vessel and treated with 6 N $HCl_{(aq)}$ (340 µL, 2.0 mmol). 2,4-Dimethoxybenzaldehyde (254 mg, 1.53 mmol) was then added, the reaction vessel was sealed, and the reaction was heated to 85° C. with stirring overnight. The reaction was cooled to room temperature, partially concentrated under reduced pressure, treated with saturated $NaHCO_{3(aq)}$, then extracted three times with EtOAc. The EtOAc extracts were then washed with brine, combined, dried over $Na_2SO_4$, filtered, concentrated under reduced pressure. The recovered material was then purified by eluting it through 3 successive 20 gram columns of silica gel with the following sequential eluants:

1.) 7:7:7:1:0.1 Hexane:MtBE:$CH_2Cl_2$:MeOH:$NH_4OH$.

2.) 99:1:0.1 $CH_2Cl_2$:MeOH:$NH_4OH$.

3.) 10.5:7:7:0.5:0.05 Hexane:MtBE:$CH_2Cl_2$:MeOH:$NH_4OH$.

This eventually gave a colorless film that was dissolved into MeOH and treated with 1 eq. of 6 N $HCl_{(aq)}$. This solution was then concentrated under reduced pressure and the recovered material dissolved into isopropanol and precipitated from solution with ether. The precipitate was then collected by vacuum filtration, washed with fresh ether, then dried under vacuum giving 4 mg (1%) of a yellow solid. LC-MS: RT=5.06 min, $[M+H]^+$=359.1.

Example 67

Synthesis of 6-(3-((5-(2-chlorophenyl)furan-2-yl)methylene)-3,4,5,6-tetrahydropyridin-2-yl)quinoline hydrochloride

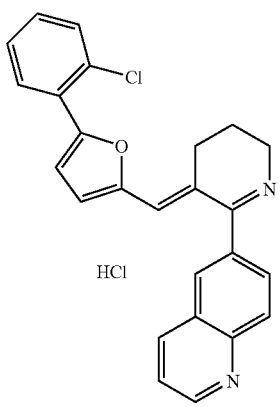

Intermediate 15 (188 mg, 0.89 mmol) was dissolved into isopropanol (20 mL) in a reaction vessel and treated with 6 N $HCl_{(aq)}$ (300 µL, 1.8 mmol). 5-(2-Chlorophenyl)furfural (257 mg, 1.25 mmol) was then added, the reaction vessel was sealed, and the reaction was heated to 85° C. with stirring overnight. The reaction was cooled to room temperature, partially concentrated under reduced pressure, treated with saturated $NaHCO_{3(aq)}$, then extracted three times with EtOAc. The EtOAc extracts were then washed with brine, combined, dried over $Na_2SO_4$, filtered, concentrated under reduced pressure. The recovered material was then eluted through a 20 gram column of silica gel with 10.5:7:7:0.5:0.05 Hexane:MtBE:$CH_2Cl_2$:MeOH:$NH_4OH$ (1 liter). The recovered material was dissolved into MeOH and treated with 1 eq. of 6 N $HCl_{(aq)}$. This solution was then concentrated under reduced pressure and the recovered material dissolved into a mixture of isopropanol and ether. Crystals formed upon cooling, and were recovered by vacuum filtration and washed with a 20% solution of isopropanol in hexane. The crystals were dried under vacuum giving 56 mg (14%) of dark brown crystals. LC-MS: RT=5.88 min, $[M+H]^+$=399.1.

Example 68

Synthesis of 6-(3-(2-fluoro-4-methoxybenzylidene)-3,4,5,6-tetrahydropyridin-2-yl)quinoline dihydrochloride

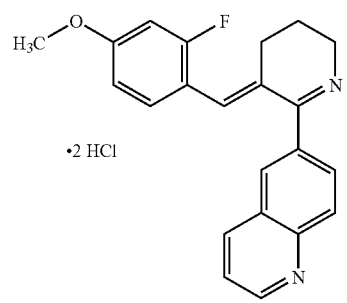

Intermediate 15 (200 mg, 0.95 mmol) and 2-fluoro-4-methoxybenzaldehyde (220 mg, 1.43 mmol) were combined and dissolved into isopropanol (10 mL) in a reaction vessel, then treated with 6 N HCl$_{(aq)}$ (633 µL, 3.8 mmol). The reaction vessel was sealed, and the reaction was heated to 80° C. with stirring overnight. The reaction was cooled to room temperature, concentrated under reduced pressure, treated with saturated NaHCO$_{3(aq)}$, then extracted three times with EtOAc. The EtOAc extracts were then washed with brine, combined, dried over Na$_2$SO$_4$, filtered, concentrated under reduced pressure. The recovered material was then eluted through a 20 gram column of silica gel with 10.5:7:7:0.5:0.05 Hexane:MtBE:CH$_2$Cl$_2$:MeOH:NH$_4$OH (1 liter). The recovered material was dissolved into MeOH and treated with 2 eq. of 6 N HCl$_{(aq)}$. This solution was then concentrated under reduced pressure and the recovered material dissolved into isopropanol and precipitated from solution with ether. The precipitate was recovered by vacuum filtration, washed with fresh ether, then dried under vacuum giving 10 mg (2.5%) of a yellow solid. LC-MS: RT=5.08 min, [M+H]$^+$=347.0.

Example 69

Synthesis of 3-((2-(pyridin-3-yl)-5,6-dihydropyridin-3(4H)-ylidene)methyl)pyridine trihydrochloride

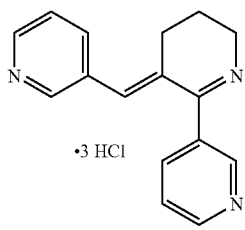

3-(5-Ammoniopentanoyl)pyridinium chloride (152 mg, 0.60 mmol) was suspended into ethanol (10 mL) in a reaction vessel and treated with concentrated hydrochloric acid (5 drops). Pyridine-3-carboxaldehyde (84 mg, 0.78 mmol) was added and the reaction vessel was sealed. The reaction was heated to 85° C. for 48 hours, then cooled to room temperature. The reaction mixture was concentrated under reduced pressure and treated with saturated NaHCO$_{3(aq)}$, then extracted three times with EtOAc. The EtOAc extracts were washed with brine, combined, dried over Na$_2$SO$_4$, filtered, and concentrated under reduced pressure. The recovered material was then eluted through a 20 gram column of silica gel with a 98:2:0.2 and 96:4:0.4 CH$_2$Cl$_2$:MeOH:NH$_4$OH step gradient (500 mL each step). The recovered material was dissolved into MeOH and treated with 3 eq. of 6 N HCl$_{(aq)}$. This solution was concentrated under reduced pressure and the recovered material dissolved into hot isopropanol. This solution was allowed to cool to room temperature, then diluted with ether which produced a precipitate. The precipitate was recovered by vacuum filtration, washed with fresh isopropanol, then dried under vacuum giving 39 mg (18%) of a brown solid. LC-MS: RT=2.14 min, [M+H]$^+$=250.1.

Example 70

Synthesis of methyl 3-(5-((2-(pyridin-3-yl)-5,6-dihydropyridin-3(4H)-ylidene)methyl)furan-2-yl)thiophene-2-carboxylate dihydrochloride

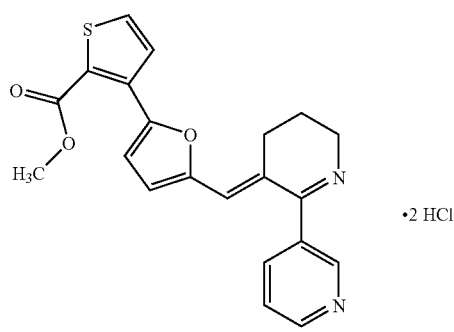

3-(5-Ammoniopentanoyl)pyridinium chloride (99 mg, 0.39 mmol) and methyl 3-(5-formyl-2-furyl)thiophene-2-carboxylate (102 mg, 0.43 mmol) were combined in a reaction vessel and treated with isopropanol (6 mL). The reaction vessel was sealed and the reaction was heated to 80° C. with stirring overnight. The reaction was cooled to room temperature. The precipitate was recovered by vacuum filtration, then treated with saturated NaHCO$_{3(aq)}$ and extracted three times with EtOAc. The EtOAc extracts were washed with brine, combined, dried over Na$_2$SO$_4$, filtered, concentrated under reduced pressure, and eluted through a 20 gram column of silica gel with 99:1:0.1 CH$_2$Cl$_2$:MeOH:NH$_4$OH (1 liter). The recovered material was dissolved into MeOH and treated with 2 eq. of 6 N HCl$_{(aq)}$. This solution was concentrated under reduced pressure and the recovered material was dissolved into hot isopropanol to re-crystallize. Crystals were recovered by vacuum filtration, washed with a 20 isopropanol in hexane solution, and then with ether, then dried under vacuum giving 86 mg (48%) of an orange solid. LC-MS: RT=5.25 min, [M+H]$^+$=379.0.

Example 71

Synthesis of 3-(3-((5-(3-fluoro-2-(trifluoromethyl)phenyl)furan-2-yl)methylene)-3,4,5,6-tetrahydropyridin-2-yl)pyridine dihydrochloride

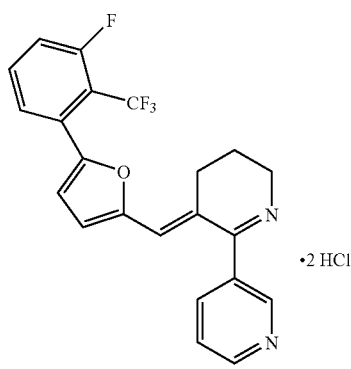

Intermediate 5 (190 mg, 0.67 mmol) (prepared as described in Example 35) was dissolved into a 1:1 mixture of toluene (20 mL) and 1,4-dioxane (10 mL) in a reaction vessel. 3-Fluoro-2-(trifluoromethyl)bromobenzene (326 mg, 1.34 mmol), Pd(PPh$_3$)$_4$ (81 mg, 0.07 mmol), and 2 M Na$_2$CO$_{3(aq)}$ (670 µL, 1.34 mmol) were added and the reaction vessel flushed with N$_2$ and sealed. The reaction mixture was heated to 110° C. with stirring overnight. The reaction was then cooled to room temperature, filtered through Celite®, and the filtrate concentrated under reduced pressure. The recovered material was then treated with water and extracted three times with EtOAc. The EtOAc extracts were washed with brine, combined, dried over Na$_2$SO$_4$, filtered and concentrated under reduced pressure. The recovered material was then eluted through a 20 gram column of silica gel with 98:2:0.2 CH$_2$Cl$_2$:MeOH:NH$_4$OH (1 liter). The material recovered from this column was eluted through a second 20 gram column of silica gel with an 8.5:7:7:0.5:0.05 (685 mL) and with 7:7:7:1:0.1 (440 mL) Hexane:MtBE:CH$_2$Cl$_2$: MeOH: NH$_4$OH step gradient. The recovered material was dissolved into MeOH and treated with 2 eq. of 6 N HCl$_{(aq)}$. This solution was then concentrated under reduced pressure and the recovered material re-crystallized from a mixture of hot ethanol and isopropanol. The crystals were recovered by vacuum filtration and washed with a 20% solution of isopropanol in hexane, and then with ether, then dried under vacuum giving 29 mg (9%) of a golden yellow solid. LC-MS: RT=5.88 min, [M+H]$^+$=401.0.

Example 72

Synthesis of 3-(3-(4-isopropoxy-2-methoxybenzylidene)-3,4,5,6-tetrahydropyridin-2-yl)pyridine dihydrochloride

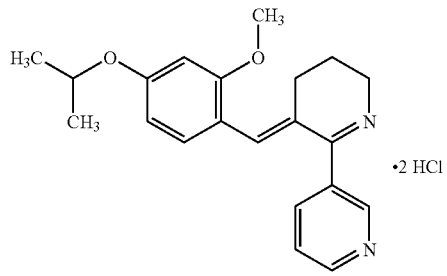

(E)-3-(3-(4-isopropoxy-2-methoxybenzylidene)-3,4,5,6-tetrahydropyridin-2-yl)pyridine dihydrochloride was prepared as described in Lepore, S. D.; He, Y. *J. Org. Chem.*, 2003, 68, 8261-8263. Intermediate 4 (1.0 g, 2.7 mmol) (prepared as described in Example 22) was dissolved into water, treated with saturated NaHCO$_{3(aq)}$, and extracted five times with CH$_2$Cl$_2$. The CH$_2$Cl$_2$ extracts were washed with brine, combined, dried over Na$_2$SO$_4$, filtered and concentrated under reduced pressure and dried under vacuum giving 705 mg (89%) of a yellow solid. PPh$_3$ (682 mg, 2.6 mmol), isopropanol (156 mg, 2.6 mmol) and DMF (2 mL) were added to this solid under N$_2$ at room temperature. This mixture was then treated to ultrasound (42 kHz, Branson brand 5510 sonicator) for 5 minutes. DIAD (526 mg, 2.6 mmol) was then added as the neat reagent, dropwise, via syringe, over 8 minutes. This mixture was then treated to ultrasound at room temperature under N$_2$, with occasional agitation of the reaction flask for 20 minutes. The reaction was quenched with water and extracted three times with EtOAc. The EtOAc extracts were washed with brine, combined, dried over Na$_2$SO$_4$, filtered and concentrated under reduced pressure. The recovered material was then eluted through a 50 gram column of silica gel with the following step gradient: 99:1:0.1 (1 liter); 98:2:0.2 (500 mL); 97:3:0.3 (500 mL); and 96:4:0.4 (500 mL) CH$_2$Cl$_2$:MeOH:NH$_4$OH. The material recovered from this column was dissolved into methanol and treated with 2 eq. of 6 N HCl$_{(aq)}$. This solution was concentrated under reduced pressure and the recovered material dissolved into hot isopropanol and ethanol to re-crystallize. The crystals were recovered by vacuum filtration, washed with fresh isopropanol, then dried under vacuum giving 203 mg (20%) of a yellow solid. LC-MS: RT=5.49 min, [M+H]$^+$=337.1.

Example 73

Synthesis of 3-(3-(4-isopropoxy-3-methoxybenzylidene)-3,4,5,6-tetrahydropyridin-2-yl)pyridine dihydrochloride

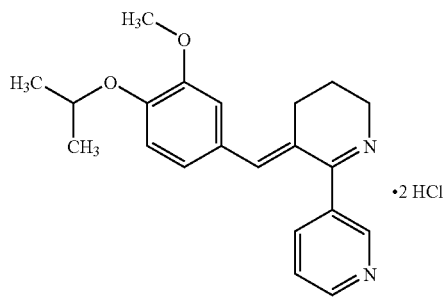

3-(3-(4-Isopropoxy-3-methoxybenzylidene)-3,4,5,6-tetrahydropyridin-2-yl)pyridine dihydrochloride was prepared as described in Lepore, S. D.; He, Y. *J. Org. Chem.*, 2003, 68, 8261-8263. Intermediate 3 (315 mg, 0.86 mmol) (prepared as described in Example 20) was treated with saturated NaHCO$_{3(aq)}$ and extracted three times with EtOAc. The EtOAc extracts were washed with brine, combined, dried over Na$_2$SO$_4$, filtered, concentrated under reduced pressure and dried under vacuum giving 241 mg (95%) of a red solid. PPh$_3$ (225 mg, 0.86 mmol), isopropanol (52 mg, 0.86 mmol) and DMF (0.3 mL) were added to this mixture under N$_2$ at room temperature. This mixture was then treated to ultrasound (42 kHz, Branson brand 5510 sonicator) for several minutes. DIAD (174 mg, 0.86 mmol) was then added as the neat reagent, dropwise, via syringe, under N$_2$, over 3 minutes. This mixture was then treated to ultrasound at room temperature, with occasional agitation of the reaction flask, for 20 minutes. The reaction was quenched with water and extracted three times with EtOAc. The EtOAc extracts were washed with brine, combined, dried over Na$_2$SO$_4$, filtered and concentrated under reduced pressure. The recovered material was then eluted through a 50 gram column of silica gel with 99:1:0.1 CH$_2$Cl$_2$:MeOH:NH$_4$OH (3 liters). The material recovered from this column was dissolved into methanol and treated with 2 eq. of 6 N HCl$_{(aq)}$. This solution was concentrated under reduced pressure and the recovered material dissolved into hot isopropanol to re-crystallize. The crystals were recovered by vacuum filtration, washed with fresh isopropanol, and dried under vacuum giving 46 mg (13%) of a yellow solid. LC-MS: RT=4.87 min, [M+H]$^+$=337.1.

Example 74

Synthesis of 6-(3-(naphthalen-1-ylmethylene)-3,4,5,6-tetrahydropyridin-2-yl)quinoline dihydrochloride

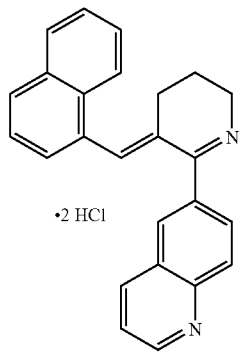

Intermediate 15 (196 mg, 0.93 mmol) (prepared as described in Example 55) was dissolved into isopropanol (6 mL) in a reaction vessel and treated with 6 N HCl$_{(aq)}$ (310 µL, 1.9 mmol). 1-Naphthaldehyde (219 mg, 1.4 mmol) was added, the reaction vessel was sealed, and the reaction heated to 85° C. with stirring overnight. The reaction was cooled to room temperature, concentrated under reduced pressure, treated with saturated NaHCO$_{3(aq)}$, and extracted three times with EtOAc. The EtOAc extracts were washed with brine, combined, dried over Na$_2$SO$_4$, filtered, and concentrated under reduced pressure. The recovered material was eluted through a 20 gram column of silica gel with a 10.5:7:7:0.3:0.03 (750 mL) and 7:7:7:0.5:0.05 (300 mL) Hexane:MtBE:CH$_2$Cl$_2$:MeOH:NH$_4$OH step gradient. The material recovered from this column was then further purified by preparative HPLC using the same conditions and method described for Example 47. The recovered material was dissolved into MeOH and treated with 2 eq. of 6 N HCl$_{(aq)}$. This solution was then concentrated under reduced pressure and the recovered material dissolved into hot isopropanol. After this solution had cooled to room temperature, ether was added until the solution became cloudy. This mixture was cooled to −20° C. Crystals did form and were recovered by vacuum filtration, washed with fresh ether, and dried under vacuum giving 31 mg (6.9%) of a brown solid. LC-MS: RT=5.45 min, [M+H]$^+$=349.0.

Examples 75-114

A. Preparation of Intermediates 16-23

The compounds shown in Table 4 were prepared as described for Intermediate 2 in Example 29 using an appropriate aldehyde.

TABLE 4

| Intermediate | R$_a$ | R$_b$ | R$_c$ | R$_d$ | Yield | LC RT | MS [M + H]$^+$ |
|---|---|---|---|---|---|---|---|
| 16 | H | I | H | H | 63% | 5.08 min | 375.5 |
| 17 | F | Br | H | H | 68% | 4.95 min | 345.4 |
| 18 | H | B(OH)$_2$ | H | H | 72% | 3.51 min | 293.4 |
| 19 | F | H | Br | H | 26% | 5.00 min | 345.4 |
| 20 | OCH$_3$ | Br | H | H | 65% | 4.78 min | 357.5 |
| 21 | H | Br | H | OCH$_3$ | 82% | | |
| 22 | H | Br | H | H | 64% | 5.08 min | 327.0 |
| 23 | H | H | Br | H | 65% | 5.09 min | 327.0 |

B. The compounds shown in Table 5 were prepared as described for Example 59, substituting Intermediates 16-23 for Intermediate 6 and using the appropriate arylhalide.

TABLE 5

| Ex. | R$_a$ | R$_b$ | R$_c$ | R$_d$ | Yield | LC RT | MS [m + H]$^+$ |
|---|---|---|---|---|---|---|---|
| 75 | H | 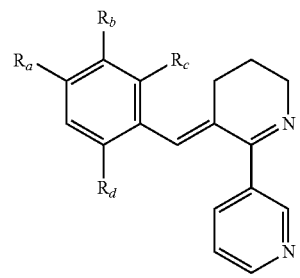 | H | H | 41% | 5.78 min | 359.5 |

TABLE 5-continued
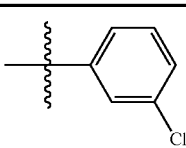
| Ex. | R$_a$ | R$_b$ | R$_c$ | R$_d$ | Yield | LC RT | MS [m + H]$^+$ |
|---|---|---|---|---|---|---|---|
| 76 | H | 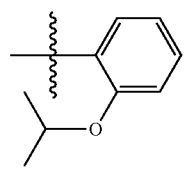 | H | H | 42% | 5.96 min | 359.5 |
| 77 | H | 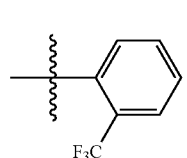 | H | H | 15% | 6.07 min | 383.7 |
| 78 | H | 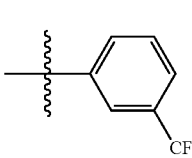 | H | H | 57% | 6.00 min | 393.6 |
| 79 | H | 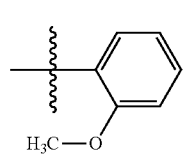 | H | H | 29% | 6.30 min | 393.6 |
| 80 | F | 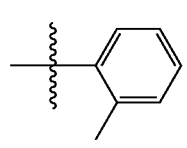 | H | H | 40% | 5.55 min | 373.6 |
| 81 | F | 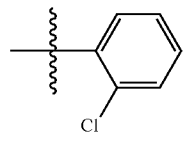 | H | H | 54% | 5.82 min | 357.6 |
| 82 | F | 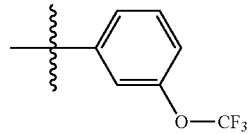 | H | H | 35% | 5.78 min | 377.6 |
| 83 | H |  | H | H | 33% | 6.34 min | 409.7 |

TABLE 5-continued
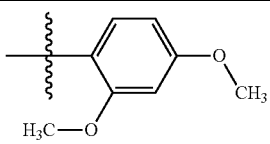
| Ex. | R$_a$ | R$_b$ | R$_c$ | R$_d$ | Yield | LC RT | MS [m + H]$^+$ |
|---|---|---|---|---|---|---|---|
| 84 | H | 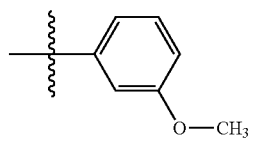 | H | H | 14% | 5.68 min | 385.7 |
| 85 | F | H | Ph | H | 51% | 5.44 min | 343.5 |
| 86 | F | H | 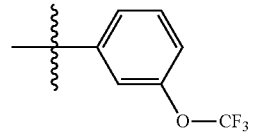 | H | 66% | 5.47 min | 373.6 |
| 87 | F | H | 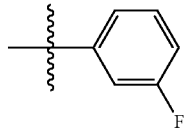 | H | 54% | 6.25 min | 427.7 |
| 88 | F | H | 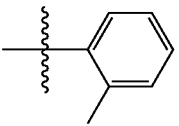 | H | 34% | 5.55 min | 361.6 |
| 89 | H | 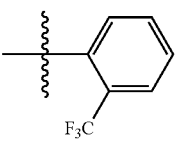 | H | H | 38% | 6.76 min | 325.5 |
| 90 | F | 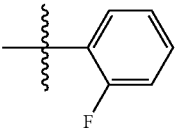 | H | H | 35% | 5.99 min | 411.7 |
| 91 | F | 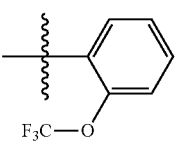 | H | H | 62% | 5.62 min | 361.6 |
| 92 | H |  | H | H | 12% | 6.17 min | 409.7 |

TABLE 5-continued

| Ex. | R_a | R_b | R_c | R_d | Yield | LC RT | MS [m + H]+ |
|---|---|---|---|---|---|---|---|
| 93 | F | 3-(NHC(O)CH₃)phenyl | H | H | 37% | 4.85 min | 400.7 |
| 94 | F | 2-F-3-CF₃-phenyl | H | H | 50% | 6.56 min | 429.7 |
| 95 | OCH₃ | 2-(Ph-O)phenyl | H | H | 30% | 6.29 min | 447.2 |
| 96 | F | 2-(Ph-O)phenyl | H | H | 37% | 6.43 min | 435.7 |
| 97 | OCH₃ | 2-Cl-phenyl | H | H | 53% | 5.64 min | 389.6 |
| 98 | OCH₃ | 2-(Et-O)phenyl | H | H | 39% | 5.67 min | 399.7 |
| 99 | H | 2-(Et-O)phenyl | H | OCH₃ | 13% | 6.00 min | 399.7 |
| 100 | OCH₃ | 2-F-6-(Et-O)phenyl | H | H | 8% | 5.78 min | 417.2 |

TABLE 5-continued
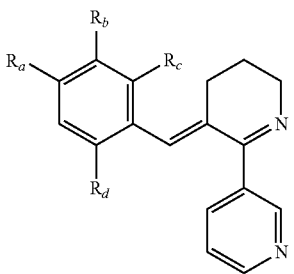
| Ex. | $R_a$ | $R_b$ | $R_c$ | $R_d$ | Yield | LC RT | MS $[m+H]^+$ |
|---|---|---|---|---|---|---|---|
| 101 | H | 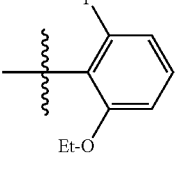 F, Et-O substituted phenyl | H | OCH₃ | 33% | 6.06 min | 417.2 |
| 102 | H | Ph | H | H | 38% | 5.73 min | 325.1 |
| 103 | H | 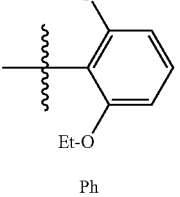 F, Et-O substituted phenyl | H | H | 25% | 6.04 min | 387.1 |
| 104 | OCH₃ | Ph | H | H | 43% | 5.47 min | 355.1 |
| 105 | H | 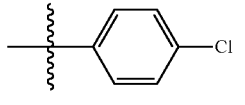 4-Cl phenyl | H | H | 16% | 6.19 min | 359.1 |
| 106 | OCH₃ | 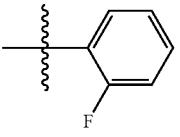 2-F phenyl | H | H | 36% | 5.63 min | 373.1 |
| 107 | H | H | 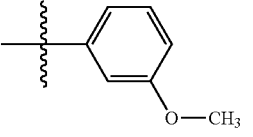 3-OCH₃ phenyl | H | 32% | 5.54 min | 355.1 |
| 108 | OCH₃ | H | Ph | H | 34% | 5.45 min | 355.1 |
| 109 | OCH₃ | 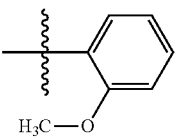 2-OCH₃ phenyl | H | H | 10% | 5.61 min | 385.1 |
| 110 | OCH₃ | 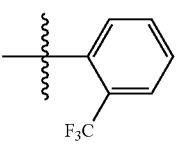 2-CF₃ phenyl | H | H | 17% | 5.96 min | 423.1 |

TABLE 5-continued

[Structure with Ra, Rb, Rc, Rd substituents on benzene connected via =CH to piperidine ring with pyridin-3-yl]

| Ex. | $R_a$ | $R_b$ | $R_c$ | $R_d$ | Yield | LC RT | MS [m + H]⁺ |
|---|---|---|---|---|---|---|---|
| 111 | OCH₃ | 2-methylphenyl | H | H | 26% | 5.79 min | 369.2 |
| 112 | H | 2-ethoxyphenyl | H | H | 10% | 6.26 min | 369.1 |
| 113 | F | Ph | H | H | 14% | 5.80 min | 343.1 |
| 114 | F | 2-ethoxyphenyl | H | H | 50% | 6.13 min | 387.1 |

While this invention has been particularly shown and described with references to example embodiments thereof, it will be understood by those skilled in the art that various changes in form and details may be made therein without departing from the scope of the invention encompassed by the appended claims.

What is claimed is:

1. The compound of Formula (II):

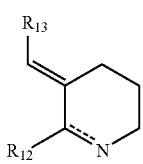

(II)

or a pharmaceutically acceptable salt thereof, wherein:

$R_{12}$ is selected from the group consisting of:

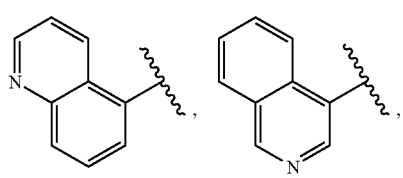

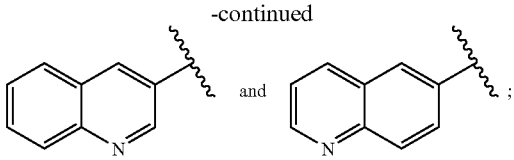

$R_{13}$ is selected from the group consisting of 6 membered monocyclic aryl, 5 or 6 membered monocyclic heteroaryl comprising 1-3 heteroatoms, 8-12 membered bicyclic aryl, 8-12 membered bicyclic heteroaryl comprising 1-6 heteroatoms, 11-14 membered tricyclic aryl and 11-14 membered heteroaryl comprising 1-9 heteroatoms, wherein each of said heteroatoms is independently selected from the group consisting of O, N and S and wherein said aryl and heteroaryl are each optionally substituted with one or more $R_{17}$;

Each $R_{14}$ is independently selected from the group consisting of H, C1-C10 alkyl, C2-C10 alkenyl, C2-C10 alkynyl, C3-C10 cycloalkyl, C4-C10 cycloalkenyl, 3-10 membered heterocycloalkyl, 4-10 membered heterocycloalkenyl, aryl, heteroaryl and haloalkyl;

Each $R_{15}$ is independently selected from the group consisting of halo, haloalkyl, $CF_3$, $OCF_3$, $OR_{14}$, $SR_{14}$, $C(O)R_{14}$, $OC(O)R_{14}$, $C(O)OR_{14}$, $NR_{14}R_{14}$, $NO_2$, $CN$, $OC(O)NR_{14}R_{14}$, $C(O)NR_{14}R_{14}$, $N(R_{14})C(O)R_{14}$, $N(R_{14})(COOR_{14})$, $S(O)_tNR_{14}R_{14}$, C3-C8 cycloalkyl, C4-C10 cycloalkenyl, 3-8 membered heterocycloalkyl, 4-10 membered heterocycloalkenyl, C5-C11 bicycloalkyl, C5-C11 bicycloalkenyl, 5-11 membered heterobicycloalkyl, 5-11 membered heterobicycloalkenyl, aryl and heteroaryl Each $R_{16}$ is independently selected from the group consisting of $R_{15}$, C1-C10 alkyl, C1-C10 alkyl substituted with one or more $R_{15}$, C2-C10 alkenyl, C2-C10 alkenyl substituted with one or more $R_{15}$, C2-C10 alkynyl and C2-C10 alkynyl substituted with one or more $R_{15}$;

Each $R_{17}$ is independently selected from the group consisting of C1-C10 alkyl, C1-C10 alkyl substituted with one or more $R_{15}$, C2-C10 alkenyl, C2-C10 alkenyl substituted with one or more $R_{15}$, C2-C10 alkynyl, C2-C10 alkynyl substituted with one or more $R_{16}$, C3-C10 cycloalkyl, C3-C10 cycloalkyl substituted with one or more $R_{16}$, C4-C10 cycloalkenyl, C4-C10 cycloalkenyl substituted with one or more $R_{16}$, 3-8 membered heterocycloalkyl, 3-8 membered heterocycloalkyl substituted with one or more $R_{16}$, 4-10 membered heterocycloalkenyl, 4-10 membered heterocycloalkenyl substituted with one or more $R_{16}$, C5-C11 bicycloalkyl, C5-C11 bicycloalkyl substituted with one or more $R_{16}$, C5-C11 bicycloalkenyl, C5-C11 bicycloalkenyl substituted with one or more $R_{16}$, 5-11 membered heterobicycloalkyl, 5-11 membered heterobicycloalkyl substituted with one or more $R_{16}$, 5-11 membered heterobicycloalkenyl, 5-11 membered heterobicycloalkenyl substituted with one or more $R_{16}$, halo, $CF_3$, $OCF_3$, $OR_{14}$, $SR_{14}$, $NR_{14}R_{14}$, $C(O)OR_{14}$, $NO_2$, CN, $C(O)R_{14}$, $C(O)C(O)R_{14}$, $C(O)NR_{14}R_{14}$, $C(O)C(O)NR_{14}R_{14}$, $N(R_{14})C(O)R_{14}$, $NR_{14}S(O)_tR_{14}$, $N(R_{14})C(O)OR_{14}$, $NR_{14}C(O)R_{14}$, $NR_{14}C(O)NR_{14}R_{14}$, $NR_{14}S(O)_tNR_{14}R_{14}$, $NR_{14}S(O)_tR_{14}$, $S(O)_tR_{14}$, $S(O)_tNR_{14}R_{14}$, $OC(O)R_{14}$, optionally substituted aryl and optionally substituted heteroaryl; and t is 1 or 2.

* * * * *